US011654274B2

(12) United States Patent
Timms et al.

(10) Patent No.: US 11,654,274 B2
(45) Date of Patent: May 23, 2023

(54) HEART PUMP DRIVE AND BEARING

(71) Applicant: BiVACOR Inc., Houston, TX (US)

(72) Inventors: Daniel Timms, Long Beach, CA (US);
Matthias Kleinheyer, Aspley (AU);
Nicholas Greatrex, Cornubia (AU);
Alexei Filatov, Irvine, CA (US)

(73) Assignee: BiVACOR Inc., Houston, TX (US)

( * ) Notice: Subject to any disclaimer, the term of this patent is extended or adjusted under 35 U.S.C. 154(b) by 620 days.

(21) Appl. No.: 16/591,850

(22) Filed: Oct. 3, 2019

(65) Prior Publication Data
US 2020/0171224 A1 Jun. 4, 2020

Related U.S. Application Data

(63) Continuation of application No. PCT/US2018/026265, filed on Apr. 5, 2018.
(Continued)

(51) Int. Cl.
*A61M 60/82* (2021.01)
*A61M 60/824* (2021.01)
(Continued)

(52) U.S. Cl.
CPC .......... *A61M 60/82* (2021.01); *A61M 60/148* (2021.01); *A61M 60/178* (2021.01);
(Continued)

(58) Field of Classification Search
CPC ................. A61M 2205/332; A61M 60/50
See application file for complete search history.

(56) References Cited

U.S. PATENT DOCUMENTS 2,700,343 A  1/1955 Pezzillo, Jr. et al.
4,135,253 A  1/1979 Reich et al.
(Continued)

FOREIGN PATENT DOCUMENTS

AU  7993698 A  2/1999
CA  2638958 A1  12/2000
(Continued)

OTHER PUBLICATIONS

Amano, et al., An ultrasonic actuator with multi-degree of freedom using bending and longitudinal vibrations of a single stator; IEEE Ultrason. Symp. Proc.; pp. 667-670; 1998.
(Continued)

*Primary Examiner* — Jacqueline Wozincki
(74) *Attorney, Agent, or Firm* — Goodwin Procter LLP

(57) ABSTRACT

A heart pump including a housing defining a cavity including at least one inlet aligned with an axis of the cavity and at least one outlet provided in a circumferential outer wall of the cavity. An impeller is provided within the cavity, the impeller including a rotor and vanes mounted on the rotor for urging fluid from the inlet radially outwardly to the outlet. A drive is provided for rotating the impeller in the cavity, the drive including a plurality of circumferentially spaced permanent drive magnets mounted within and proximate a first face of the rotor, adjacent drive magnets having opposing polarities and a plurality of circumferentially spaced drive coils mounted within the housing proximate a first end of the cavity, each coil being wound on a respective drive stator pole of a drive stator and being substantially radially aligned with the drive magnets, the drive coils being configured to generate a drive magnetic field that cooperates with the drive magnets to thereby rotate the impeller. A magnetic bearing is also provided to thereby at least one of
(Continued)

control an axial position of the impeller and at least partially restrain radial movement of the impeller.

17 Claims, 49 Drawing Sheets

Related U.S. Application Data

(60) Provisional application No. 62/539,083, filed on Jul. 31, 2017, provisional application No. 62/482,048, filed on Apr. 5, 2017.

(51) Int. Cl.

| | | |
|---|---|---|
| *A61M 60/422* | (2021.01) | |
| *A61M 60/806* | (2021.01) | |
| *A61M 60/216* | (2021.01) | |
| *A61M 60/148* | (2021.01) | |
| *A61M 60/419* | (2021.01) | |
| *F04D 13/06* | (2006.01) | |
| *A61M 60/196* | (2021.01) | |
| *A61M 60/822* | (2021.01) | |
| *A61M 60/178* | (2021.01) | |
| *A61M 60/183* | (2021.01) | |
| *H02K 7/14* | (2006.01) | |

(52) U.S. Cl.
CPC ........ *A61M 60/183* (2021.01); *A61M 60/196* (2021.01); *A61M 60/216* (2021.01); *A61M 60/419* (2021.01); *A61M 60/422* (2021.01); *A61M 60/806* (2021.01); *A61M 60/822* (2021.01); *A61M 60/824* (2021.01); *F04D 13/06* (2013.01); *A61M 2205/04* (2013.01); *A61M 2205/103* (2013.01); *A61M 2205/332* (2013.01); *H02K 7/14* (2013.01)

(56) References Cited

U.S. PATENT DOCUMENTS

| | | | |
|---|---|---|---|
| 4,589,822 A | 5/1986 | Clausen et al. | |
| 5,041,934 A | 8/1991 | Stefansky | |
| 5,049,134 A | 9/1991 | Golding et al. | |
| 5,195,877 A | 3/1993 | Kletschka | |
| 5,290,227 A | 3/1994 | Pasque | |
| 5,306,295 A | 4/1994 | Kolff et al. | |
| 5,405,251 A | 4/1995 | Sipin | |
| 5,601,418 A | 2/1997 | Ohara et al. | |
| 5,613,935 A | 3/1997 | Jarvik | |
| 5,725,357 A | 3/1998 | Nakazeki et al. | |
| 5,840,070 A | 11/1998 | Wampler | |
| 5,851,174 A | 12/1998 | Jarvik et al. | |
| 5,890,883 A | 4/1999 | Golding et al. | |
| 5,928,131 A | 7/1999 | Prem | |
| 5,971,023 A | 10/1999 | Clague et al. | |
| 6,017,093 A | 1/2000 | Moser | |
| 6,017,903 A | 1/2000 | Slusher et al. | |
| 6,030,188 A | 2/2000 | Nojiri et al. | |
| 6,048,363 A | 4/2000 | Nagyszalanczy et al. | |
| 6,074,180 A | 6/2000 | Khanwilkar et al. | |
| 6,179,773 B1 | 1/2001 | Prem et al. | |
| 6,220,832 B1 | 4/2001 | Schob | |
| 6,227,797 B1 | 5/2001 | Watterson et al. | |
| 6,234,772 B1 | 5/2001 | Wampler et al. | |
| 6,264,635 B1 | 7/2001 | Wampler et al. | |
| 6,293,901 B1 | 9/2001 | Prem | |
| 6,312,443 B1 | 11/2001 | Stone | |
| 6,351,048 B1 | 2/2002 | Schob et al. | |
| 6,394,769 B1 | 5/2002 | Bearnson et al. | |
| 6,422,838 B1 | 7/2002 | Sloteman | |
| 6,527,698 B1 | 3/2003 | Kung et al. | |
| 6,547,530 B2 | 4/2003 | Ozaki et al. | |
| 6,575,717 B2 | 6/2003 | Ozaki et al. | |
| 6,589,030 B2 | 7/2003 | Ozaki | |
| 6,623,475 B1 | 9/2003 | Siess | |
| 6,626,644 B2 | 9/2003 | Ozaki | |
| 6,638,011 B2 | 10/2003 | Woodard et al. | |
| 6,664,714 B2 | 12/2003 | Magnussen et al. | |
| 6,688,861 B2 | 2/2004 | Wampler | |
| 6,690,101 B2 | 2/2004 | Magnussen et al. | |
| 6,717,311 B2 | 4/2004 | Locke | |
| 6,790,171 B1 | 9/2004 | Grundeman et al. | |
| 6,866,625 B1 | 3/2005 | Ayre et al. | |
| 6,870,304 B2 | 3/2005 | Magnussen et al. | |
| 7,229,474 B2 | 6/2007 | Hoffmann et al. | |
| 7,274,131 B2 | 9/2007 | Li et al. | |
| 7,435,059 B2 | 10/2008 | Smith et al. | |
| 7,439,652 B2 | 10/2008 | Ganor et al. | |
| 7,462,019 B1 | 12/2008 | Allarie et al. | |
| 7,476,077 B2 | 1/2009 | Woodard et al. | |
| 7,645,225 B2 | 1/2010 | Medvedev et al. | |
| 7,704,054 B2 | 4/2010 | Horvath et al. | |
| 7,914,436 B1 | 3/2011 | Kung | |
| 7,931,581 B2 | 4/2011 | Cohn | |
| 8,110,967 B2 | 2/2012 | Ting et al. | |
| 8,210,829 B2 | 7/2012 | Horvath et al. | |
| 8,226,373 B2 | 7/2012 | Yaegashi | |
| 8,506,471 B2 | 8/2013 | Bourque | |
| 8,551,163 B2 | 10/2013 | Aber et al. | |
| 8,613,696 B2 | 12/2013 | Medvedev et al. | |
| 8,632,449 B2 | 1/2014 | Masuzawa et al. | |
| 8,636,638 B2 | 1/2014 | Timms | |
| 8,747,293 B2 | 6/2014 | Arndt et al. | |
| 8,834,345 B2 | 9/2014 | Yanai et al. | |
| 8,961,388 B2 | 2/2015 | Bourque | |
| 9,011,312 B2 | 4/2015 | Bourque | |
| 9,095,428 B2 | 8/2015 | Kabir et al. | |
| 9,211,368 B2 | 12/2015 | Wampler | |
| 9,427,508 B2 | 8/2016 | Reyes et al. | |
| 9,433,717 B2 | 9/2016 | Bourque | |
| 9,492,601 B2 | 11/2016 | Casas et al. | |
| 9,511,179 B2 | 12/2016 | Casas et al. | |
| 9,512,852 B2 | 12/2016 | Wampler et al. | |
| 9,709,061 B2 | 7/2017 | Yanai et al. | |
| 9,801,988 B2 | 10/2017 | Bourque | |
| 9,901,666 B2 | 2/2018 | Cotter | |
| 10,077,777 B2 | 9/2018 | Horvath et al. | |
| 10,086,122 B2 | 10/2018 | Bourque | |
| 10,371,152 B2 | 8/2019 | Yanai et al. | |
| 10,543,301 B2 | 1/2020 | Timms | |
| 11,154,703 B2 | 10/2021 | Timms | |
| 2001/0002234 A1 | 5/2001 | Woodard et al. | |
| 2002/0076322 A1 | 6/2002 | Maeda et al. | |
| 2002/0094281 A1 | 7/2002 | Khanwilkar et al. | |
| 2002/0109621 A1 | 8/2002 | Khair et al. | |
| 2003/0023131 A1 | 1/2003 | Antaki | |
| 2003/0176760 A1 | 9/2003 | El Oakley et al. | |
| 2004/0267344 A1 | 12/2004 | Stett et al. | |
| 2005/0008496 A1 | 1/2005 | Tsubouchi et al. | |
| 2005/0135948 A1 | 6/2005 | Olsen et al. | |
| 2005/0214131 A1 | 9/2005 | Miles et al. | |
| 2007/0249888 A1 | 10/2007 | Wu et al. | |
| 2007/0253842 A1 | 11/2007 | Horvath et al. | |
| 2010/0168848 A1 | 7/2010 | Horvath et al. | |
| 2011/0118537 A1 | 5/2011 | Wampler | |
| 2011/0118619 A1 | 5/2011 | Burton et al. | |
| 2011/0148253 A1 | 6/2011 | Friend et al. | |
| 2012/0095280 A1 | 4/2012 | Timms | |
| 2012/0245680 A1* | 9/2012 | Masuzawa | A61M 60/538 623/3.11 |
| 2012/0253103 A1 | 10/2012 | Robert | |
| 2012/0289897 A1 | 11/2012 | Friend et al. | |
| 2014/0100413 A1 | 4/2014 | Casas et al. | |
| 2014/0171727 A1 | 6/2014 | Nusser et al. | |
| 2014/0288354 A1 | 9/2014 | Timms et al. | |
| 2017/0340788 A1 | 11/2017 | Korakianitis et al. | |
| 2018/0185567 A1 | 7/2018 | Madhani et al. | |
| 2018/0228955 A1 | 8/2018 | Granegger et al. | |

(56) References Cited

U.S. PATENT DOCUMENTS

| | | | |
|---|---|---|---|
| 2018/0311422 | A1 | 11/2018 | Greatrex et al. |
| 2019/0001037 | A1 | 1/2019 | Bonde |

FOREIGN PATENT DOCUMENTS

| | | | |
|---|---|---|---|
| CN | 101371041 | A | 2/2009 |
| CN | 101873870 | A | 10/2010 |
| CN | 102397598 | A | 4/2012 |
| CN | 102711862 | A | 10/2012 |
| CN | 102458498 | B | 6/2015 |
| CN | 102711862 | B | 12/2015 |
| EP | 1065383 | A1 | 1/2001 |
| EP | 1188453 | A1 | 3/2002 |
| EP | 1495773 | A2 | 1/2005 |
| EP | 1273096 | B1 | 11/2005 |
| EP | 1630897 | A1 | 3/2006 |
| EP | 1674119 | A1 | 6/2006 |
| EP | 1721346 | B1 | 10/2007 |
| EP | 2538086 | A1 | 12/2012 |
| JP | 2001061957 | A | 3/2001 |
| JP | 2001-224568 | A | 8/2001 |
| JP | 2003-230547 | A | 8/2003 |
| JP | 2004-61251 | A | 2/2004 |
| JP | 2005-282675 | A | 10/2005 |
| JP | 2006-525460 | A | 11/2006 |
| JP | 3930834 | B2 | 6/2007 |
| JP | 2009-011767 | A | 1/2009 |
| WO | WO-1997/042414 | A1 | 11/1997 |
| WO | WO-00/32256 | A1 | 6/2000 |
| WO | WO-00/32257 | A1 | 6/2000 |
| WO | WO-2002-053028 | A8 | 12/2002 |
| WO | WO-2004-032738 | A1 | 4/2004 |
| WO | WO-2004-043252 | A1 | 5/2004 |
| WO | WO-2004-047636 | A1 | 6/2004 |
| WO | WO-2004/098677 | A1 | 11/2004 |
| WO | WO-2004-098389 | A3 | 3/2005 |
| WO | WO-2006-053384 | A1 | 5/2006 |
| WO | WO-2007-056493 | A1 | 5/2007 |
| WO | WO-2007/084339 | A3 | 1/2008 |
| WO | WO-2009/058726 | A1 | 5/2009 |
| WO | WO-2010/118475 | A1 | 10/2010 |
| WO | WO-2010-118476 | A1 | 10/2010 |
| WO | WO-2011-026187 | A1 | 3/2011 |
| WO | WO-2011-054545 | A1 | 5/2011 |
| WO | WO-2013-033783 | A1 | 3/2013 |
| WO | WO-2017-120453 | A1 | 7/2017 |
| WO | WO-2017120449 | A2 | 7/2017 |
| WO | WO-2017-120451 | A3 | 8/2017 |
| WO | WO-2017/120449 | A3 | 11/2017 |

OTHER PUBLICATIONS

Gaddum, Nicholas Richard, "Passive Control of a Bi-Ventricular Assist Device: An experimental and Numerical Investigation", (Thesis), Queensland University of Technology 2008, Ch. 3, sections 3.4.3.1, 3.4.3.4, 3.6 to 3.7 & Figs. 3-12 to 3-14, 3-16, 3-18, 3-23, 3-25 to 3-27, 3-35 to 3-36; Ch. 8, section 8.2.1.

Gouda et al.; A miniaturization of the multi-degree-of-freedom ultrasonic actuator using a small cylinder fixed on a substrate; Ultrasonics; 44 supp. 1; pp. e617-e620; Dec. 22, 2006.

Greatrex N. et al. 'Axial magnetic bearing . . . ', 2010, IEEE Transactions in Biomedical Eng, vol. 57(3), pp. 714-721.

Kanda et al. A micro ultrasonic motor using a micro-machined cylindrical bulk PZT transducer; Sensors and Actuators; 127; pp. 131-138; Dec. 19, 2009.

Kawano et al.; Application of a multi-DOF ultrasonic servomotor in an auditory tele-existence robot; IEEE Trans. Robotics; 21 (5); pp. 790-800; Oct. 2005.

Khoo et al.; Triple degree-of-freedom piezoelectric micromotor via flexural-axial coupled vibration; IEEE Transactions on ultrasonics, Ferroelectrics, and Frequency Control; 56(8); pp. 1716-1724; Aug. 2009.

Maslen E. et cl. 'Feedback Control Applications in Artificial Hearts . . . ' 1998 IEEE Control Systems Mag, vol. 18(6), pp. 26-34.

Masuzawa T. et al., 'Magnetically Suspended Centrifugal . . . ' 2002, ASAIO Journal, pp. 437-442.

Masuzawa, T., H. Onuma, and Y. Okada, "Zero Power Control for Magnetically Suspended Artificial Heart." Jido Seigyo Rengo Koenkai Koen Ronbunshu, 2004. 47: p. 322.

Masuzawa, Toru et al., "An Ultradurable and Compact Rotary Blood Pump with a Magnetically Suspended Impeller in the Radial Direction", Artificial Organs, vol. 25, Issue 5, 2001, pp. 395-399, Abstract; Suspension system (pp. 396-397); Discussion (p. 398); Figs. 1-6.

Masuzawa, Toru et al., "Magnetically Suspended Centrifugal Blood Pump with an Axially Levitated Motor", Artificial Organs, vol. 27, Issue 7, 2003, pp. 631-638 Abstract; axially levitated motor (pp. 632-633); Motor design and experimental set-up (pp. 633-634); levitation performance (pp. 634-635); Discussion (pp. 636-638); Figs. 1, 3-5, 8 and 13.

Masuzawa, Toru et al., "Magnetically Suspended Rotary Blood Pump with Radial Type Combined Motor-Bearing", Artificial Organs, vol. 24, Issue 6, 2000, pp. 468-474, Abstract; Suspension control (pp. 468-469); Prototype of the magnetically suspended centrifugal pump (pp. 469-470); Discussion (p. 471); Figs. 1-6.

Morita, et al.; A cylindrical micro ultrasonic motor using PZT thin film deposited by single process hydrothermal method (Ø2.4 mm, L=10 mm stator transducer); IEEE Trans. Ferroelectr. Freq. Contrl; 45(5); pp. 1178-1187; Sep. 1998;.

Niwano, et al.; An active dummy head driven by a multi-degree-of-freedom ultrasonic actuator; WCU Conf. Proc. 1597; 2003.

Park, et al.; Study on multi-DOF ultrasonic actuator for laparoscopic instrument; JSME int. J.; 47(2); pp. 574-581; 2004.

Rogers; A diameter 300 μm bragg reflector for acoustic isolation of resonant micro-actuators; J. Micromech. Microeng. 21 (4); pp. 1-4; Apr. 2011.

Rogers; Piezoelectric ultrasonic micro-motor system for minimally invasive surgery—the intellimotor; AIP Conf. Proc. 1433 pp. 705-708; 2012.

Rogers; Three degree-of-freedom piezoelectric ultrasonic micromotor with a major diameter of 350 μm; J. Micromech. Microeng.;20(12); pp. 1-5; Dec. 2010.

Satoshi Ueno et al., "Characteristics of axial force and rotating torque and their control of permanent magnet type axial gap self-bearing motor", Electrical Engineering in Japan, vol. 132, Issue 1, 2000, pp. 81-91 (whole document).

Sin, D.C. et al., "Blood flow in a double output centrifugal artificial heart pump as a biventricular assist device", Anziam J. 48 (CTAC2006), Feb. 27, 2008, pp. C949-C962, Materials and Method section (pp. C952-C955); Figures 2-4.

Takemura et al.; Characterstics of an ultrasonic motor capable of generating a multi-degrees of freedom motion; Proc. IEEE int. Conf. on Robotics and Automation; vol. 4; pp. 3660-3665; Apr. 2000.

Takemura et al.; Control of multi-dof ultrasonic actuator for dexterous surgical instrument; Journal of Sound and Vibration; 311; pp. 652-666; Nov. 26, 2007.

Timms, D.L., "Design, Development and Evaluation of Centrifugal Type Ventricular Assist Devices", (Thesis), Queensland University of Technology, 2005 Ch. 4, sections 4.4.4-3 BiLVAD and 4.4.4 Bi-VAD & Figure 4-20 to 4-21; Ch. 5—VAD Experimental Evaluation; Ch. 6, VAD Summary & Figures 6-1 to 6-8.

Wajchman et al.; An ultrasonic piezoelectric motor utilizing axial-torsional coupling in a pretwisted non-circular cross-sectioned primatic beam; IEEE Transactions of Ultrasonics, Ferroelectrics, and Frequency Control; 55(4); pp. 832-840; Apr. 2008; and.

Watson Peizoelectric ultrasonic micro/milli-scale actuators; Sensors Actuators; 152; pp. 219-233; Apr. 2, 2009.

Gulich, Gentrifugal pumps 2nd Ed (2010), pp. 352-357.

Sonune, et al,, "Performance Investigation of Centrifugal Pump By Varying Blade Angles of the Impeller-A" IJCET INPRESSO Special Issue—7 (Mar. 2017), pp. 399-401.

International Search Report issued for PCT/US2018/026265, dated Dec. 5, 2018.

(56) References Cited

OTHER PUBLICATIONS

International Preliminary Report on Patentability isued for PCT/US2018/026265, dated Oct. 8, 2019.
"Blade Design", Design of Hydraulic Components, pp. 352-357.

* cited by examiner

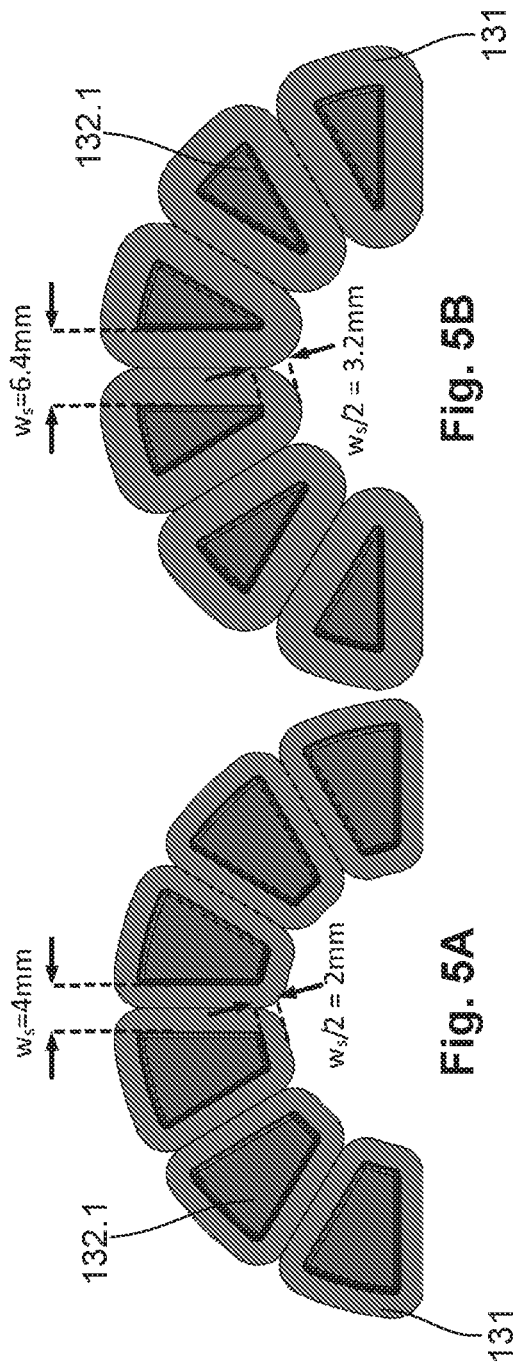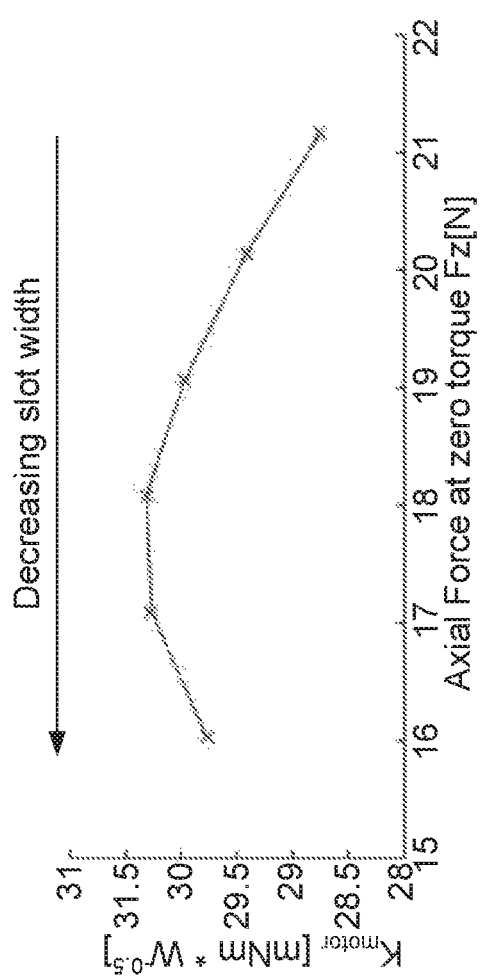

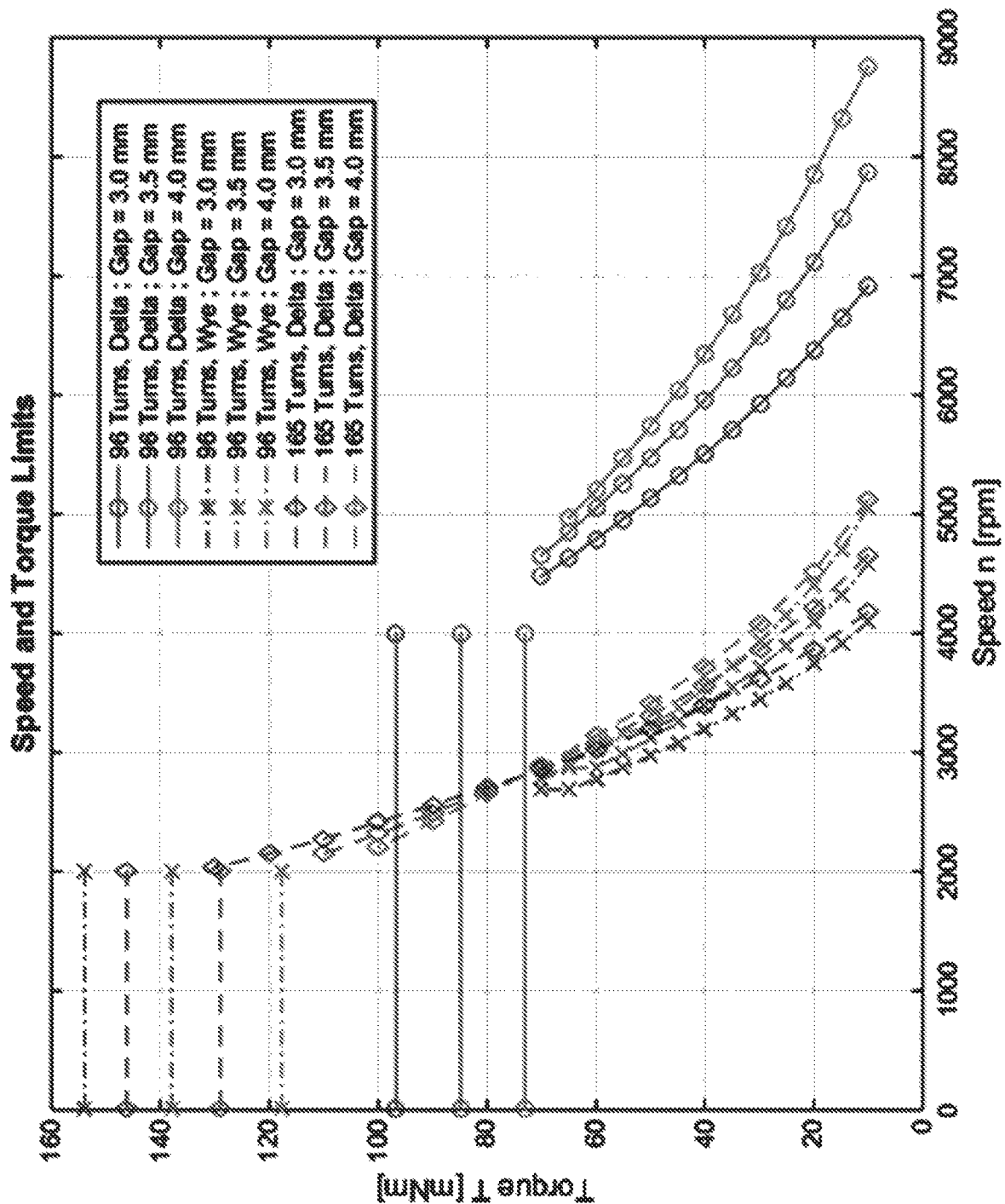

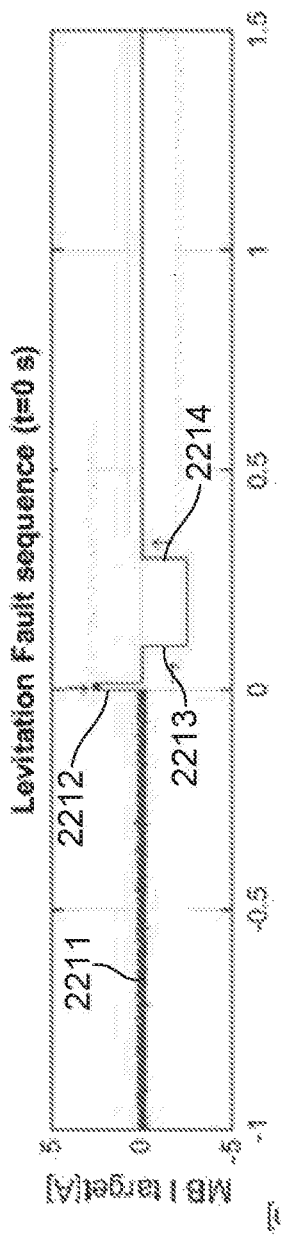
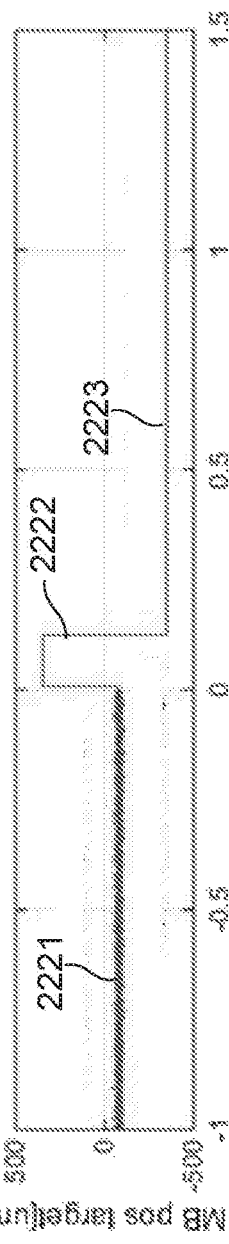
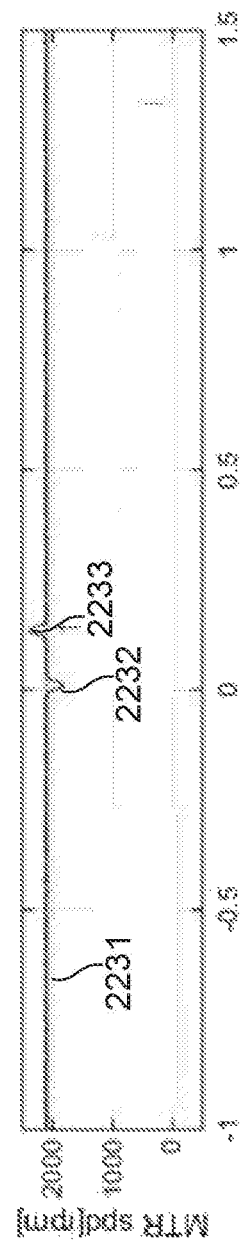
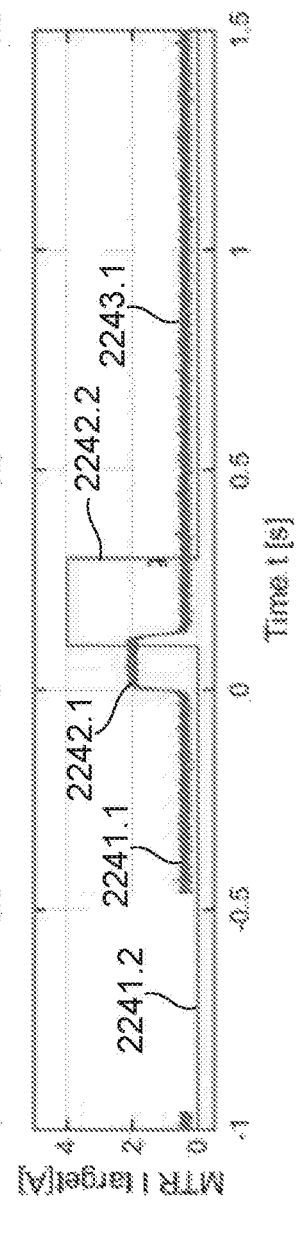
Fig. 22A
Fig. 22B
Fig. 22C
Fig. 22D

HEART PUMP DRIVE AND BEARING

CROSS-REFERENCE TO RELATED APPLICATIONS

This application claims the benefit of priority under 35 U.S.C. § 120 to International Patent Application Number PCT/US2018/026265 entitled "Heart Pump Drive and Bearing," filed on Apr. 5, 2018, which claims the benefit of priority under 35 U.S.C. § 119 to U.S. Provisional Patent Application No. 62/482,048, filed on Apr. 5, 2017, and U.S. Provisional Patent Application No. 62/539,083, filed on Jul. 31, 2017, the contents of each of which are incorporated herein by reference in their entirety.

BACKGROUND OF THE INVENTION

The present invention relates to a heart pump and in particular to a heart pump including improved flow characteristics.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

The use of rotary impeller based mechanical pumps to treat heart failure is increasing as the general population ages and the number of donor organs for heart transplantation remains limited. Devices can be used to bridge a patient to heart trans-plant, to recovery, or indeed as a destination alternative.

WO2004098677 and WO2006053384A1 each describe a double sided impeller that rotates at a common speed, with each side of the impeller respectively configured for left and right heart assistance. This effectively introduces an inherent problem regarding the ability to independently control and thus balance the outflow from the left and right sides of the device, i.e. an increase in impeller rotational speed will produce a corresponding increase in outflow from both cavities.

WO2006053384A1 addressed this issue by introducing the ability to axially displace the rotating impeller within the cavity so as to simultaneously alter the relative efficiencies of each side of the device. However, when the control method used to achieve this axial displacement is active, such pumps require the use of feedback signals from pressure sensors and the like to actively control and maintain a desired set axial location. This method of control would inherently consume excessive amounts of electrical power and introduce issues relating to the long term reliability of blood contacting sensors.

U.S. Pat. No. 8,636,638 describes a controller for a heart pump that determines movement of an impeller within a cavity in a first axial direction, the cavity including at least one inlet and at least one outlet, and the impeller including vanes for urging fluid from the inlet to the outlet, causing a magnetic bearing to move the impeller in a second axial direction opposite the first axial direction, the magnetic bearing including at least one coil for controlling an axial position of the impeller within the cavity, determining an indicator indicative of the power used by the magnetic bearing and causing the magnetic bearing to control the axial position of the impeller in accordance with the indicator to thereby control a fluid flow between the inlet and the outlet.

U.S. Pat. No. 7,435,059 describes a system for pumping blood to assist or assume the cardiac function of a patient is characterized by a blood pump that exhibits a steep pump curve such that only small changes in pump flow occur for large changes in differential pressure across the pump. The pump therefore exhibits flow-limiting characteristics to protect the physiological system against harmful flow rates. Pump flow may also be limited by controlling the current provided to a driver from a power supply or by suitable restrictions within or external to the pump housing.

When creating such heart pumps, the particular design of the pump, can have a major impact on the performance of the heart pump, and in particular, the ability to pump blood at different flow rates depending on the physiological requirements of the subject to which the pump is fitted.

Traditional wisdom has been to produce a pump that has optimum operating efficiency at a typical flow rate for a subject, which typically corresponds to a flow rate of about five to six litres per minute, thereby minimising the power consumed by the pump. Additionally, it is typical to design pumps having a relatively low flow sensitivity to preload, as described for example in U.S. Pat. No. 7,435,059, so that the pump exhibits flow-limiting characteristics to protect the physiological system against harmful flow rates or pressures.

Such configurations result in a heart pump having a steep pump curve which is a plot of the flow rate against head pressure across the pump (the difference between the inlet and outlet pressures), for a given impeller rotational speed. This shows that a large change in pressures is required in order to cause a change in flow rate through the pump thereby providing the aforementioned flow-limiting characteristics.

In such an arrangement, it may be necessary to vary the rotational speed and/or axial position of the impeller to thereby control pump outflow, in order to account for changes in pressures within the subject's circulatory system. However, such control systems require information regarding the physiological state of the subject, such as blood pressures or flow rates, in order to function correctly. This requires the use of complex sensing techniques and/or implanted sensors, which are undesirable, and in many cases makes assumptions regarding at least some parameters, such as blood viscosity, meaning they can be inaccurate. As a result, many existing heart pumps have only a limited ability to accommodate physiological changes, meaning the subjects are often restricted in terms of activities they are able to perform.

SUMMARY OF THE PRESENT INVENTION

In one broad form an aspect of the present invention seeks to provide a heart pump including: a housing defining a cavity including: at least one inlet aligned with an axis of the cavity; and, at least one outlet provided in a circumferential outer wall of the cavity; an impeller provided within the cavity, the impeller including a rotor and vanes mounted on the rotor for urging fluid from the inlet radially outwardly to the outlet; a drive for rotating the impeller in the cavity, the drive including: a plurality of circumferentially spaced permanent drive magnets mounted within and proximate a first face of the rotor; and, a plurality of circumferentially spaced drive coils mounted within the housing proximate a first end of the cavity, each coil being wound on a respective drive stator pole of a drive stator and being substantially radially aligned with the drive magnets, the drive coils being configured to generate a drive magnetic field that cooperates with the drive magnets to thereby rotate the impeller; and, a magnetic bearing including: first and second annular magnetic bearing members mounted within and proximate a second face of the rotor, the first magnetic bearing member being provided radially outwardly of the second magnetic bearing member; a number of circumferentially spaced substantially U-shaped bearing stators mounted in the housing proximate a second end of the cavity, each U-shaped bearing stator having first and second bearing stator legs that interact with the first and second magnetic bearing members respectively; and, at least one bearing coil on each bearing stator that generates a magnetic field that cooperates with the magnetic bearing members to thereby at least one of: control an axial position of the impeller; and, at least partially restrain radial movement of the impeller.

In one embodiment: the first and second bearing stator legs are substantially magnetically aligned with the first and second magnetic bearing members respectively; the first and second bearing stator legs are substantially radially aligned with the first and second magnetic bearing members respectively; the first and second bearing stator cooperate with the first and second magnetic bearing members respectively so that a radial force from an individual bearing is about between 0 N-2N when the bearing stator legs are substantially aligned with the magnetic bearing members; at least one of the first and second bearing stator legs are radially offset from a respect one of first and second magnetic bearing members by a distance that is at least one of: less than 1 mm; less than 0.5 mm; and, less than 0.2 mm.

In one embodiment the drive stator includes a soft magnetic composite core including a plurality of drive stator poles extending in an axial direction from an annular drive stator yoke.

In one embodiment the drive stator yoke has a thickness of at least one of: between 1 mm and 2.5 mm; about 1.75 mm.

In one embodiment the drive stator poles are at least one of: wedge shaped; triangular; and, trapezoidal.

In one embodiment adjacent drive stator poles are separated by a slot having at least one of: a width of at least one of: between 4 mm and 7.4 mm; about 6 mm; and, a depth of at least one of: between 4 mm and 14 mm; about 11.25 mm.

In one embodiment the drive stator has at least one of: an inner radius of at least one of: between 14 mm and 18 mm; and, about 16 mm; and, an outer radius of at least one of: between 22 mm and 25 mm; and, about 24.5 mm.

In one embodiment each drive magnet at least one of: transects an angle at least one of: between 15° and 36°; and, about 25°; and, has a thickness of at least one of: between 0.8 mm and 3 mm; about 2.6 mm.

In one embodiment each drive magnet is mounted on an annular rotor drive yoke.

In one embodiment the heart pump includes a common yoke that forms the rotor drive yoke and a rotor bearing yoke.

In one embodiment the rotor drive yoke has a thickness of at least one of: between 1 mm and 5 mm; and, between 1.5 mm and 2.5 mm; and, about 1.9 mm.

In one embodiment: the number of drive magnets is at least one of: 8; 10; 14; and, 16; and, the number of stator poles is at least one of: 12; 15; and, 18.

In one embodiment the drive includes 12 stator poles configured as at least one of: one three phase motors; and, two three phase motors.

In one embodiment the drive includes a number of coils connected using at least one of a delta configuration and a star configuration.

In one embodiment the drive and rotor are arranged such that, at least one of: a spacing between the first face of the rotor and the first end of the cavity is at least one of: between 2 mm and 5 mm in use; between 2 mm and 3 mm in use; and, approximately 2.3 mm in use; a spacing between a drive stator pole face and drive magnet face is at least one of: between 2.5 mm and 6 mm in use; between 2.5 mm and 4 mm in use; and, approximately 3.2 mm in use; a spacing between a drive stator yoke and drive magnet yoke is at least one of: between 7 mm and 25 mm in use; between 8 mm and 20 mm in use; and, approximately 17 mm in use; and, a spacing between a drive stator pole face and drive magnet yoke is at least one of: between 4 mm and 8 mm in use; between 4.5 mm and 7 mm in use; and, approximately 5.8 mm in use.

In one embodiment a spacing between the first face of the rotor and the first end of the cavity is at least one of: at least 2.3 mm in use; and, sufficient to accommodate axial movement of the impeller in use.

In one embodiment the vanes are mounted on the first face of the rotor between the first face of the rotor and the first end of the cavity and wherein the vanes have a height of at least one of: between 1.5 mm and 5 mm; between 1.5 mm and 2.5 mm; between 1.8 mm and 2.2 mm; about 2 mm.

In one embodiment each bearing stator leg has at least one of: a width of at least one of: between 2 mm and 4 mm; about 3.6 mm for the first bearing stator leg; and, about 2.9 mm for the second bearing stator leg; and, a length of at least one of: between 5 mm and 35 mm; and, about 14.8 mm.

In one embodiment the at least one bearing coil is wound on the first bearing stator leg.

In one embodiment at least one bearing stator leg is narrower than a corresponding magnetic bearing member at least proximate an end of the bearing stator leg.

In one embodiment at least one bearing stator leg tapers inwardly proximate an end of the bearing stator leg.

In one embodiment the tapering has at least one of: a height of at least one of: between 0 mm and 10 mm; and, about 5 mm; a width of at least one of: between 0 mm and 4 mm; and, between 0.5 mm and 2 mm.

In one embodiment the taper is at least one of: towards a centreline of magnetic bearing member; and, such that a radial restoring force from an individual bearing increases as the rotor is radially offset from a central radial position.

In one embodiment at least one of the first and second magnetic bearing members includes an annular permanent bearing magnet.

In one embodiment at least one of the first and second magnetic bearing members includes an annular iron member.

In one embodiment at least one of the first and second magnetic bearing members have at least one of: a thickness that is at least one of: between 1 mm and 3 mm; and, about 2.4 mm; and, a width that is at least one of: between 3 mm and 4.5 mm; about 2.5 mm; and, about 3.5 mm.

In one embodiment the first and second magnetic bearing members are provided on a common annular laminated or solid iron bearing rotor yoke.

In one embodiment the bearing rotor yoke has at least one of: a width that is at least one of: between 10 mm and 13 mm; and, about 11 mm; and, a thickness that is at least one of: between 1 mm and 5 mm; and, between 1.5 mm and 2.5 mm; and, about 1.9 mm.

In one embodiment at least one of the first and second magnetic bearing members tapers inwardly towards the second rotor face.

In one embodiment the taper is at least one of: towards a centreline of magnetic bearing member; and, such that a radial restoring force from an individual bearing increases as the rotor is radially offset from a central radial position.

In one embodiment at least one of the first and second magnetic bearing members includes a tapered iron shoe.

In one embodiment the second bearing stator leg is tapered and the second magnetic bearing member includes a permanent magnet.

In one embodiment the first bearing stator leg is substantially untapered and the first bearing magnetic member is an annular iron member.

In one embodiment the first bearing stator leg is tapered and the first bearing magnetic member is an annular permanent magnet.

In one embodiment the heart pump provides at least partial left ventricular function.

In one embodiment the heart pump provides at least partial right ventricular function.

In one embodiment the impeller includes first and second sets of vanes provided on a rotor body, the rotor being positioned within the cavity to define: a first cavity portion having a first inlet and a first outlet, the first set of vanes being provided within the first cavity portion so as to define a first pump that provides at least partial left ventricular function; and, a second cavity portion having a second inlet and a second outlet, the second set of vanes being provided within the second cavity portion so as to define a second pump that provides at least partial right ventricular function.

In one embodiment the heart pump is a total artificial heart.

In one embodiment the axial position of the impeller determines a separation between each set of vanes and a respective cavity surface, the separation being used to control the fluid flows from the inlets to the outlets.

In one embodiment the impeller and housing cooperate to define a hydrodynamic bearing in the event that the magnetic bearing fails.

In one embodiment the hydrodynamic bearing is defined at least in part by an upper surface of at least some of the vanes of the impeller.

In one embodiment the hydrodynamic bearing is defined by an upper surface of vanes of the impeller facing the first end of the cavity.

In one embodiment the upper surface includes a leading ramp and a trailing flat pad.

In one embodiment at least one of: the flat pad has an inner radius of at least one of: between 16 mm and 22 mm; and, between 18 mm and 20 mm; the flat pad has a length of at least one of: between 1 mm and 5 mm; between 2 mm and 4 mm; and, about 3 mm; the ramp has a length of at least one of: between 5 mm and 15 mm; between 8 mm and 12 mm; and, about 10 mm; and, the ramp has a height of at least one of: between 0.02 mm and 0.1 mm; between 0.04 mm and 0.08 mm; and, about 0.06 mm.

In one embodiment the vane at least one of: has an inner radius that is at least one of: between 10 mm and 20 mm; between 12 mm and 18 mm, between 14 mm and 16 mm; and, about 15 mm; an outer radius that is at least one of: between 20 mm and 30 mm; between 22 mm and 28 mm; between 24 mm and 26 mm; and, about 25 mm.

In one embodiment the heart pump includes a controller that controls operation of the drive and bearing in use.

In one embodiment the controller includes a processor operating in accordance with software instructions stored in a memory.

In one embodiment the controller controls the drive to selectively generate an axial attractive force.

In one embodiment the controller controls the drive to generate the axial attractive force to at least one of: move the impeller within the cavity; and, increase shock resistance when operating using a hydrodynamic bearing in the event that the magnetic bearing fails.

In one embodiment the controller: detects at least one of: failure of the magnetic bearing;

and, movement of the impeller to the second end of the cavity when the magnetic bearing has failed; and, controls the drive to generate the axial attractive force in response to the detection.

In one embodiment the controller detects failure of the magnetic bearing based on at least one of: a bearing indicator indicative of a current used by the magnetic bearing; a drive indicator indicative of a current used by the drive; and, sensor signals.

In one embodiment the heart pump has an axial system stiffness of at least one of: at least 10 N/mm; at least 20 N/mm; at least 30 N/mm; less than 60 N/mm; less than 50 N/mm; about 10-60 N/mm; about 25-50 N/mm; about 15-25 N/mm; about 30-40 N/mm; and, about 35-40 N/mm.

In one embodiment the heart pump has a radial system stiffness of at least one of: between 0.5 N/mm and 11 N/mm; between 0.5 N/mm and 1.5 N/mm; between 1.5 N/mm and 3.0 N/mm;

between 3 N/mm and 6 N/mm; and, between 6 N/mm and 11 N/mm.

In one broad form an aspect of the present invention seeks to provide a heart pump including: a housing defining a cavity including: at least one inlet aligned with an axis of the cavity; and, at least one outlet provided in a circumferential outer wall of the cavity; an impeller provided within the cavity, the impeller including a rotor and vanes mounted on the rotor for urging fluid from the inlet radially outwardly to the outlet; a drive for rotating the impeller in the cavity, the drive including: a plurality of circumferentially spaced permanent drive magnets mounted within and proximate a first face of the rotor; and, a plurality of circumferentially spaced drive coils mounted within the housing proximate a first end of the cavity, each coil being wound on a respective drive stator pole of a drive stator and being substantially radially aligned with the drive magnets, the drive coils being configured to generate a drive magnetic field that cooperates with the drive magnets to thereby rotate the impeller.

In one embodiment, the heart pump further includes a bearing for supporting the impeller within the cavity, the bearing being at least one of: a magnetic bearing; a hydrodynamic bearing; and, a physical bearing.

In one broad form an aspect of the present invention seeks to provide a heart pump including: a housing defining a cavity including: at least one inlet aligned with an axis of the cavity; and, at least one outlet provided in a circumferential outer wall of the cavity; an impeller provided within the cavity, the impeller including a rotor and vanes mounted on the rotor for urging fluid from the inlet radially outwardly to the outlet; and, a magnetic bearing including: first and second annular magnetic bearing members mounted within and proximate a second face of the rotor, the first magnetic bearing member being provided radially outwardly of the second magnetic bearing member; a number of circumferentially spaced substantially U-shaped bearing stators mounted in the housing proximate a second end of the cavity, each U-shaped bearing stator having first and second bearing stator legs that interact with the first and second magnetic bearing members respectively; and, at least one bearing coil on each bearing stator that generates a magnetic field that cooperates with the magnetic bearing members to thereby at least one of: control an axial position of the impeller; and, at least partially restrain radial movement of the impeller.

In one broad form an aspect of the present invention seeks to provide a heart pump including: a housing defining a cavity including: at least one inlet aligned with an axis of the cavity; and, at least one outlet provided in a circumferential outer wall of the cavity; an impeller provided within the cavity, the impeller including a rotor and vanes mounted on the rotor for urging fluid from the inlet radially outwardly to the outlet; a drive for rotating the impeller in the cavity, the drive including: a plurality of circumferentially spaced permanent drive magnets mounted within and proximate a first face of the rotor; and, a plurality of circumferentially spaced drive coils mounted within the housing proximate a first end of the cavity, and wherein vanes of the impeller and the first end of the housing cooperate to define a hydrodynamic bearing.

In one embodiment the hydrodynamic bearing is defined by an upper surface of the vanes of the impeller facing the first end of the cavity.

In one embodiment the upper surface includes a leading ramp and a trailing flat pad.

In one embodiment at least one of: the flat pad has an inner radius of at least one of: between 16 mm and 22 mm; and, between 18 mm and 20 mm; the flat pad has a length of at least one of: between 1 mm and 5 mm; between 2 mm and 4 mm; and, about 3 mm; the ramp has a length of at least one of: between 5 mm and 15 mm; between 8 mm and 12 mm; and, about 10 mm; and, the ramp has a height of at least one of: between 0.02 mm and 0.1 mm; between 0.04 mm and 0.08 mm; and, about 0.06 mm.

In one embodiment the vane at least one of: has an inner radius that is at least one of: between 10 mm and 20 mm; between 12 mm and 18 mm, between 14 mm and 16 mm; and, about 15 mm; an outer radius that is at least one of: between 20 mm and 30 mm; between 22 mm and 28 mm; between 24 mm and 26 mm; and, about 25 mm.

In one embodiment the heart pump includes a magnetic bearing to at least one of control an axial position of the impeller and at least partially restrain radial movement of the impeller, and wherein the hydrodynamic bearing is configured to operate if the magnetic bearing fails.

In one embodiment the heart pump includes a controller that controls operation of the drive and bearing in use.

In one embodiment the controller includes a processor operating in accordance with software instructions stored in a memory.

In one embodiment the controller controls the drive to selectively generate an axial attractive force.

In one embodiment the controller controls the drive to generate the axial attractive force to at least one of: move the impeller within the cavity; and, increase shock resistance when operating using a hydrodynamic bearing in the event that the magnetic bearing fails.

In one embodiment the controller: detects at least one of: failure of the magnetic bearing; and, movement of the impeller to the second end of the cavity when the magnetic bearing has failed; and, controls the drive to generate the axial attractive force in response to the detection.

In one embodiment the controller detects failure of the magnetic bearing based on at least one of: a bearing indicator indicative of a current used by the magnetic bearing; a drive indicator indicative of a current used by the drive; and, sensor signals.

It will be appreciated that the broad forms of the invention and their respective features can be used in conjunction and/or independently, and reference to separate broad forms in not intended to be limiting.

BRIEF DESCRIPTION OF THE DRAWINGS

Various examples and embodiments of the present invention will now be described with reference to the accompanying drawings, in which:

FIG. 5A is a schematic plan view of an example of a drive illustrating a first slot width;

FIG. 5B is a schematic plan view of an example of a drive illustrating a second slot width;

FIG. 5C is a graph illustrating an example of drive motor constant and axial force with changing slot width;

FIG. 6D is a graph illustrating an example of different speed and torque limits with different winding configurations;

FIG. 22A is a graph illustrating an example of a magnetic bearing target current during a levitation fault sequence;

FIG. 22B is a graph showing an example of a magnetic bearing target position during a levitation fault sequence;

FIG. 22C is a graph showing an example of a drive speed during a levitation fault sequence;

FIG. 22D is a graph showing an example of a drive target current during a levitation fault sequence;

DETAILED DESCRIPTION OF THE PREFERRED EMBODIMENTS

Figure 1A:
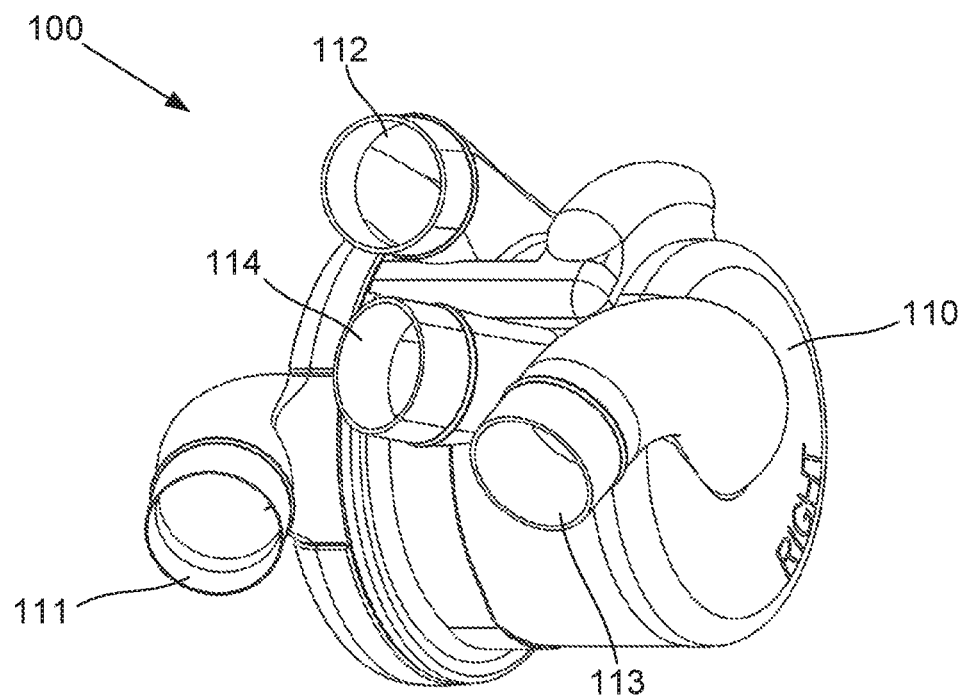
FIG. 1A is a schematic perspective view of an example of a heart pump.

An example of a heart pump will now be described with reference to FIGS. 1A to 1D, FIGS. 2A to 2I and FIGS. 3A to 3E.

In this example the heart pump is a biventricular device which can operate either as a ventricular assist device to assist function of left and right ventricles of a subject's heart, or alternatively as a total artificial heart. It will be appreciated however that whilst reference is made to a biventricular device this is not essential, and alternatively the principles described herein can equally be applied to single ventricular assist devices or any other form of blood pump.

In this example, the heart pump 100 includes a housing 110 forming a cavity. The housing can be of any suitable form but typically includes a main body 110.1, left and right end caps 110.2, 110.3 which connect to the main body 110.1, as well as an end plate 110.4 positioned between the main body 110.1 and left end cap 110.2. The housing can be made of any suitable biocompatible material, and can be made of titanium, a polymer or the like.

The housing 110 includes two inlets 111, 113, for connection to the left atrium/pulmonary vein and right atrium/vena cava, or left and right ventricles, and two outlets 112, 114 for connection to the aorta and pulmonary artery, respectively. Whilst two inlets and outlets are shown, it will be appreciated that this is in the context of a biventricular device, and that a single inlet and outlet can be used for a single ventricular device.

The heart pump 100 includes an impeller 120 provided within the cavity. The impeller 120 includes a rotor 121 having vanes mounted thereon for urging fluid from the inlet to the outlet upon rotation of the impeller 120. In this example, as the heart pump 100 is a biventricular device, the impeller includes two sets of vanes 122, 123 each of which is used for urging fluid from a respective inlet 111, 113 to a respective outlet 112, 114. In this example, the rotor 121 is positioned within the cavity to effectively divide the cavity into first and second cavity portions, each having a respective inlet and outlet, thereby allowing each to function as a respective pump.

Figure 1B:
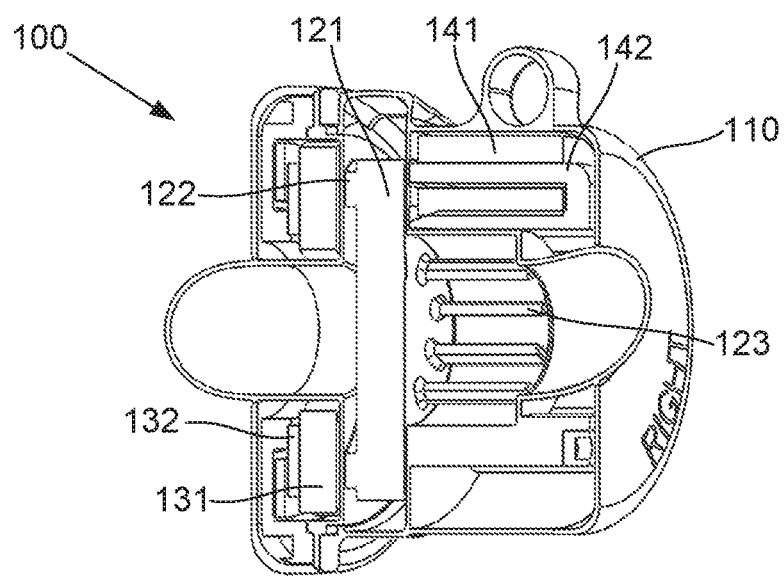
FIG. 1B is a schematic cutaway view of the heart pump of FIG. 1A.
Figure 1C:
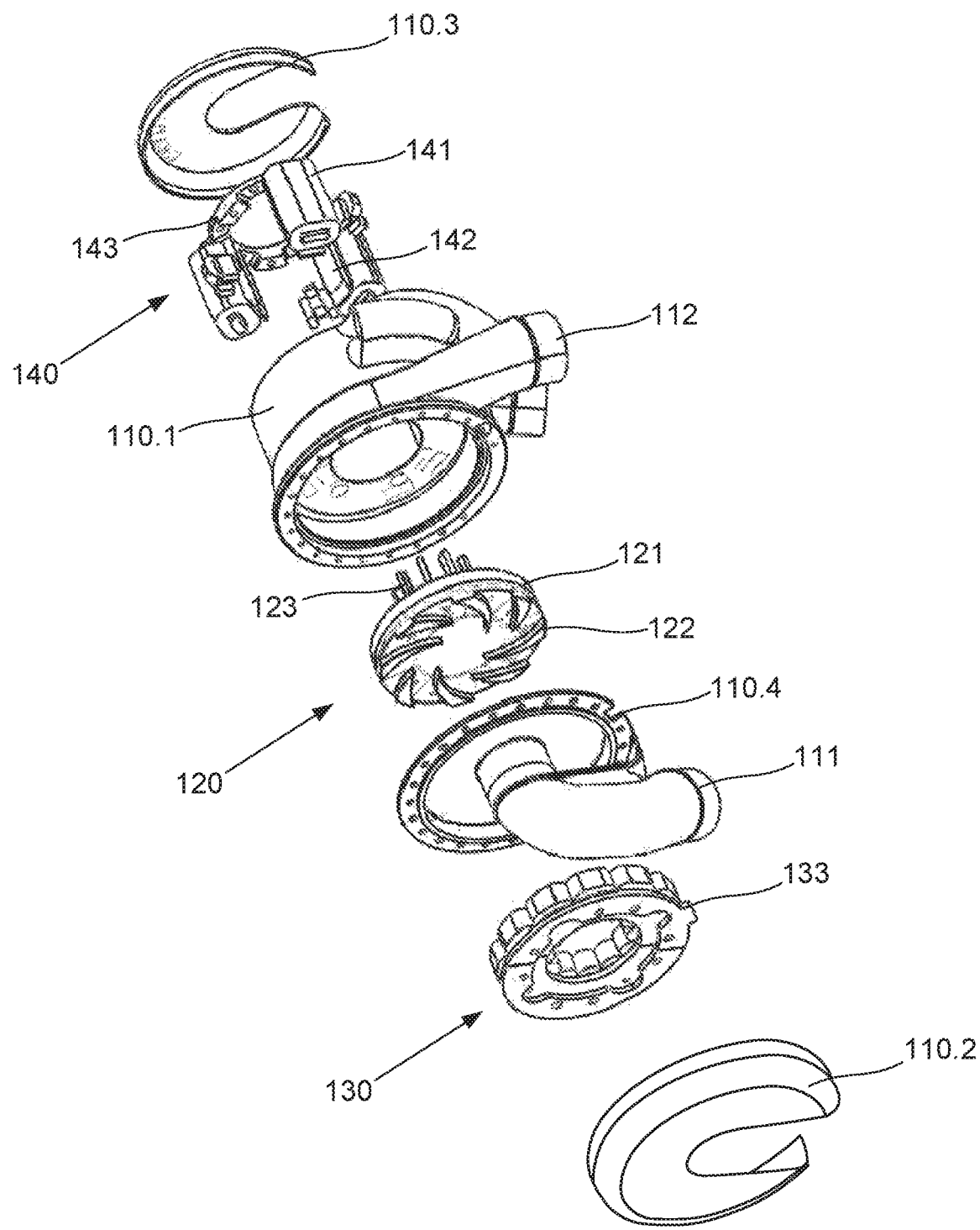
FIG. 1C is a schematic perspective exploded view of the heart pump of FIG. 1A.

Thus, in the current example, the vanes 122 are used to urge fluid from the inlet 111 to the outlet 112, with this being provided on the left-hand side of the pump in the orientation shown in FIG. 1B, and operating to provide left-ventricular function, whilst the vanes 123 urge fluid from the inlet 113 to the outlet 114 and act to provide right-ventricular function. In this context the first and second cavity portions are generally referred to as left and right cavities, and in conjunction with the impeller 120 provide left and right pumps, respectively. It will be appreciated that in this regard, the terms left and right refer to the intended ventricular function of the cavities as opposed to the particular orientation of the pump in the Figures, which is used for illustrative purposes only.

As shown in FIGS. 3A to 3E, the vanes 122, 123 have different profiles, which provide different flow characteristics for the left and right hand pumps, as will be described in more detail below. In particular, in this example, the left hand vanes 122 are typically flared outwardly, thickening towards an outer circumferential edge of the rotor 121, as well as being swept so as to be angled away from a direction of rotation of the impeller, as shown by the arrow R. However, this is not always the case, and for example, for an LVAD the left hand vanes are radially straight and thin, similar to the right sided vanes described below. In contrast, the right hand vanes 123 are generally straight and of a constant thickness, extending radially towards, but without meeting, an edge of the rotor perpendicularly. The impact on these arrangements and the particular dimensions of the vanes 122, 123 and rotor 121 will be described in more detail below.

The heart pump 100 further includes a drive 130 that rotates the impeller 120 within the cavity and a magnetic bearing 140 that controls an axial position of the impeller 120 within the cavity. The apparatus further includes a controller 150 which, in use, is coupled to a sensor 160 and drive and bearing signal generators 137, 147, which are in turn coupled to drive and bearing coils 131, 141 of the drive and bearing 130, 140. The sensor 160 is used to sense an axial position of the impeller 120 within the cavity, and can be of any appropriate form, as will be described in more detail below.

In use, the controller 150 uses signals from the sensor 160 and optionally other sensors, together with appropriate control algorithms, allowing operation of the bearing 140 and optionally the drive 130 to be controlled. In particular, the controller 150 is adapted to monitor signals from the position sensor 160 and other sensors, then control the current supplied to the drive coils 131, by the signal generator 137, to control rotation of the impeller and to the bearing coils 141, by the signal generator 147, to control the axial position of the impeller 120. Thus, the impeller 120 is acted upon by the fluid pressures in the housing 110, which create a net hydraulic force on the impeller 120. Forces acting on the impeller 120 are compensated for by the magnetic bearing, with the controller 150 operating to control the amount of current supplied to the electromagnets in the bearing to thereby maintain the position of the impeller 120. As such, the current used by the magnetic bearing system has a direct correlation to the forces and pressures acting on the impeller 120. In this manner, changes to the inlet and outlet pressures can be detected through the magnetic bearing signals in real-time.

The controller 150 can also be adapted to provide speed control functionality, altering the rotational speed of the impeller, for example depending on factors such as fluid pressures within the pump.

The controller 150 can be of any suitable form but typically includes an electronic processing device 151, an optional memory 152, and an interface 154 for connecting to the heart pump, each of which are interconnected by a bus 155, or other similar arrangement. The electronic processing device can be any form of electronic processing device capable of interpreting signals and causing the drive and bearing to be controlled, such as a microprocessor, microchip processor, logic gate configuration, firmware optionally associated with implementing logic such as an FPGA (Field Programmable Gate Array), or any other electronic device, system or arrangement.

The controller can also implement separate control functionality, for example separate modules, to thereby control the bearing and drive.

An optional external interface 153 may be provided allowing for interaction with the controller 150. In the event that the controller is positioned outside the body this can include an I/O device 153 such as a touch screen or the like, whereas if positioned inside the body this would typically be in the form of a wireless communications module allowing communication with an external control device.

The above described heart pump is an example of a heart pump that can operate as a bi-ventricular assist device, providing ventricular assistance to the left and right ventricles, or can act as a total artificial heart, allowing functionality of the left and right ventricles to be replaced completely. Similar arrangements can also be provided corresponding to the left or right side pumps only, to thereby provide left or right ventricular assist devices.

Further details of the drive and bearing will now be described.

In one example, the drive includes a plurality of circumferentially spaced permanent drive magnets 134 mounted within and proximate a first face of the rotor 121. Adjacent drive magnets typically have opposing polarities, although other arrangements could be used, such as if one drive magnet is split in two and placed next to another, than a similar function can be achieved. The drive 130 also includes a plurality of circumferentially spaced drive coils 131 mounted within the housing 110 proximate a first end of the cavity, each coil 131 being wound on a respective drive stator pole 132.1 of a drive stator core 132 and being substantially radially aligned with the drive magnets 134.

In use the drive coils 131 are configured to generate a drive magnetic field, through application of appropriate currents, which cooperates with the drive magnets 134 to thereby rotate the impeller 120 within the cavity.

A specific example drive magnet configuration is shown in more detail in FIGS. 2A to 2C and 4A and 4B and 5A and 5B. In this example, the drive coils 131 and drive stator poles 132.1 are wedge, triangular or trapezoidally shaped, circumferentially spaced and extend axially from an annular drive yoke 132.2, which is in turn coupled to a mounting/PCB (printed circuit board) 133, allowing the drive stator core 132 to be fixed within the housing 110. The drive stator core 132 is typically formed from a soft composite iron core, although other suitable materials can be used. The drive magnets 134 are arcuate shaped rare earth magnets, circumferentially spaced proximate an outer circumferential edge of the rotor and proximate a face of the rotor facing the drive coils 131, the drive magnets being mounted on a soft iron rotor drive yoke 135.

In this example, the drive stator and drive coils define twelve electromagnets axially aligned with the drive magnets 134 in the rotor 121, to thereby maximise a degree of magnetic coupling between the magnets in the rotor 121 and the drive 130, however, it will be apparent from the following description that other configurations can be used.

Turning now to the magnetic bearing 140, this typically includes first and second annular magnetic bearing members 144, 145 mounted within and proximate a face of the rotor facing the bearing coils 141, the first magnetic bearing member 144 being provided radially outwardly of the second magnetic bearing member 145. The magnetic bearing members 144, 145 can be mounted to and/or integrally formed with a rotor bearing yoke 146 extending between the magnetic bearing members 144, 145. The bearing rotor yoke can be made of laminated iron sheets to reduce eddy currents within the yoke.

Figure 3A:
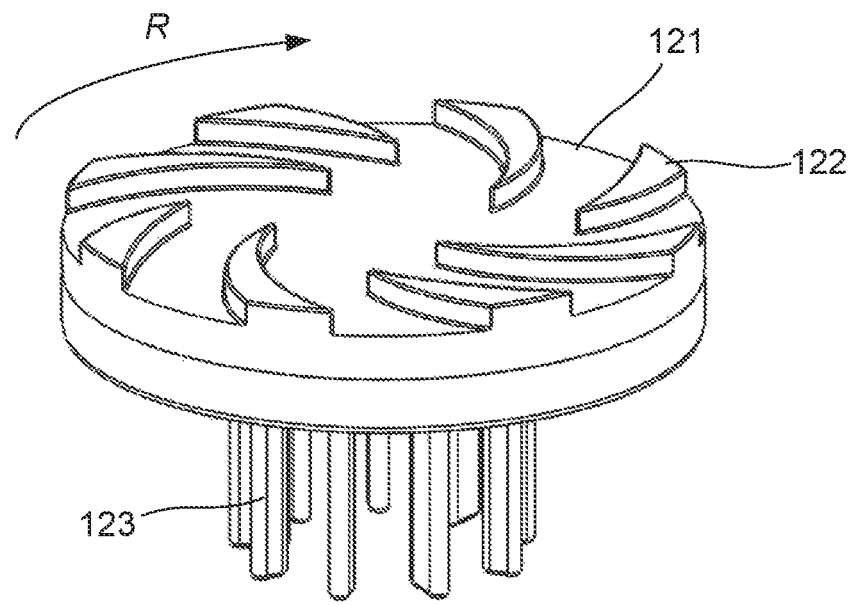
FIG. 3A is a schematic perspective view of an example impeller from the left pump side.
Figure 3B:
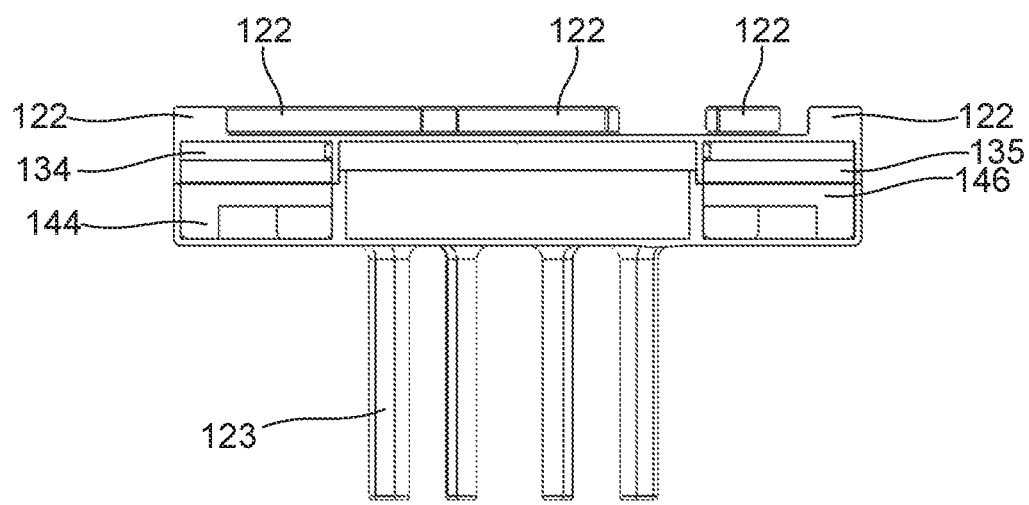
FIG. 3B is a schematic cut through view of the impeller of FIG. 3A.
Figure 3C:
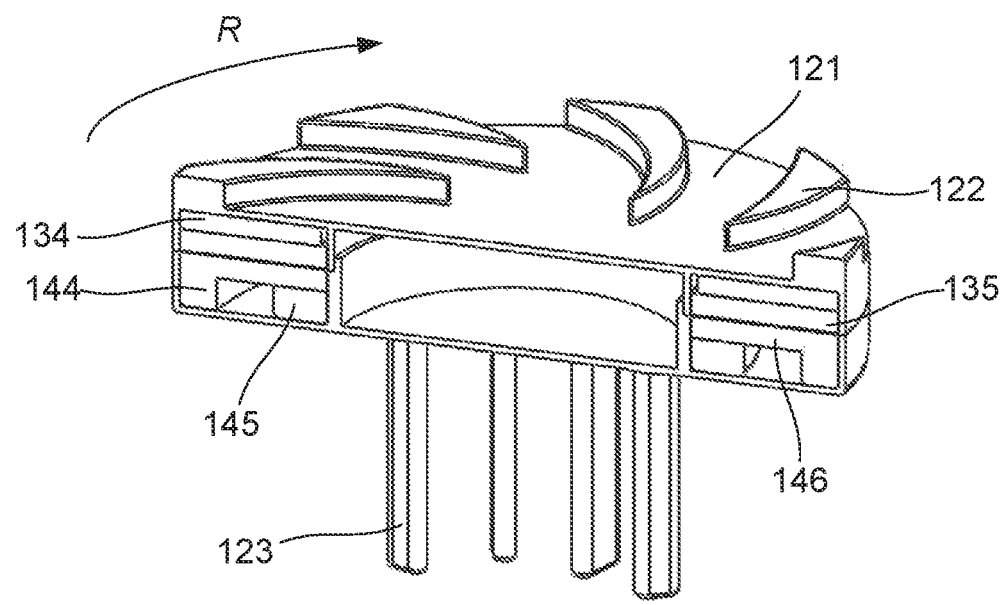
FIG. 3C is a schematic perspective cut through view of the impeller of FIG. 3A.
Figure 3D:
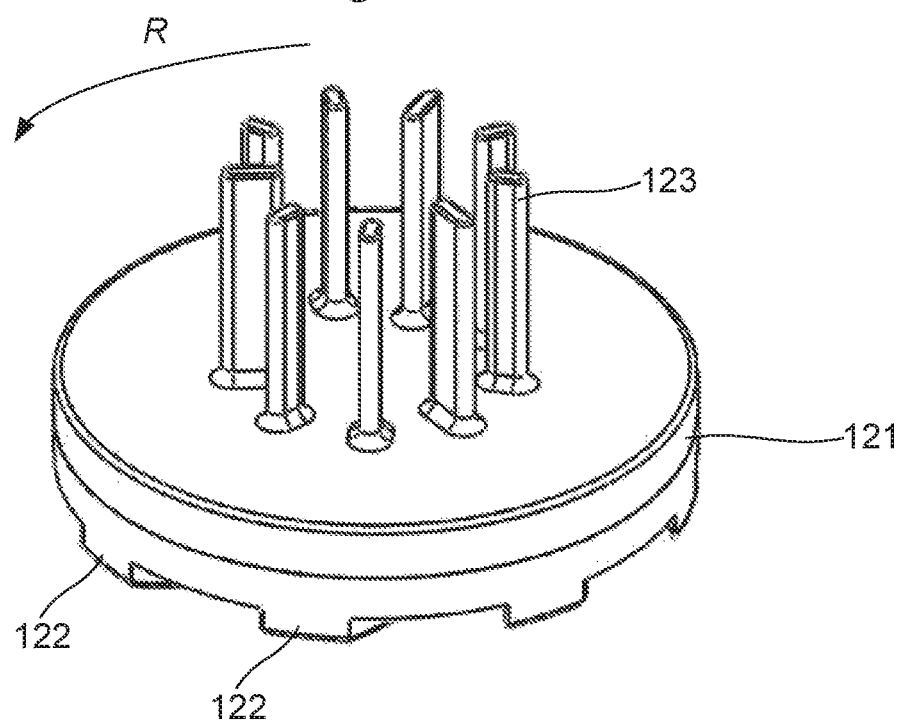
FIG. 3D is a schematic perspective view of the impeller of FIG. 3A from the right pump side.
Figure 3E:
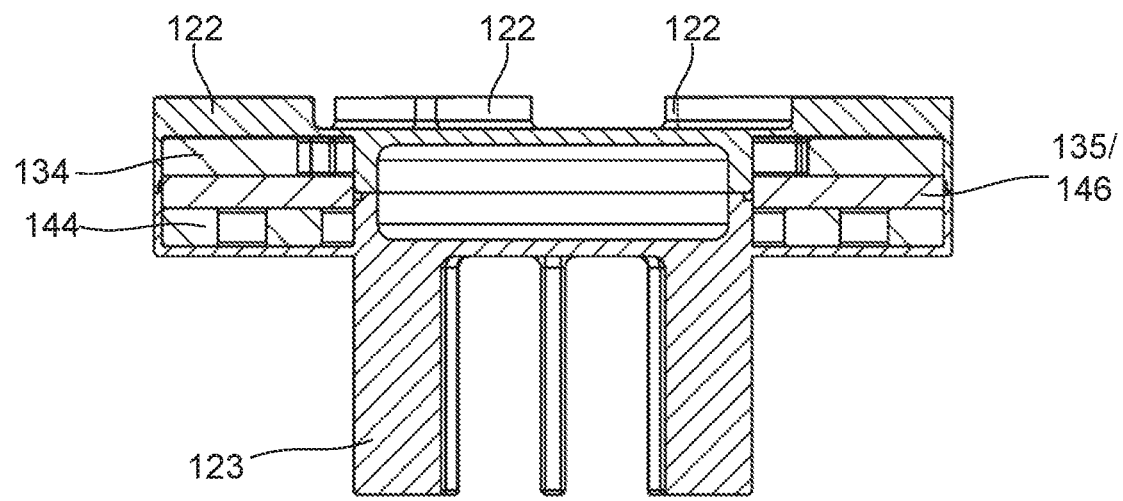
FIG. 3E is a schematic cut through view of an alternative example of the impeller of FIG. 3A.

As further shown in the example of FIG. 3E, the rotor drive yoke 135 and rotor bearing yoke 146 can be formed from a common yoke 135/146.

A number of circumferentially spaced substantially U-shaped bearing stators 142 are mounted in the housing 110 proximate a second end of the cavity, each U-shaped bearing stator 142 having first and second bearing stator legs 142.1, 142.2 that interact with the first and second magnetic bearing members 144, 145 respectively. At least one bearing coil 141 is provided on each bearing stator 142 that generates a magnetic field that cooperates with the magnetic bearing members 145, 144 to thereby control an axial position of the impeller 120 and at least partially restrain radial movement of the impeller 120.

In one example, the first and second bearing stator legs are substantially magnetically aligned with and/or geometrically radially aligned with, the first and second magnetic bearing members respectively. This can be performed so that the first and second bearing stator cooperate with the first and second magnetic bearing members respectively so that a radial force from an individual bearing is about between 0 N-2N when the bearing stator legs are substantially aligned with the magnetic bearing members. Whilst alignment can reduce cross coupling, some misalignment might be beneficial for symmetrical radial restoration and generating changes in radial force with axial position. Accordingly, in some examples, the either or both of the first and second bearing stator legs can be radially offset from a respect one of first and second magnetic bearing members by a small distance, such as at least one of: less than 1 mm, less than 0.5 mm and less than 0.2 mm.

In one particular example, shown in more detail in FIGS. 2D to 2I, the magnetic bearing includes three bearing coils 141, each of which is mounted on a first bearing stator leg 142.1 of respective U-shaped bearing stators 142, with a second bearing stator leg 142.2 being positioned radially inwardly of the first bearing stator leg 142.1. The bearing stators 142 are mounted to a bearing stator support 143 and circumferentially spaced 120° apart around the housing so that the first and second bearing stator legs 142.1, 142.2 align with respective magnetic material members 144, 145, allowing an axial position of the impeller 120 to be controlled.

Typically, the magnetic bearing 140 includes permanent magnets, which may be either part of the magnet magnetic bearing members 144, 145 or attached to one or both of the bearing stator legs. For example, this can include circumferentially spaced first and second permanent bearing magnets 144, 145. Alternatively, the magnetic bearing members can include a ferromagnetic material member 144 and a permanent magnet 145, or just ferromagnetic material, with permanent magnets being coupled to the stator bearing legs 142.1, 142.2 of the stators 142.

Figure 1D:
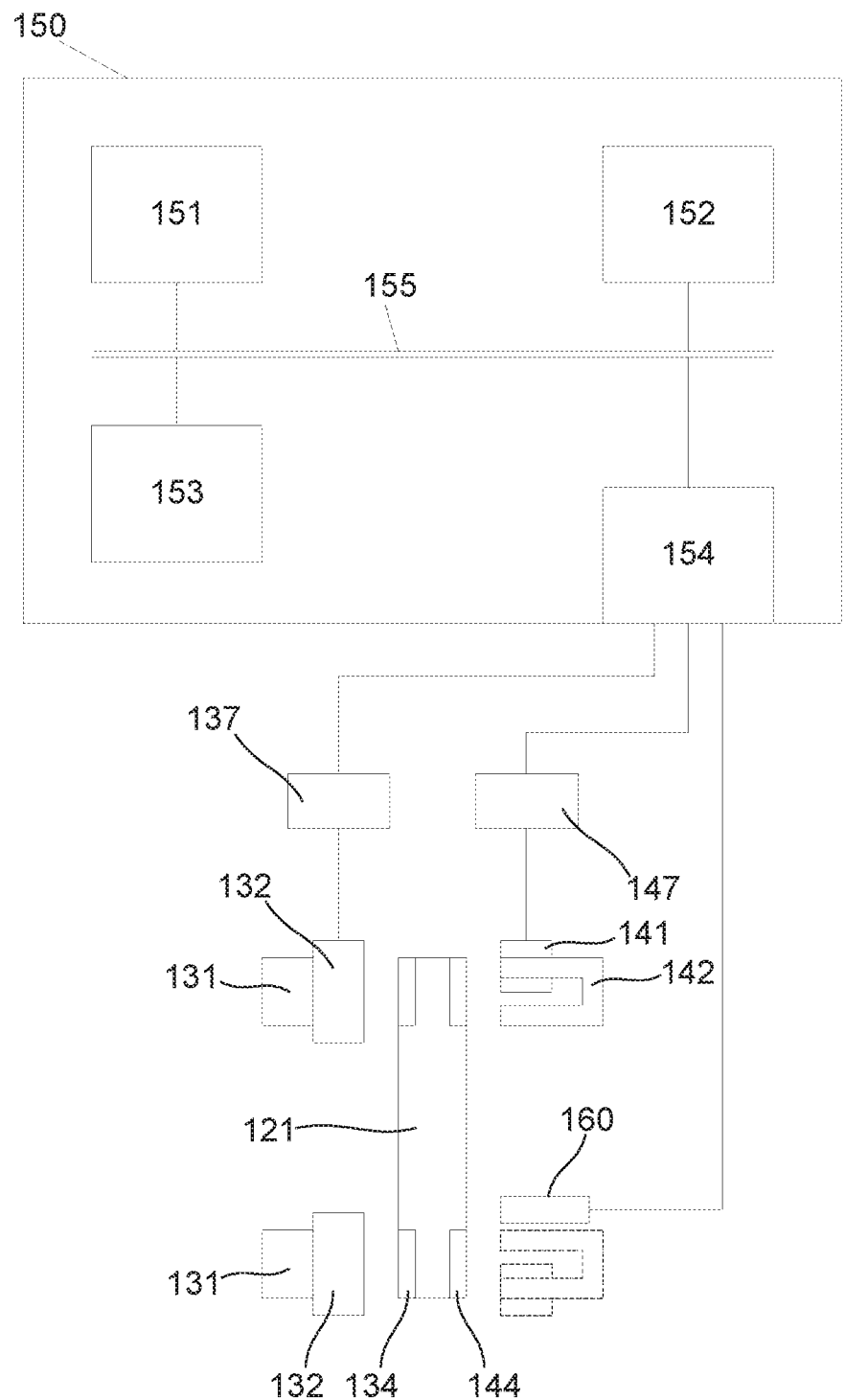
FIG. 1D is a schematic diagram of an example of a control system for the heart pump of FIG. 1A.
Figure 2A:
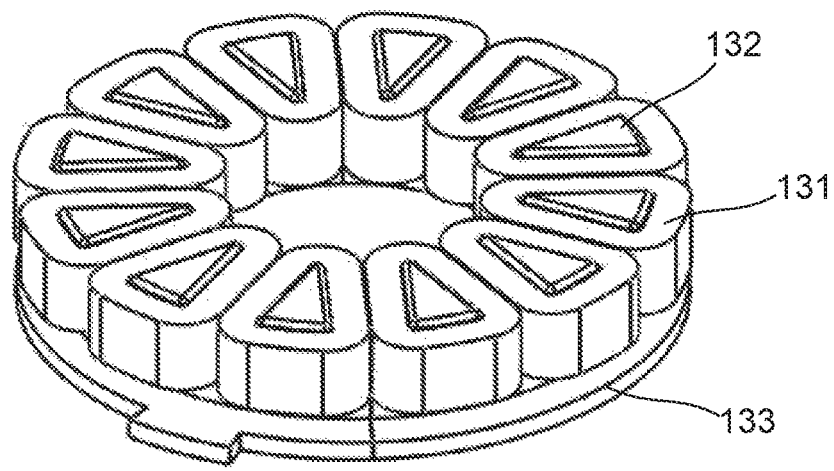
FIG. 2A is a schematic perspective top side view of an example of a drive magnet configuration.
Figure 2B:
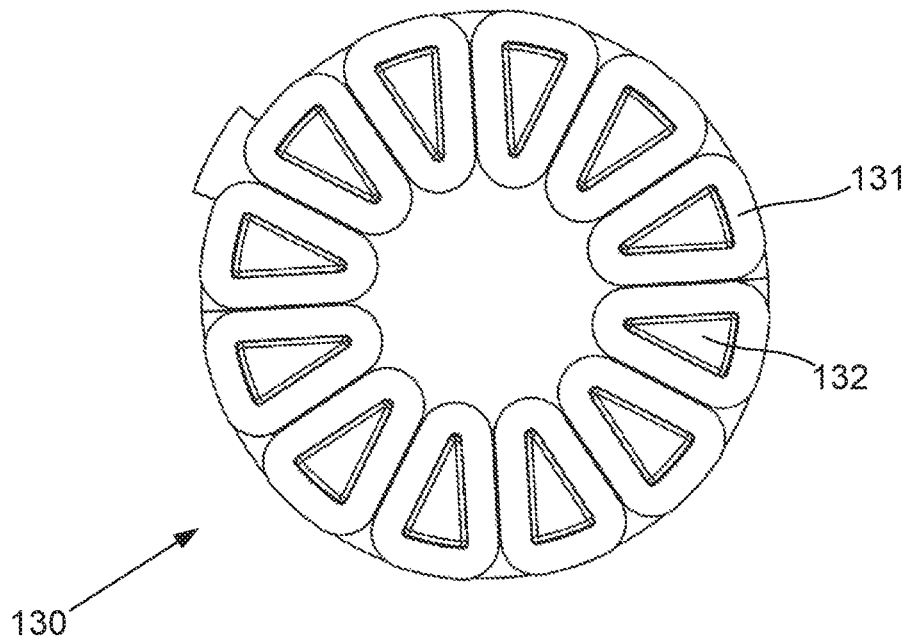
FIG. 2B is a schematic plan view of the drive magnet configuration of FIG. 2A.
Figure 2C:
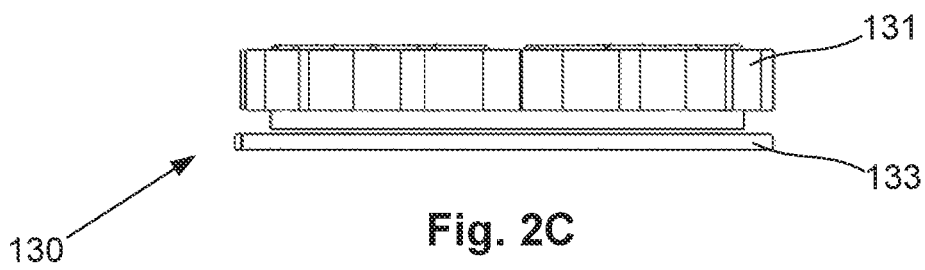
FIG. 2C is a schematic side view of the drive magnet configuration of FIG. 2A.
Figure 2D:
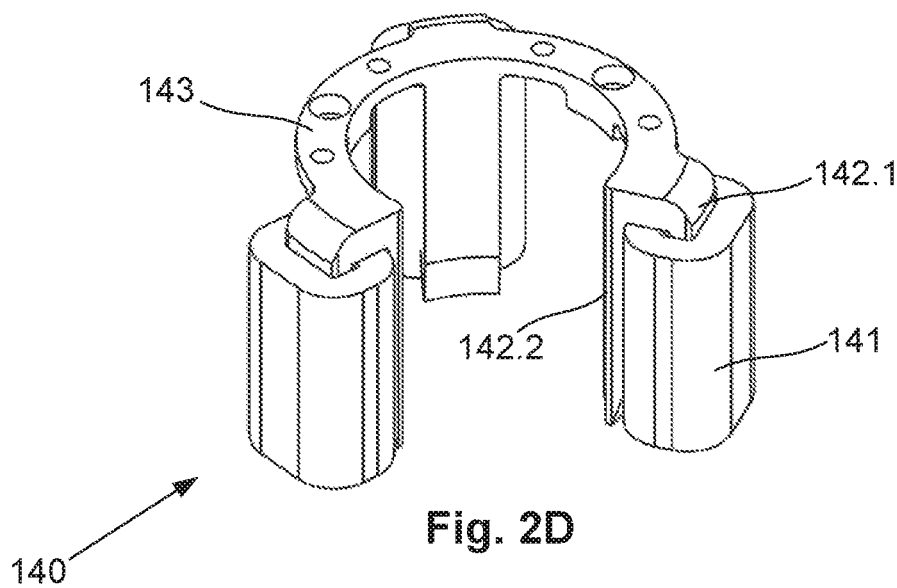
FIG. 2D is a schematic perspective top side view of a bearing magnet configuration.
Figure 2E:
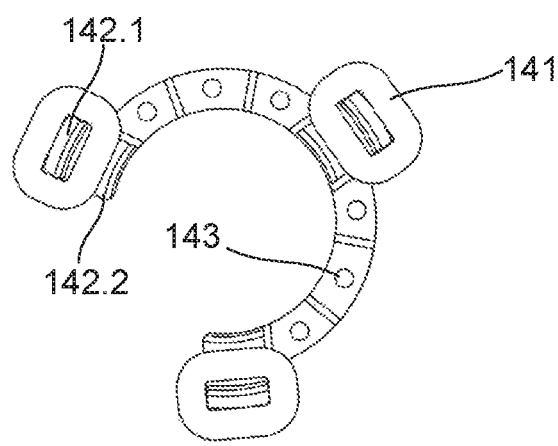
FIG. 2E is a schematic underside view of the bearing magnet configuration of FIG. 2D.
Figure 2F:
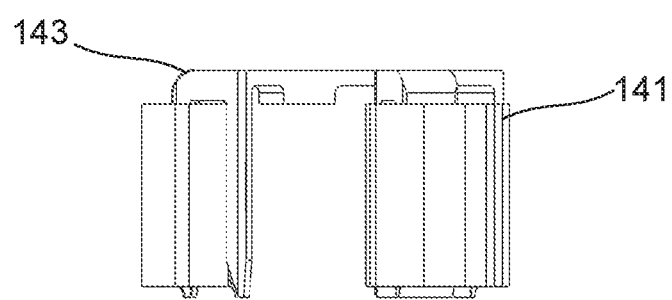
FIG. 2F is a schematic side view of the bearing magnet configuration of FIG. 2D.
Figure 2G:
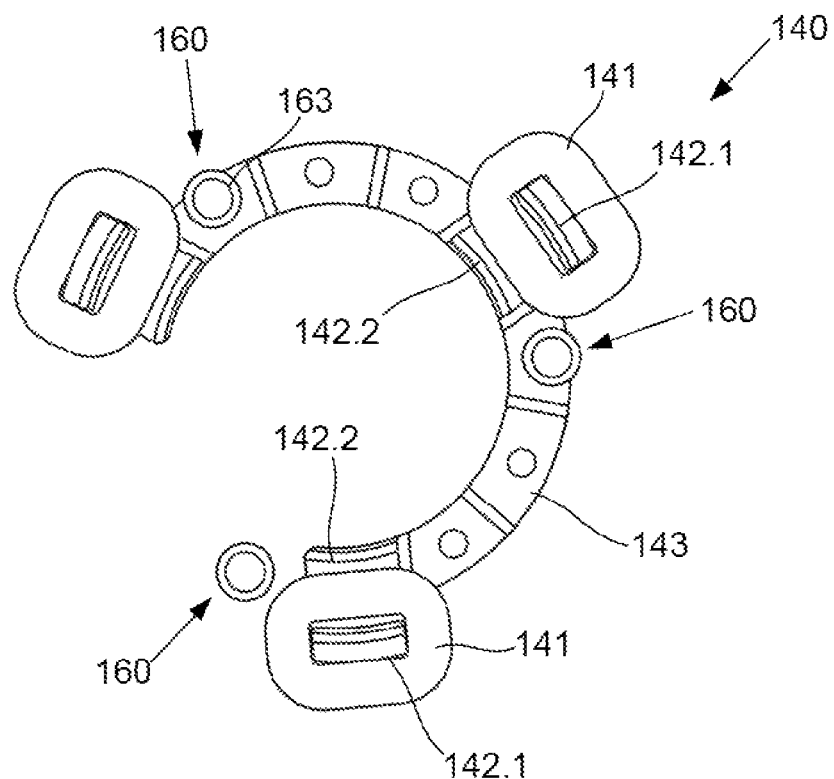
FIG. 2G is a schematic underside view of the bearing magnet arrangement of FIG. 2D with an eddy current sensor.
Figure 2H:
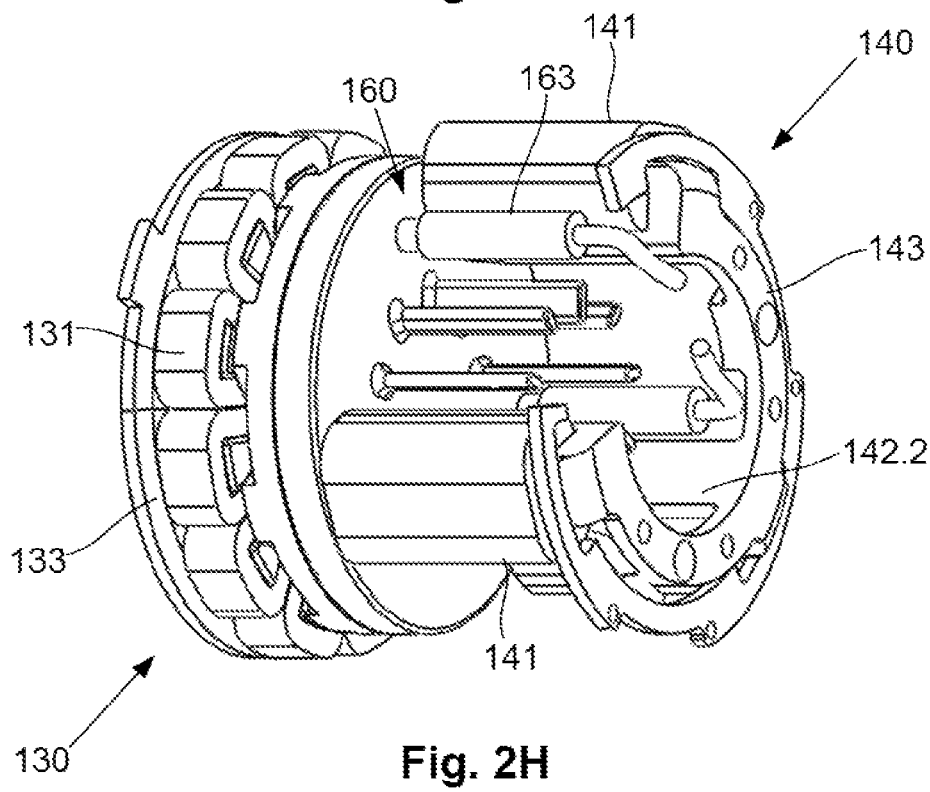
FIG. 2H is a schematic perspective top side view of the bearing and drive magnet configurations of FIGS. 2A and 2D together with the eddy current sensor.
Figure 2L:
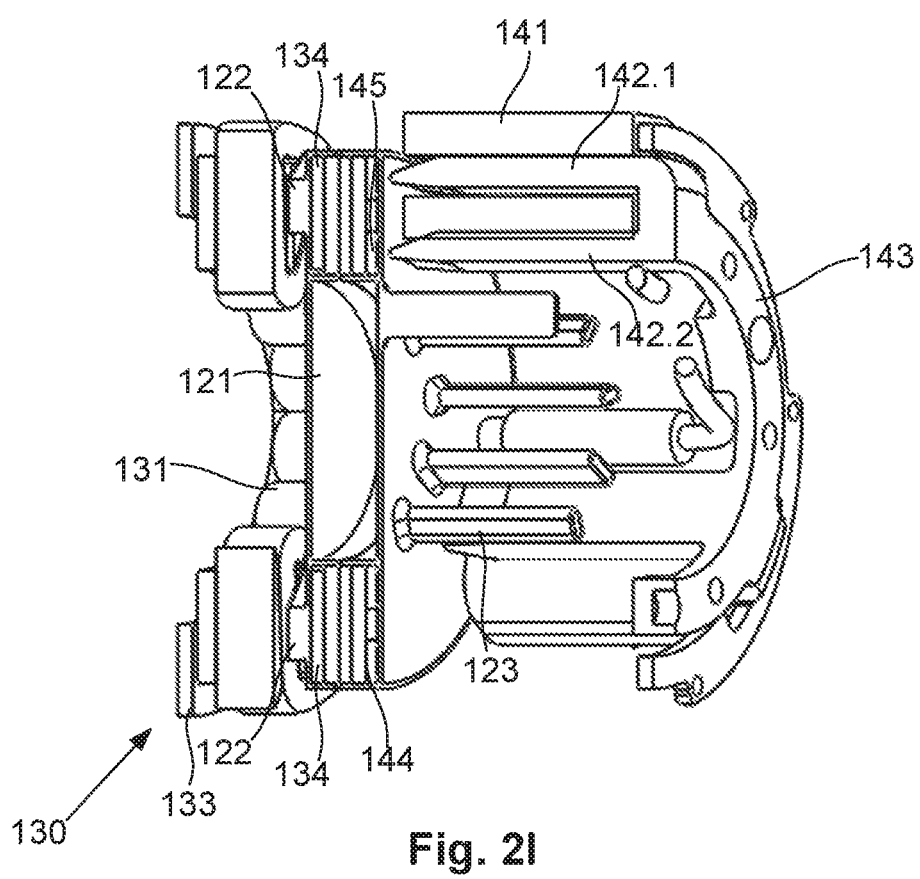
FIG. 2I is a schematic perspective cutaway view of the arrangement of FIG. 2H.

The drive 130 and magnetic bearing 140 are mounted at opposing ends of the housing 110 so that the drive and bearing 130, 140 are provided proximate opposing surfaces of the rotor 121 as shown for example in FIG. 1D, and FIGS. 2H and 2I. In the current example the drive 130 is mounted adjacent the left pump, whilst the bearing 140 is mounted adjacent the right pump, although the opposite configuration is contemplated. The depicted arrangement has a number of benefits.

Firstly, the inherent attractive magnetic forces between the drive and rotor and the bearing and rotor can be configured to substantially balance when the rotor is provided at a balance point at a normal operating speed, which may for example by approximately at a center of the cavity under conditions of normal flow, but can be either closer to the left or right side of the cavity.

For example, this arrangement can be configured so that the magnetic forces inherent between the drive 130 and impeller 120, and between the magnetic bearing 140 and impeller 120 are matched at an impeller balance position within the cavity, which corresponds to a desired position of the impeller under conditions of normal flow. This minimises the bearing current required to maintain the position of the impeller 120 within the cavity, hence reducing the amount power required to operate, and in particular drive and axially position the impeller.

Additionally, as well as having the magnetic forces balance, the forces generated by the drive and bearing can also be configured to provide a desired degree of axial and radial stiffness. In this regard, the stiffness is a measure of the deflection of the impeller 120 from a balance position in response to an external force. In one example, it is desirable to maximise the radial stiffness so as to maintain the impeller radially centralised within the cavity and to stop the impeller touching the inner circumferential wall of the cavity. Conversely, as the axial position of the impeller 120 can be used for flow control, and in particular to allow for passive and/or active response to changes in hemodynamic parameters, a low degree of axial stiffness is preferred. Accordingly, the passive magnetic forces can be configured to assist in meeting these requirements, as will be described in more detail below.

A further benefit of the above described arrangement, in the context of BiVAD/TAH applications, is that it allows the greater size of the magnetic bearing to be accommodated by the smaller size of the right pump cavity. In particular, this allows a gap between a bearing stator and bearing magnets to be minimized, as no vanes are located in this gap (as opposed to the left side where vanes are located in the magnetic airgap between the drive and the rotor), as will be described in more detail below. However, it will be appreciated that this limits an outer diameter of the right pump and thus achievable pressure generation at a given rotational speed, although for right pumps this is generally not an issue given their lower output or pressure requirements than the left pump.

A number of features of each of the drive and the bearing will now be described.

Drive Design

The drive is designed to minimise the required physical volume and weight of the drive stator, which is important in ensuring the resulting heart pump can be fully and comfortably implanted. However, in addition to this the inner radius of the drive is increased compared to traditional versions in order to allow for a large flow path cross-sectional area in the left pump inlet, which in turn helps flow characteristics within the pump.

The drive is configured to maximize efficiency and hence reduce energy usage, whilst maintaining an axial force (formed from the combination of the passive axial force between the impeller and the drive and the additional active axial force when the impeller is being rotated at a typical speed) to match the passive axial force generated by the magnetic bearing, to thereby help reduce energy usage by the magnetic bearing.

A further goal of the drive design is to allow the drive to function efficiently with a large air gap between the drive stator 132 and drive coils 131, and the permanent drive magnets 134 embedded within the rotor 121. In particular, this allows the impeller 120 to be implemented without requiring a shroud mounted on the impeller vanes, which can in turn induce high shear stresses and reduce the effectiveness of axial movement in controlling flow. In this regard, the resulting ratio of magnetic gap length to a total axial drive height between a stator and rotor yoke, as described in more detail below with respect to FIG. 4B, is large $$\left(\frac{l_{gap}}{h_{ax}} > 0.2\right).$$

In order to achieve this, various parameters of the drive, including the configuration of the drive stator core 132 and rotor 121 are selected in order to find an improved balance between the axial force and efficiency of the drive. As a result, the drive exhibits similar performance characteristics as prior versions, while size, weight and rotor inertia were reduced.

In considering the drive parameters, it is necessary to take into account the electromagnetic torque ($T_{el}$) generated by a permanent magnet drive, which can be formulated as the product of quadrature current ($i_q$) and field flux linkage ($\psi_f$):

$$T_{el} = \psi_f \cdot i_q$$

The field flux linkage is the portion of the permanent magnet flux, which crosses the air gap and closes through stator poles 132.1 and yoke 132.2. The flux linkage is depending on the total flux $\phi_f$ penetrating the coils on this path, and the coil turn number N:

$$\psi_f = N \cdot \phi_f$$

Thus, the torque is dependent on the number of turns in the drive coils 131 and the total flux generated.

The efficiency ($\eta$) of the drive is the quotient of mechanical output power ($P_{mech}$) and electric input power ($P_{el}$). The main power losses ($P_{loss}$) are copper winding losses ($P_{cu}$) and stator core losses ($P_{core}$) due to eddy currents and hysteresis.

$$\eta = \frac{P_{mech}}{P_{el}} = \frac{P_{mech}}{P_{mech} + P_{loss}}$$

$$P_{loss} \approx P_{cu} + P_{core}$$

The main power loss in the drive is generated in the copper windings of the drive coil. This is due to the machine size and the large air gap, which reduces the field flux linkage due to fringing effects and therefore requires a higher current to generate torque. Copper losses are proportional to the stator phase resistance and the square of the current.

$$P_{cu} = 3/2 \cdot i_q^2 \cdot R_{Ph}$$

The copper losses are the main losses and are affected by changes in the geometry. As the load changes, the copper losses change with the operating point (speed/torque) of the drive.

The drive motor constant $K_{Motor}$ expresses the relationship of torque and copper losses in a way that eliminates the dependency on the drive current. It is therefore a measure for the drive motor constant independent of the operating point or chosen wire thickness for a constant copper cross-sectional area in the slots.

$$K_{Motor} = \frac{T_{el}}{\sqrt{P_{cu}}} = \frac{\psi_f \cdot i_q}{\sqrt{\frac{3}{2} \cdot i_q^2 \cdot R_{Ph}}}$$

$$\sim \frac{i_q}{\sqrt{i_q^2}} \sim \frac{i_q}{i_q} = const$$

Drive Geometric Constraints and Objectives

The requirement of the drive to be incorporated into the pump places a number of geometric constraints and objectives on the pump design.

For example, the outer radius of the stator core and coils is limited (max. ~55 mm) to limit the total outer diameter of the pump, whilst the inner radius of the drive needs to be a minimum of 10.5 mm to allow for sufficient space for the left pump inlet, and in particular to allow for a larger inlet diameter which can improve hydraulic efficiency and flow characteristics to provide greater outflow pressure sensitivity. The axial height of the stator should be minimized to decrease the overall pump length.

The total assembly weight is to be minimized and the weight of the rotor assembly is to be minimized to decrease rotor inertia and therefore improve dynamic pump behaviour and efficiency, particularly when operated with a pulsatile or modulated speed profile.

The axial magnetic gap between the rotor and drive stator is set to a relatively large value of 3 mm+− the axial movement range of the impeller. This allows for semi-open impeller vanes with an increased height to pass through the volume in the magnetic gap. This generally reduces resistance to flow by increasing the minimum flow path area (especially at the inlet eye of the vanes) which improves both hydraulic efficiency and outflow pressure sensitivity, and avoids the need for an impeller shroud (carrying the magnets) which can increase the danger of hemolysis and other associated blood compatibility issues.

Figure 4A:
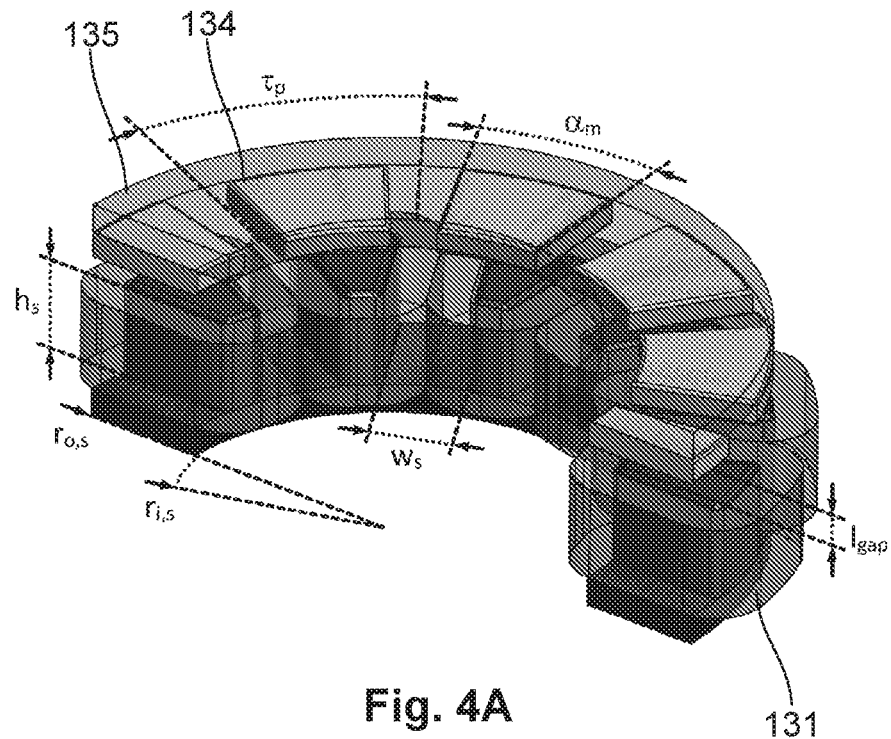
FIG. 4A is a schematic perspective view of an example of a drive illustrating different drive parameters.
Figure 4B:
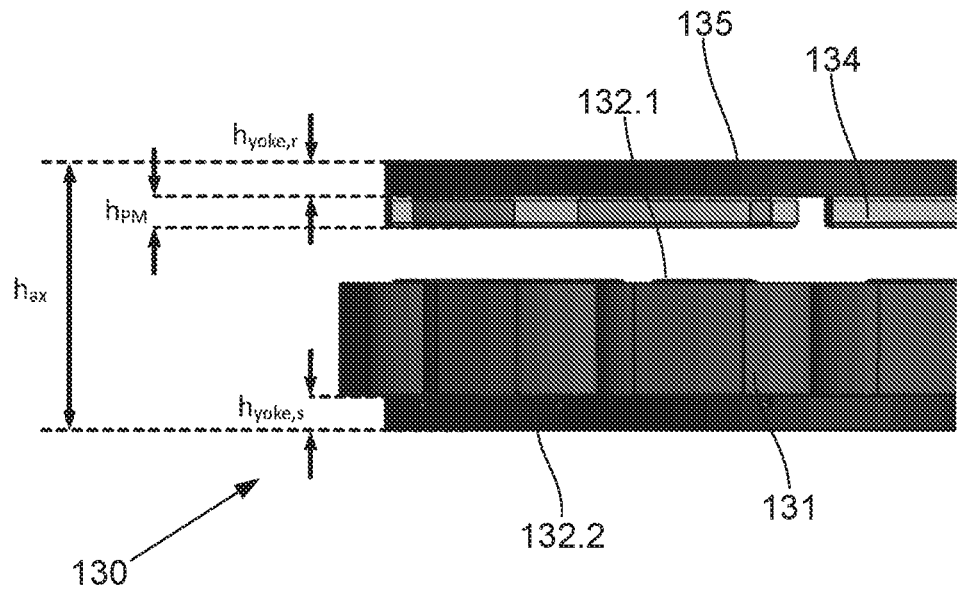
FIG. 4B is a schematic side view of the drive of FIG. 4A illustrating further drive parameters.

An example of the parameters that can be adjusted for the drive are shown in FIGS. 4A and 4B, and are summarised in Table 1 below.

TABLE 1

| Variable ID | Description |
| --- | --- |
| $w_s$ | Drive stator slot width |
| $r_o$ | Outer radius of drive stator core |
| $r_i$ | Inner radius of drive stator core |
| $h_s$ | Drive stator axial slot depth |
| $l_{gap}$ | Drive stator axial gap length |
| $h_{PM}$ | Drive magnet axial thickness |
| $h_{yoke, s}$ | Axial thickness of drive stator yoke |

TABLE 1-continued

| Variable ID | Description |
| --- | --- |
| $h_{yoke, r}$ | Axial thickness of drive rotor yoke |
| $a_m$ | Drive magnet pitch |
| $N_S$ | Number of drive stator poles |
| p | Number of drive magnets |

Drive Stator Slot Width

An example of the effect of a change in drive stator slot width will now be described with reference to FIGS. 5A to 5C.

In this regard the drive stator slot width corresponds to the space between adjacent drive stator poles 132.1 and affects the drive in a number of conflicting ways.

For example, increasing the drive stator slot width reduces the pole face area, resulting in the axial force $F_z$ also decreasing. As the air gap is large, the perceptual portion of stray flux increases and less of the permanent magnet flux crosses the axial gap and closes through the stator, meaning $\psi_f$ decreases and hence the motor constant $K_{Motor}$ and thus the drive motor constant decreases.

However, as the drive stator slot cross-sectional area increases, as shown in FIG. 5B, the number of windings in the drive coils 131 increases. Consequently, more flux $\phi_f$ passes through the more winding turns so $\psi_f$ increases and the motor constant $K_{Motor}$ increases.

However, additional turns mean the drive coil resistance increases, as the additional turns add to the total wire length, which in turn increases copper losses and hence partially counteract the increase of the motor constant $K_{Motor}$.

Alternatively, a larger diameter wire can be used in the larger slot to maintain the number of coils that were present in the original slot, however the larger diameter wire will have a smaller resistance therefore increase the efficiency of the larger slot drive.

A further impact arises due to the fact that the inner radius of the drive decreases due to the bigger end winding turns, resulting in a smaller space for the inlet area and increases in volume and weight. Additionally, the permanent magnet axial attractive force decreases steadily with increasing drive stator slot width, due to the reduced stator core volume, and hence the pole face surface area of stator magnetic material.

As a result, as shown in FIG. 5C, starting at a minimal drive stator slot width the drive motor constant, representing the drive motor constant, initially increases due to the increase in winding turns. At higher slot width this effect is reversed by decreasing efficiency due to increasing stator resistance and reduction of flux linkage penetrating the stator windings. Therefore, a maximum drive motor constant can be found for a specific drive stator slot width.

As a result of these considerations, adjacent drive stator poles are separated by a drive stator slot having a width of at least one of between 4 mm and 7.4 mm and more typically about 6 mm.

Drive Stator Core Size

The impact of drive stator core size is closely related to the drive stator slot width and has similar considerations, as will now be described with reference to FIGS. 6A to 6C.

In particular, increasing the inner core radii of the drive stator core reduces the pole face area and the active slot length ($r_o$-$r_i$). Consequently, the axial force $F_z$ that can be generated decreases, as does the resulting torque $T_{el}$.

Figures 6A, 6B:
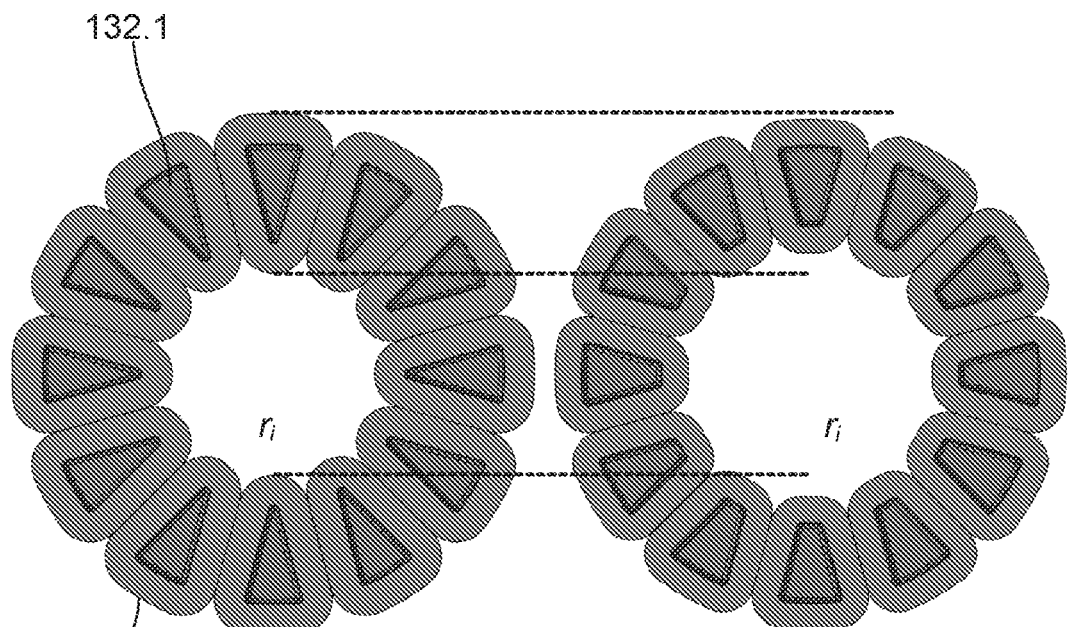
FIG. 6A is a schematic plan view of an example of a drive illustrating a first stator inner radius and first slot width.
FIG. 6B is a schematic plan view of an example of a drive illustrating a second stator inner radius and second slot width.
Figure 6C:
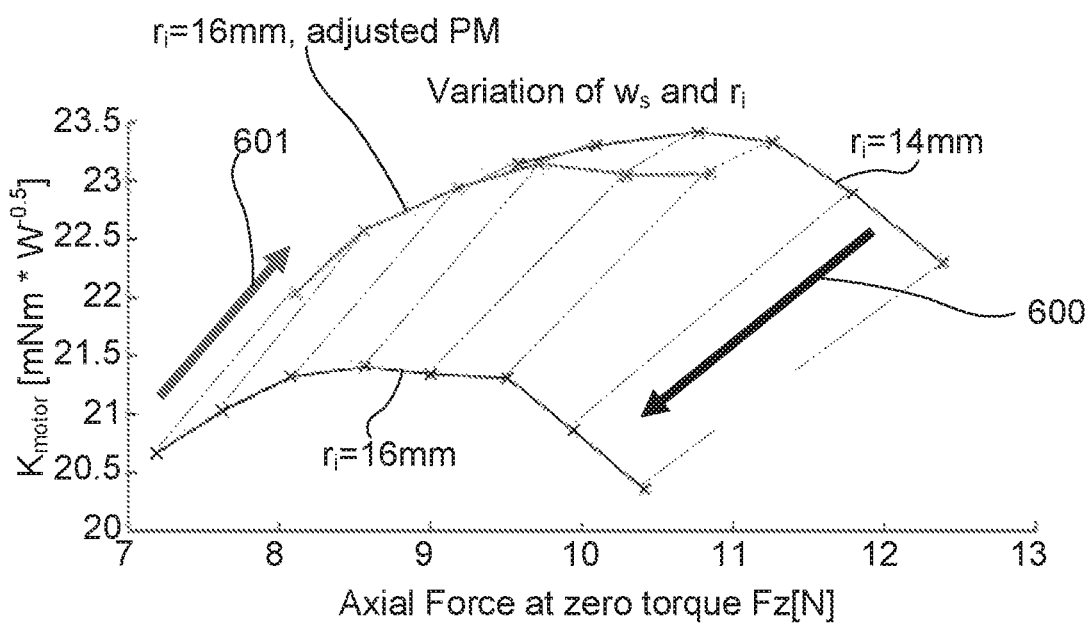
FIG. 6C is a graph illustrating an example of drive motor constant and axial force with changing stator inner radius.

In the example of FIGS. 6A and 6B, the inner radius $r_i$ is increased from 14 mm to 16 mm, resulting in a decrease in force $F_z$ and drive motor constant $K_{motor}$, as shown by the arrow 600 in FIG. 6C.

Decreasing the drive stator slot width from 4 mm to 7 mm is shown along the lower curve, whilst arrow 601 shows the impact of increases in permanent magnet thickness.

As a result of these considerations, the drive stator typically has an inner radius of between 12 mm and 20 mm, between 14 mm and 18 mm and more typically about 16 mm.

In contrast the outer radius of the drive stator is largely governed by geometric considerations, and aims to have as large a diameter as physically possible, sufficient to fit within the housing and able to accommodate the coil thickness between the outer edge of the drive stator core and the housing. Consequently, the drive stator core has an outer radius of between 22 mm and 25 mm and more typically about 24.5 mm.

Drive Winding Configuration

The preferred winding configuration is a concentrated double-layer winding. This allows the reduction of the size of the end-windings to allow for a large inner diameter of the motor. The drive pole configuration, and in particular the combination of number of stator slots and magnets in the rotor is governed by general principles of permanent magnet drives. Some of the feasible combinations can result in a higher winding factor and thus in a reduction of joule losses, which may be accompanied by a higher harmonic content of the magneto motive force causing increased rotor losses. However, a relatively large air gap has a low-pass filtering effect on the field harmonics, thus a reduction of the joule losses is preferred. Consequently, the number of drive magnets is typically one of 8, 10, 14 and 16, whilst the number of stator slots is one of 12, 15 and 18, with 10 drive magnets and 12 stator slots being the preferred configuration.

Although the drive motor constant $K_{Motor}$ is independent of wire size, the wire size and number of turns is affected by power supply limitations. The maximum operational speed of the motor is dictated by the ability of the supply voltage to overcome the back EMF induced in the motor coils by the permanent drive magnets and resistive losses in the system. The maximum torque that can be produced by the motor is proportional to the motor current and the motor torque constant and is limited by the amount of current that can be supplied without exceeding the thermal threshold of the driveline and motor.

For a fixed slot size and coil copper area, increasing the coil turn number increases the induced back EMF for a given rotor speed, thereby reducing the maximum speed achievable for a given supply voltage. However this will reduce the torque constant allowing higher torque to be produced for the maximum supply current. Conversely, with a lower turn number the maximum speed is increased, while the maximum torque is decreased. Winding the motor in wye or delta configurations can also be used to manipulate the trade-off of maximum speed and maximum torque as known in the art.

In battery operated applications, the battery voltage can limit the supply voltage. For an implantable device with a percutaneous driveline, the maximum thickness of the motor conductors, and therefore maximum current capacity, is limited by the diameter of the percutaneous driveline. As such for an implantable blood pump with a portable controller the maximum supply voltage is typically between 12V and 30V, and more typically approximately 24V, with the maximum supply current being between 3 A and 8 A, and more typically approximately 5 A.

Three such configuration of motor coil turn numbers were evaluated, as shown in Table 2. The motors were tested to determine their performance envelope as defined by their maximum speed and maximum torque for the same maximum supply voltage and maximum supply current, and results are shown in FIG. 6D.

TABLE 2

| Configuration | A | B | C |
|---|---|---|---|
| Coil design | 96 Turns (delta wound) | 96 Turns (wye wound) | 165 Turns (delta wound) |

Configuration A provides the lowest maximum torque, but the highest maximum speeds. Configuration B provides the highest maximum torque and the lowest maximum speed. Configuration C provides a combination of high torque and speed providing a compromise between the other two designs. For an application of a rotary blood pump with an expected speed operating range of 1500-2500 RPM the use of configuration B or C could provide additional maximum torque over the expected operating range compared to configuration A.

Drive Magnet Shape

Figure 7A:
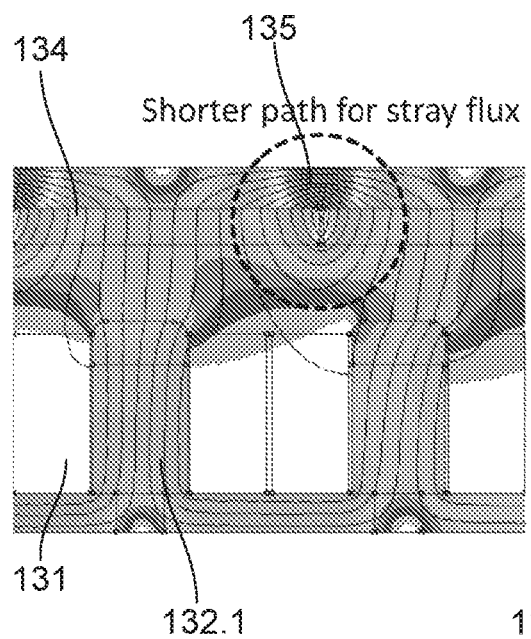
FIG. 7A is a schematic side view illustrating an example of the magnetic drive flux for a first drive magnet angle.
Figure 7B:
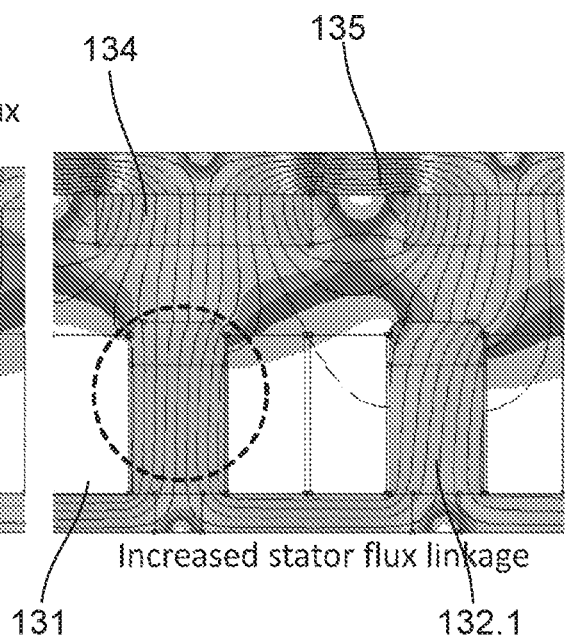
FIG. 7B is a schematic plan view illustrating an example of the magnetic drive flux for a second drive magnet angle.

Examples of the impact of drive magnet shape will now be described with reference to FIGS. 7A to 7C respectively.

For the purpose of this example, it is assumed that the drive magnets extend along an arc segment. The first consideration is that of magnet pitch am (or arc length), which affects the stray flux between adjacent drive magnets. In this regard, FIGS. 7A and 7B, show graphical representations of the flux through the drive stator poles and drive magnets for different drive magnet pitches (arc angles). This highlights that for the larger pitch angle, corresponding to a reduced separation between adjacent drive magnets, this results in a shorter path for stray flux, and hence reduced flux linkage between the drive stator and drive magnets when compared to smaller pitch angles, resulting in reduced axial force $F_z$. However, conversely, if the pitch angle is too small, this reduces the overall drive magnet strength and hence again reduces the axial force $F_z$. An example of this variation is shown in FIG. 7C, highlighting an optimum pitch angle.

Figure 7C:
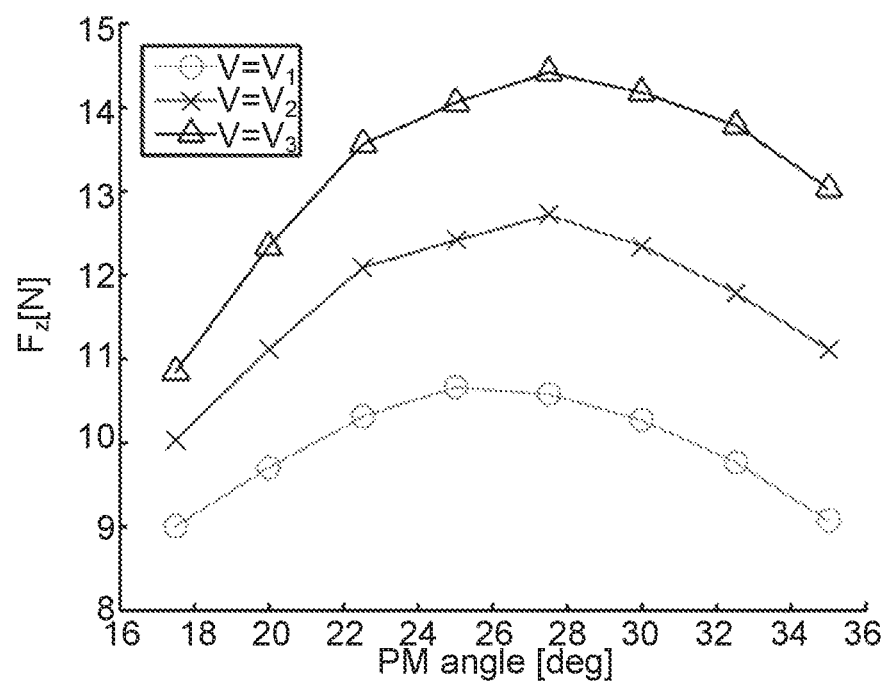
FIG. 7C is a graph illustrating an example of drive axial force with changing drive magnet angle.

Additionally, it will be appreciated that increasing the drive magnet thickness increases the magnet strength and hence the axial force, as shown by the successive lines on the graph of FIG. 7C. This also leads to an increase in efficiency as shown in FIG. 7C. However, this also increases the rotor weight and hence the rotor inertia, as well as being limited by the physical dimensions of the rotor.

Figure 7D:
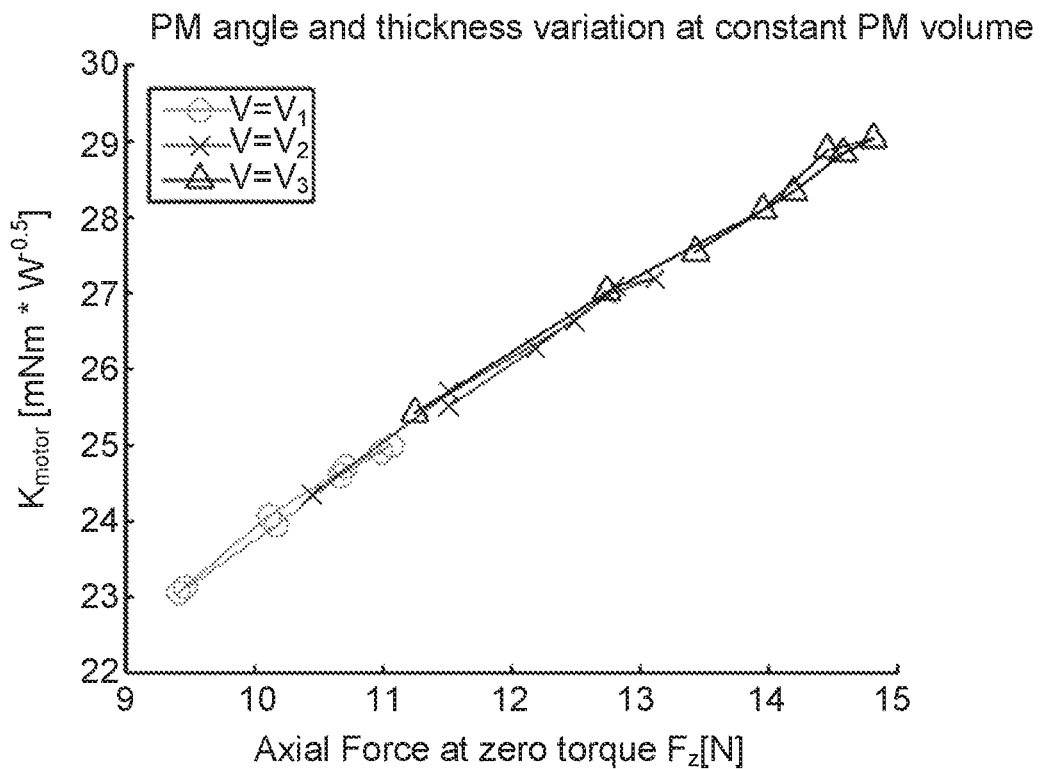
FIG. 7D is a graph illustrating an example of drive motor constant and axial force with changing drive magnet angle and thickness.

The variation of the drive magnet axial thickness $h_{PM}$ and the drive magnet pitch or arc length $a_m$ also effects the motor constant as demonstrated in FIG. 7D. Although variation of the permanent magnet (PM) angle and thickness can return a range of attractive forces, there is a strong correlation between the resulting attractive force and the motor constant. As such it is possible to select multiple PM geometries that satisfy a given axial force motor constant requirement. Therefore, consideration should be made to the physical effects these different PM geometries have on the rotor and pump design.

Consequently, it will be appreciated that the drive magnet pitch angle can be selected so as to maximise the material utilization (efficiency) of the permanent magnets. Consequently, each drive magnet extends along an arc segment transecting an angle at least one of between 15° and 36° and preferable about 25°.

Once the drive magnet pitch angle has been determined, the magnet height is selected to adjust performance of the drive torque $K_{motor}$ and axial force $F_z$. In this regard, each drive magnet typically has a thickness of between 0.8 mm and 3 mm and more typically about 2.6 mm. In one example the drive magnets have a grade of $BH_{max}=48$.

Drive Yoke Shape

The drive stator yoke and rotor drive yoke are provided to ensure flux linkage between adjacent drive magnets and drive stator poles. Accordingly, the rotor drive yoke, typically made of soft iron, and drive stator yoke, typically made from a soft magnetic composite (SMC), such as Somaloy are selected to have sufficient cross-sectional area to provide sufficient flux linkage, whilst minimising the respective weights. The use of a composite yoke can be beneficial as the sintered characteristics remove the need to create a laminated core, which is traditionally required to reduce eddy current losses and improve efficiency. However laminating the core of an axial flux motor requires the creation of concentric 'tree' rings, which are very difficult to manufacture. Where appropriate the rotor yoke elements of the bearing and motor can be combined as long as the combined thickness is chosen with consideration to the combined saturation characteristics of both the motor and bearing.

In one example, the drive stator and rotor drive yokes 132.2, 135 have a thickness of between 1 mm and 5 mm, between 1.5 mm and 2.5 mm and more typically of between about 1.75 and 1.9 mm respectively. The rotor drive yoke can be a separate element or combined with the rotor bearing yoke.

Drive Stator Slot Depth

Figure 8F:
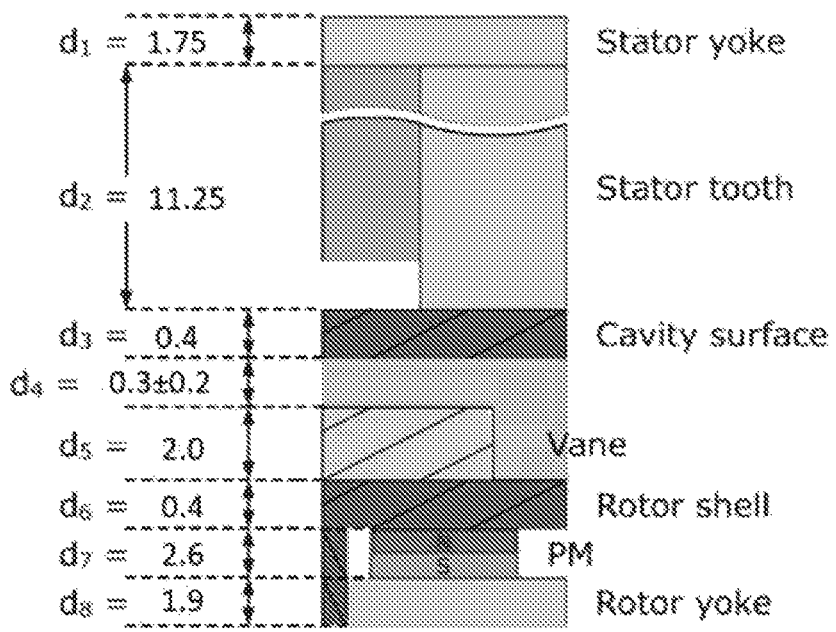
FIG. 8F is a schematic diagram of specific preferred drive parameters.
Figures 8A, 8B:
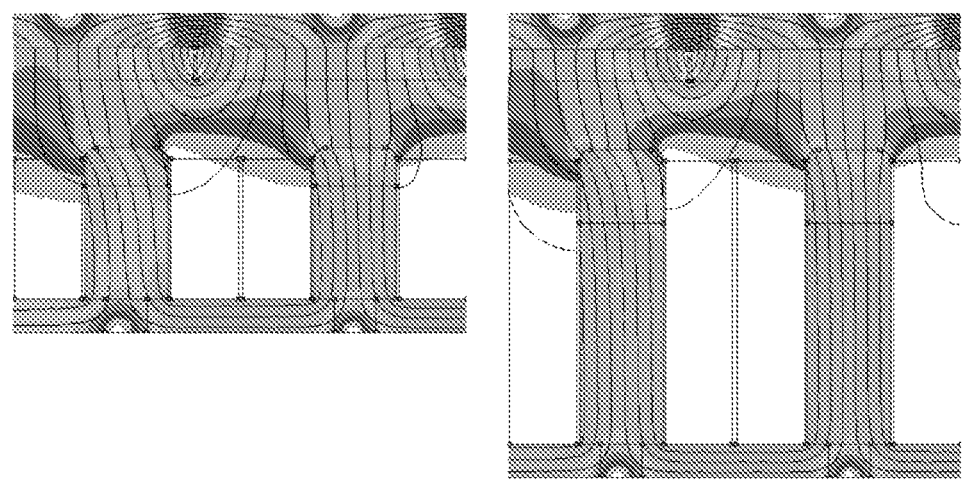
FIG. 8A is a schematic side view illustrating an example of the magnetic drive flux for a first drive stator slot depth.
FIG. 8B is a schematic plan view illustrating an example of the magnetic drive flux for a second drive stator slot depth.
Figure 8C:
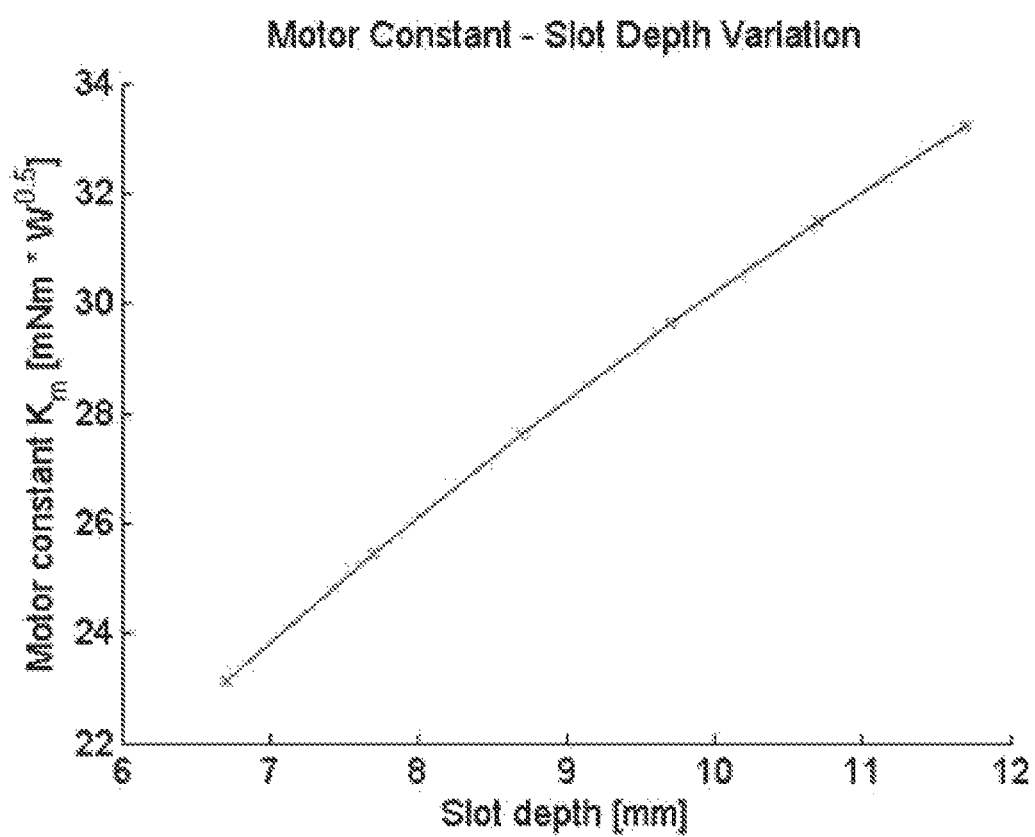
FIG. 8C is a graph illustrating an example of drive axial force with changing drive stator slot depth.

An example of the impact of drive stator slot depth will now be described with reference to FIGS. 8A to 8C respectively.

In this regard, increasing the drive stator slot depth allows for an increase in the number of windings in the drive coils 131, without a corresponding reduction in pole face area as is the case with increasing the slot width. Accordingly, increasing the drive stator slot depth can increase the drive torque and efficiency, as shown in FIG. 8C, without a change in axial force $F_z$.

It should be noted that whilst reluctance (magnetic resistance) of the magnetic circuit increases due to the longer iron path through the stator, leading to a smaller field flux linkage, the effect of this is negligible as the reluctance of the increased iron length is in the range of a factor of 1000 smaller than the reluctance of the large air gap.

Doubling the drive stator slot depth also results in doubled coil resistance and doubled flux linkage, if the slot is effectively filled with coils of the same diameters as before Accordingly, it will be appreciated that increasing the drive stator slot depth generally increases the performance of the system. However, this needs to be balanced by geometrical constraints, and in particular the desire to minimise the length and weight of the drive stator and hence pump.

Accordingly, in one example, the other parameters outlined above are optimised, with the drive stator slot depth being selected so as to ensure a required drive torque and efficiency are obtained. In one example, the drive stator slot depth is selected to be between 4 mm and 14 mm and typically about 11.25 mm.

It will be appreciated from the above that combinations of geometry changes can be combined to achieve a compromise regarding the design objectives. In particular, changes in the permanent drive magnet geometry allow adjustment of the efficiency/force ratio $K_{motor}/F_z$, with the parameter changes being performed so as to decrease the volume/weight of both the drive stator and rotor components, whilst ensuring efficiency and force requirements are met.

A summary of the preferred and optional ranges of the different parameters is set out in Table 3 below, with specific values being further shown in FIG. 8F:

TABLE 3

| Variable ID | Description | Range | Optimum | Unit |
| --- | --- | --- | --- | --- |
| $w_s$ | Drive stator slot width | 4-7.4 | 6 | mm |
| $r_o$ | Outer radius of drive stator core | 22-25 | 24.5 | mm |
| $r_i$ | Inner radius of drive stator core | 14-18 | 16 | mm |
| $h_s$ | Drive stator axial slot depth | 6.7-13.2 | 11.25 | mm |
| $l_{gap}$ | Drive stator axial magnetic gap length | 2.5-4 | 3.2 +− movement | mm |
| $h_{PM}$ | Drive magnet axial thickness | 0.8-3 | 2.6 | mm |
| $h_{yoke, s}$, $h_{yoke, r}$ | Axial thickness of drive and rotor stator yoke | 1-5 | 1.75 | mm |
| $a_m$ | Drive magnet pitch | 15-36 | 25 | degree |
| $K_{PM}$ | Magnet strength | N28H-N48H | N48H | — |
| $N_S$ | Number of drive stator poles | 12, 15, 18 | 12 | — |
| p | Number of drive rotor poles | 8, 10, 14, 16 | 10 | — |

These parameter variations allow for the design of drive systems that stays within the geometrical constraints and can operate over a significant magnet airgap whilst still satisfying particular axial force requirement and maximising the efficiency.

In one example, this allows for a spacing between the first face of the rotor and the first end of the cavity that is at least one of between 2 mm and 5 mm in use, between 2.0 mm and 3 mm in use and approximately 2.3 mm (±axial movement of the impeller) in use. Similarly this can allow for a spacing between a stator pole face and drive magnet face is at least one of between 2.5 mm and 6 mm in use, between 2.5 mm and 4 mm in use and approximately 3.2 mm (±axial movement of the impeller) in use. Alternatively this can allow for a spacing between a stator yoke and drive magnet to be at least one of between 7 mm and 25 mm in use, between 8 mm and 20 mm in use and approximately 17. mm (±axial movement of the impeller) in use, or a spacing between a stator pole face and drive magnet yoke to be at least one of between 4 mm and 8 mm in use, between 4.5 mm and 7 mm in use and approximately 5.8 mm (±axial movement of the impeller) in use.

This is advantageous as it allows for a spacing between the first face of the rotor and the first end of the cavity to be at least 2.3 mm in use, which in turn allows the vanes to be mounted on the first face of the rotor between the first face of the rotor and the first end of the cavity, with the vanes having a height of between 1.5 mm and 5 mm, between 1.5 mm and 2.5 mm, between 1.8 mm and 2.2 mm and about 2 mm, whilst avoiding the need for a shroud mounted on the vanes, as previously discussed, and whilst allowing for up to ±0.3 mm of axial movement of the impeller in use.

Figure 8D:
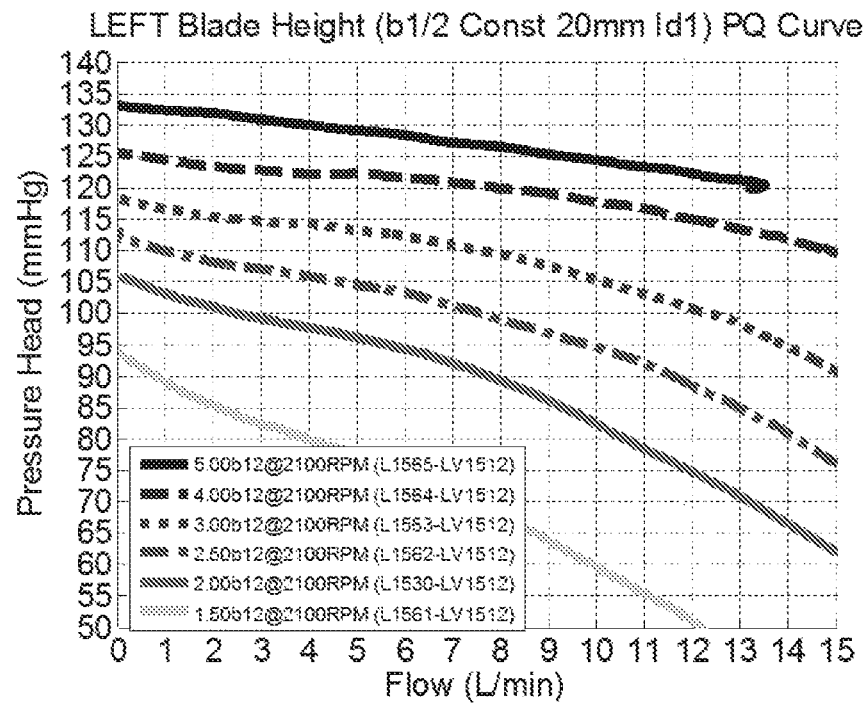
FIG. 8D is a graph illustrating an example of left pump curves for different impeller left vane heights.

While it is a traditional design philosophy to minimize the magnetic airgap of a drive system to improve efficiency, an increased magnetic airgap can be advantageous in the design of a blood pump due to the significantly higher vane height that is able to be accommodated. FIG. 8D shows that the higher impeller vanes can decrease the absolute value of the gradient of the pressure-flow pump curve. This decreased pump gradient can improve the physiological interaction of the device with the circulatory system. As such, design of motors with significantly large air-gaps can be advantageous to rotary blood pump designs.

Figure 8E:
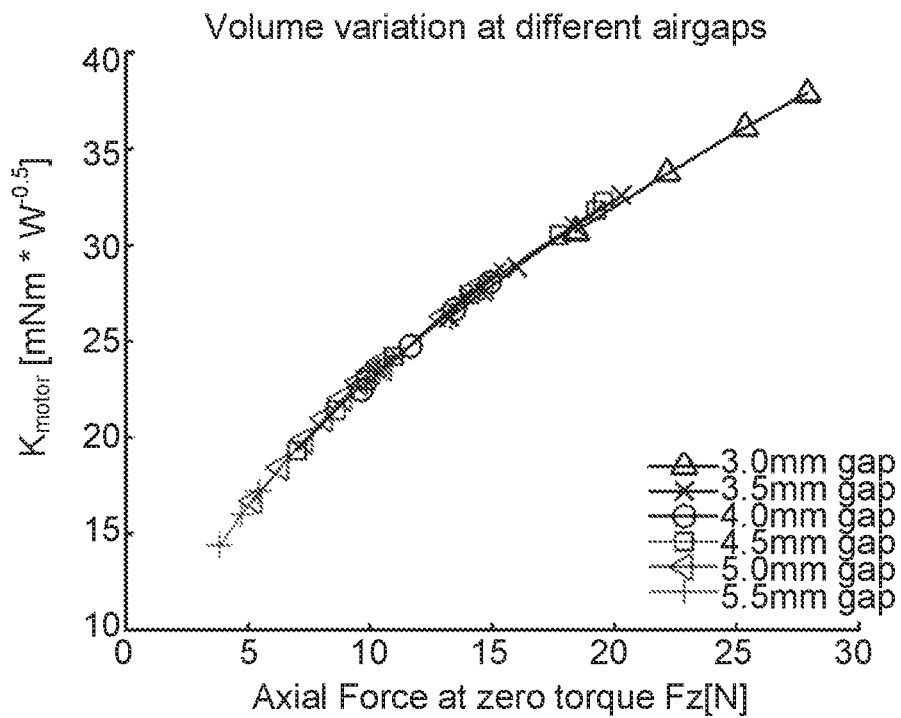
FIG. 8E is a graph illustrating an example of drive axial force and motor constant for different air gaps.

Although the increase of the motor magnetic airgap will inherently decrease the efficiency of the device, through the manipulation of the aforementioned parameters it is possible to create a motor which operates with a similar motor constant to a smaller airgap motor as shown in FIG. 8E. In particular this can be achieved by increasing the permanent magnet strength in terms of increasing the magnet volume and/or magnetization grade.

Bearing Design

As previously described, the rotor is balanced in an axial direction using magnetic forces from the drive and the magnetic bearing. To minimize energy usage, the magnetic bearing and drive are configured so that the axial forces caused by the drive and bearing, are substantially balanced when the rotor is provided at a balance point at a normal operating speed, which may for example by approximately at a center of the cavity under conditions of normal flow.

The rotor is then suspended actively in the axial direction using a closed loop feedback system, in which the sensor(s) 160 detect the rotor position and controller 150 determines the magnetic bearing current required to position the rotor at a desired setpoint. Thus the difference between the drive attractive force, magnetic bearing passive attractive force and any external axial forces is balanced by the magnetic bearing electromagnetic forces. The point at which the drive and passive magnetic bearing forces match is a balance point $b_z$ and is defined in terms of the position in the casing and the magnitude of the opposing forces $b_F$.

The desired setpoint is selected based on flow requirements for the pump. In this regard, controlling the physical separation between the vanes and the cavity wall adjusts the efficiency of the respective impeller and therefore can be used to control flow. As has been described elsewhere, in a total artificial heart (TAH), moving the impeller can therefore be used to allow for relative flow control between the left and right hand pumps.

In one example, the controller 150 can implement a virtual zero power controller, which seeks to move the rotor such that the average current used by the magnetic bearing is controlled to a given level (for example 0 A). In this case, the amount of movement of the rotor by the controller 150 for a given external force acting on the rotor is determined by the rotor axial passive force stiffness ($k_{Fz}$), which is given by:

$$k_{Fz} = -\frac{dF_z}{dz}$$

where: $F_z$ is the axial force

For the application of the total artificial heart, the VZP (Virtual Zero Power) movement resulting from hydraulic forces acting on the rotor should be chosen based on the expected hydraulic forces and the required movement to balance those forces and improve flow balancing. As such it is advantageous to design the system components such that the axial passive force stiffness is matched to the expected hydraulic forces.

Figure 9A:
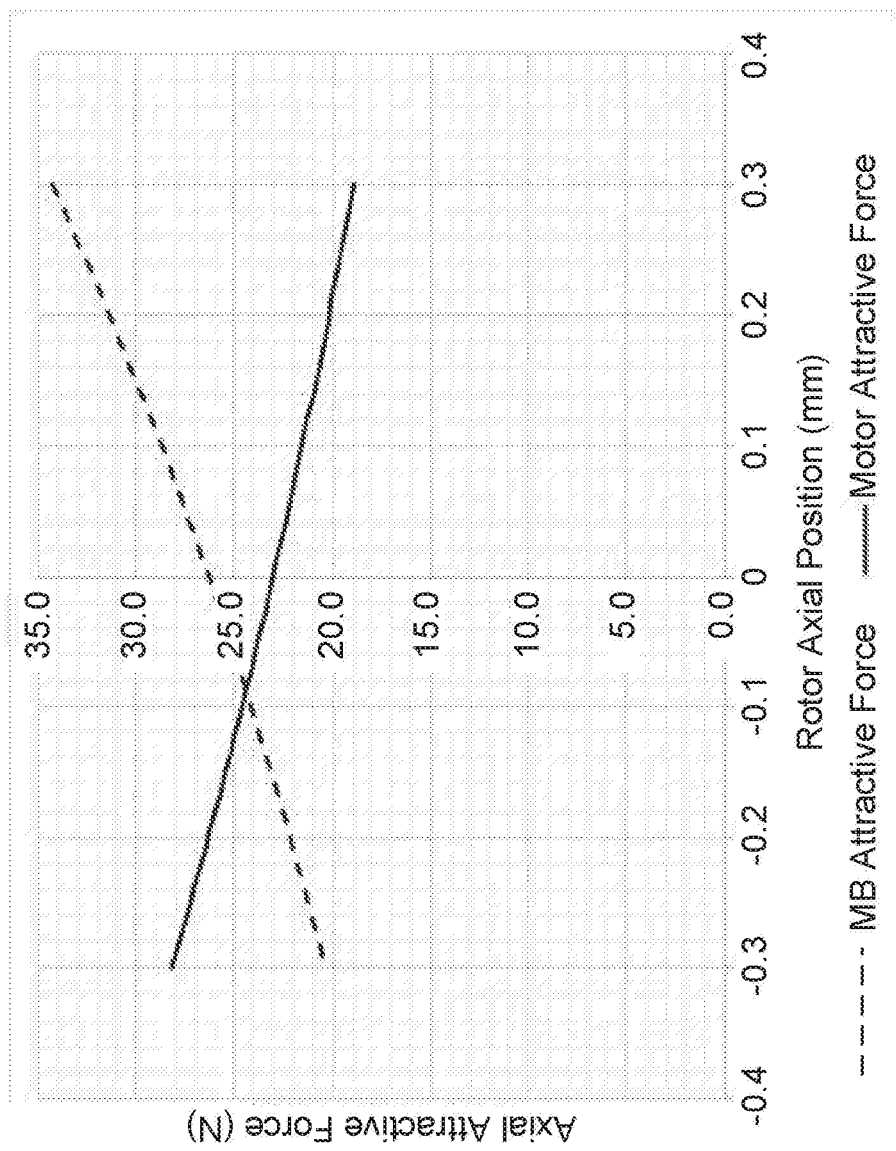
FIG. 9A is a graph illustrating the change axial drive and bearing forces for different impeller axial positions.

The axial position at which the two attractive forces are equal is the point at which the rotor will balance with zero steady state current and zero external forces. An example of this is shown in FIG. 9A.

In particular, in this example, when the rotor is centrally positioned (rotor position 0), the drive and bearing attractive forces are equal at 24.5N. If the rotor moves to the left, towards the drive, the drive attractive force increases, whilst the bearing attractive force decreases, leading to a net force towards the drive. The converse situation is true if the rotor moves to the right. It will be appreciated that this inherent instability is controlled through the use of the active magnetic bearing to counteract the difference in drive and bearing forces.

Figure 9B:
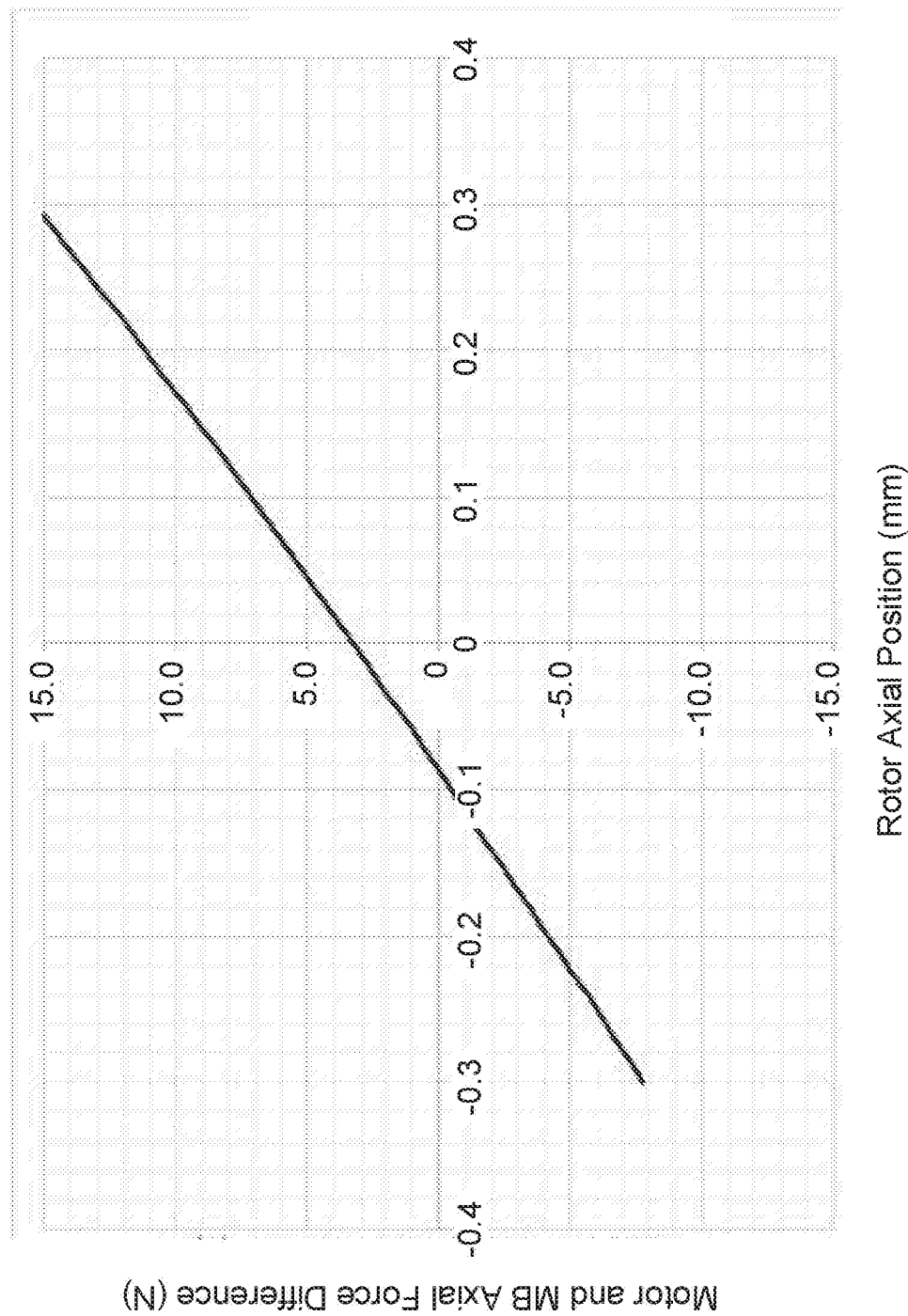
FIG. 9B is a graph illustrating the change in net axial force for different impeller axial positions.

The gradient of the force difference ($k_{Fz}$ [N/mm]) is made up of the combination of the drive axial force stiffness ($k_{F,MTR,z}$) and magnetic bearing axial force stiffness ($k_{FMB,z}$), as shown in FIG. 9B. Where the drive axial force is $F_{MTR,z}$ and the magnetic bearing axial force is $F_{MB,z}$.

$$k_{Fz} = -\frac{dF_z}{dz} = -\left(\frac{dF_{MB,z}}{dz} + \frac{dF_{MTR,z}}{dz}\right)$$

The magnitude of the overall force stiffness $k_{Fz}$ dictates the axial movement (dz) of the rotor for a given change in external axial force (N).

$$dz = -\frac{dF_z}{k_{Fz}}$$

The value of $k_{Fz}$ should be designed such that the required axial movement is achieved for the change of external forces caused by alterations in pressure acting on the rotor.

In addition to considering the axial stiffness, it is also necessary to consider the radial stiffness of the bearing. In this regard, in prior art arrangements, the rotor is typically suspended in a radial direction through the use of a radial bearing, such as a hydrodynamic journal bearing. However, this arrangement relies on maintaining a minimum separation between the rotor and the cavity side wall, which in turn leads to regions of high shear stress, which can in turn lead to hemolysis and destruction of other formed elements in the blood. Accordingly, it is desirable to provide alternative radial suspension mechanisms.

Figure 9C:
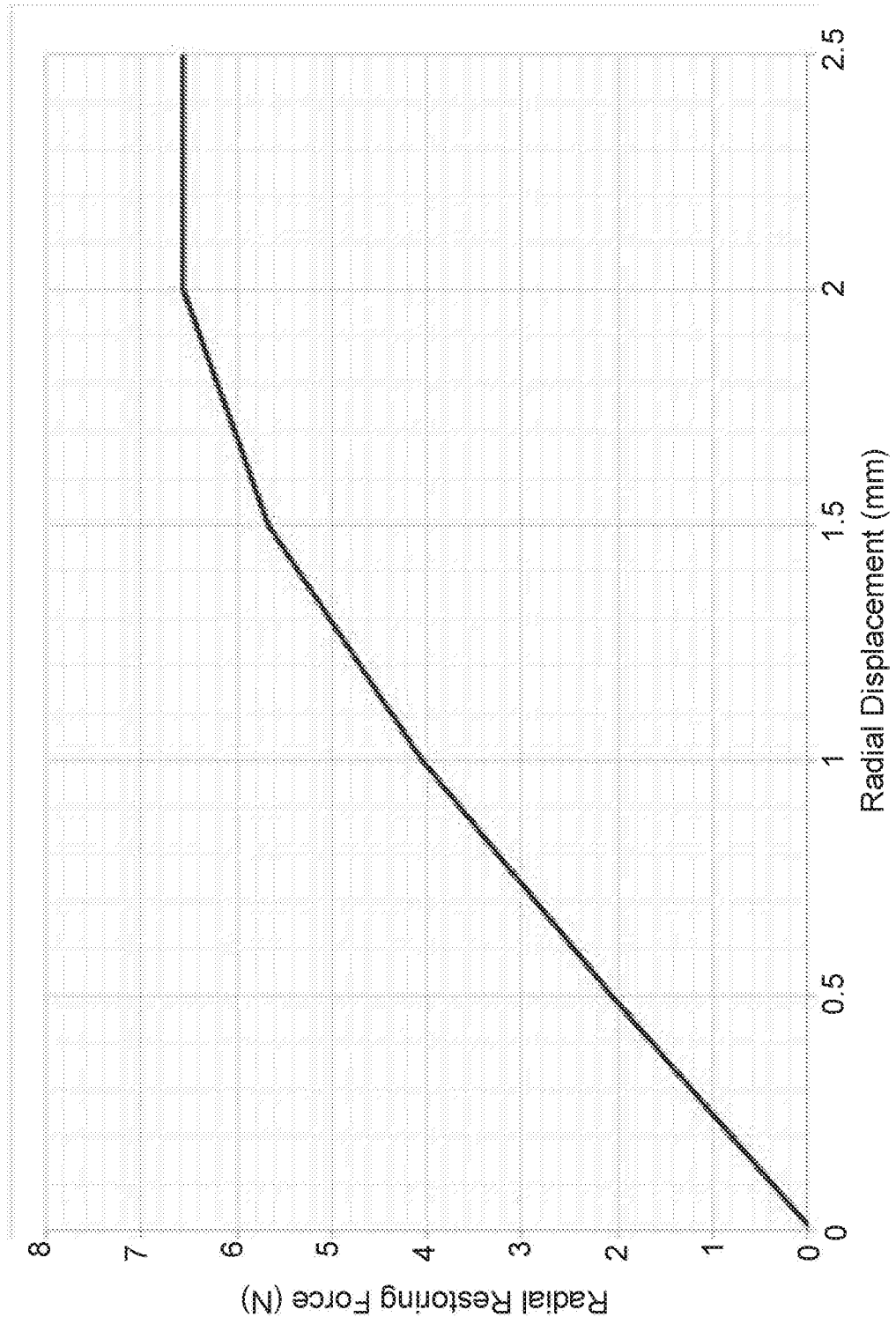
FIG. 9C is a graph illustrating the change in net radial force for different impeller radial positions.

Inherently, the passive magnetic forces of the drive and magnetic bearing create a degree of restriction to movement in the radial direction, so that the rotor is at least partially suspended in the radial direction. The radial restoring forces are typically measured in radial force stiffness, and an example of the profile of the radial restoring force is shown in FIG. 9C.

The maximum static external radial force that the pump can withstand before touching down radially is the maximum radial force at the maximum radial movement. As such it is advantageous to increase the passive radial restoring forces between the magnetic bearing and the rotor, so that the bearing and drive can provide the required degree of radial suspension.

Additionally the radial stiffness of the system, along with the damping and rotor mass, influence the vibrational response of the rotor, particularly close to the resonant frequency. Because the radial movement of the rotor is controlled passively, selection of the radial stiffness should take into consideration the relationship between the radial resonant frequency and the speed range at which the device is expected to operate. Due to an imbalance added to the rotor by the ingestion of foreign tissue, the rotor may be imparted with a forced excitation in the axial and/or radial direction at the rotational frequency. Operation of the device speed close to the radial resonance can induce a vibration in the rotor radial position that, without sufficient damping, can cause the rotor to whirl and influence the performance of the axial magnetic bearing system. Operation of the rotor below this resonant frequency is referred to at subcritical, whilst operating at speeds above this is referred to as supercritical.

In situations where the operational speed range captures the speed that coincides with the radial resonant frequency, the radial stiffness could be increased or the rotor mass could be decreased to subsequently increase the radial resonant frequency higher than the operating speed range. Conversely the radial stiffness could be decreased or the mass increased to reduce the radial resonant frequency below the speed operating range, however the latter approach will typically result in a reduction of the radial force capacity and additional mass for the axial magnetic bearing system. As such in applications such as this it is advantageous to increase the radial stiffness until the radial resonant frequency is above the operating speed range.

Accordingly, it will be appreciated that the above lead to particular requirements for the magnetic bearing and drive.

In particular, for a given hydraulic system and pump configuration it may be required to have a given axial stiffness $k_{Fz}$ and a balance position $b_z$ for balance forces $b_F$. The total stiffness value is the sum of the magnetic bearing stiffness and drive stiffness, and both the magnetic bearing and drive must produce the same force at the balance point $b_z$.

In addition to satisfying the requirements above, it is advantageous to maximize the bearing axial efficiency (N/W$^{0.5}$) and the drive motor constant (Nm/W$^{0.5}$)

It will also be appreciated that in order to maximize the degree of axial movement for a given magnitude of axial force, it is desirable to have a magnetic bearing that has a low axial stiffness. However, in order to provide high passive radial suspension force capacity and ensure the radial resonant frequency is sufficiently high, it is desirable to have a high radial stiffness.

Whilst balancing requirements can be met simply through adjustment (eg increase) of the relative separation of the bearing and rotor, this would reduce the efficiency and also the radial stiffness.

Taking the above into account, it will be appreciated that it is desirable to configure the drive so that it has the required stiffness and force balance point while maximizing the efficiency, as previously described. The magnetic bearing must then be designed to provide the required stiffness and force balance point while maximizing the efficiency and radial stiffness. This process will now be described in further detail.

Force Stiffness

Axial stiffness is the change of force for a change of axial separation between the stator and target. It is measured in N/mm. It can be expressed mathematically as $$k_{Fz} = -\frac{dF_z}{dz}.$$

Radial stiffness is the change of force between a stator and target for a change of radial alignment (while axial separation is kept constant). It can be expressed mathematically as $$k_{Fr} = -\frac{dF_r}{dr}.$$

The source of the magnetic flux and therefore the magnetic force can be either or both a permanent magnet or an electromagnetic coil.

Reluctance/Reluctance Stiffness

Reluctance is a magnetic analog of electrical resistance. The path for the magnetic flux to flow and the permeability of the materials in that path define the reluctance of a circuit. The SI unit of Reluctance is inverse henry, H$^{-1}$. It traditionally has the symbol of script R $\mathfrak{R}$.

Materials such as iron have a high permeability which easily allows flux to flow through them and as such when they are used in the flux path (for example in the stator). Air gaps in the flux circuit tend to increase the reluctance due to their low permeability. For example, when the airgap increases between the stator and target (perhaps when the target is moved) the reluctance of the circuit increases.

A higher reluctance of a magnetic circuit implies that less magnetic flux will flow for the same magnetic-motive force (MMF is an analog of voltage in an electrical system).

The change of reluctance for a change of relative position between the stator and target can be defined in terms of a stiffness. The stiffness can be written as $$k_{Rx} = \frac{d\mathfrak{R}}{dx} \text{ or } k_{Rz} = \frac{d\mathfrak{R}}{dz}$$

depending on the axis of movement i.e. the change of reluctance for the change of position along the x axis Force/Reluctance The change of force for a change of position (force stiffness) is dependent on the change of flux in the circuit for the change of position. Since the reluctance stiffness is a measure of how easy it is for the flux to flow, these quantities are intrinsically related.

Therefore the force stiffness is a function of the reluctance stiffness.

$$\frac{dF}{dx} = f\left(\frac{d\mathfrak{R}}{dx}\right)$$

To maximize the force stiffness implies that the reluctance stiffness is also maximized and vice versa.

In one embodiment the heart pump is configured to have an axial system stiffness of at least one of: at least 10 N/mm; at least 20 N/mm; at least 30 N/mm; less than 60 N/mm; less than 50 N/mm; about 10-60 N/mm; about 25-50 N/mm; about 30-40 N/mm; and, about 35-40 N/mm.

Stiffness Ratio

The stiffness ratio can be defined as the ratio between the stiffness in one axis with the stiffness of another axis, for example in the radial versus axial directions.

$$SR = k_{Fr}/k_{Fz} = -\frac{dF_r}{dr} / -\frac{dF_z}{dz}$$

The overall forces can be increased or decreased by changing the bearing permanent magnet strength. However the relative changes in the forces will follow the stiffness ratio. Therefore if a new design has a higher stiffness ratio, it can match the radial stiffness value of a previous system, but with a lower axial stiffness.

Increasing the stiffness ratio can be accomplished by increasing the amount of reluctance change for a given radial movement. This is primarily achieved by designing the highly permeable materials (iron) such that they change the flux path as the two objects are moved in relation to one another.

An example of this will now be described with reference to FIGS. 10A to 10D.

Figure 10A:
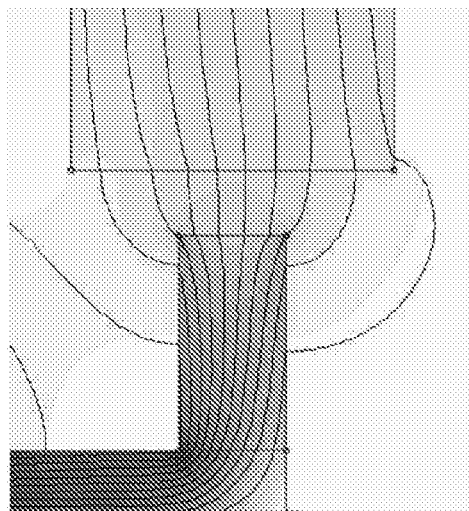
FIGS. 10A and 10B are schematic side views illustrating magnetic bearing flux for different radial positions of non-tapered magnetic elements.
Figure 10B:
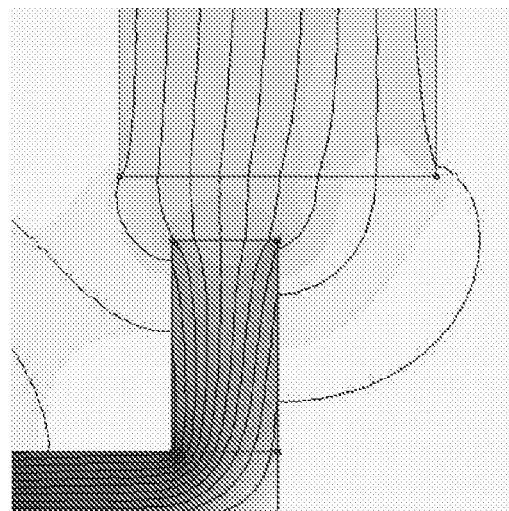

In the example of FIGS. 10A and 10B, two magnetic components, such as a bearing stator leg 142.1 and bearing magnet 144 having flat wide profiles are moved laterally, corresponding to radial movement of the rotor. In this example, radial movement does not change the flux path significantly due to overlap of the magnetic components, so even after the radial movement is performed there is a similar path for the flux to take, so the reluctance stays the same.

Figure 10C:
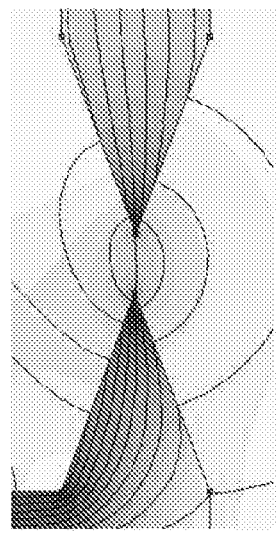
FIGS. 10C and 10D are schematic side views illustrating magnetic bearing flux for different radial positions of tapered magnetic elements.
Figure 10D:
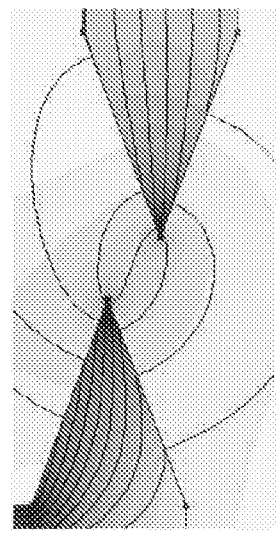

In contrast, in the configuration of FIGS. 10C and 10D, the magnetic components terminate in tips. In this example, radial movement does change the flux path significantly due to the increase in the air-gap. Consequently, when the parts move laterally relative to one another, corresponding to radial displacement of the impeller, the reluctance increases, therefore provides a restoring force.

An alternative analogy to consider is an electrostatic analogy in which there are constant "magnetic charges" on the surfaces of the magnets, which generate magnetic fields and when the pole tips are exposed to those fields, there are magnetic charges induced on those tips having the polarities opposite to those of the charges on the corresponding surfaces of the magnets. Importantly, the charges on the surfaces of the magnets are not changing, whereas the induced charges on the pole tips are fluent and can move around the pole surfaces to minimize the overall energy of the magnetic field.

By limiting radial width of a pole, the freedom of those induced charges to move around the pole surface is limited, meaning they can move only with the pole and, therefore, force the entire pole to move to a position with lower overall magnetic energy. In other words, a force exerted on the induced charges does actually get transmitted to the pole rather than simply causing charge redistribution within the pole. In addition, using the tapered pole results in higher densities of the magnetic charges in the pole areas where they contribute to generation of the radial forces.

Accordingly, it will be appreciated that a narrower tip leads to an increase in radial stiffness.

Bearing Configuration

Accordingly, it will be appreciated that in the heart pump described above, the magnetic bearing 140 is configured to provide active control in the axial direction and passive stability in the radial direction.

The axial force stiffness between the magnetic bearing and rotor influences the relative movement of the rotor due to external hydraulic forces acting on the rotor. Lowering the axial force stiffness typically improves the operation of the zero power controller by allowing the rotor to move further for a given change in hydraulic force brought about by alterations in circulatory resistance and thus pressure. However there could be a lower limit to the axial stiffness dictated by the force requirements of a backup hydrodynamic bearing system or by the requirement of the zero power controller to limit the rotor movement for an expected external axial force.

The radial force stiffness between the magnetic bearing and the rotor is used to stabilize the rotor in the radial direction when the rotor is acted upon by external forces, such as hydraulic forces due to unbalanced pressure recovery within the volute collector around the circumference of the impeller, synchronous forces generated by the rotation of the rotor with mass imbalance, or shock forces due to patient everyday movement. Since the radial stability of the rotor is dependent on the radial stiffness of the magnetic bearing system, increasing the radial stiffness improves the stability of the device and improves the maximum static and/or shock force that can be accommodated prior to radial touchdown. A higher radial stiffness can also ensure that the radial resonance is sufficiently high such that the rotor runs subcritical over its entire speed range.

To improve the system performance the magnetic bearing should maximize the radial stiffness while simultaneously minimizing the axial stiffness. Accordingly, the magnetic bearing is designed to maximize the radial to axial stiffness ratio.

In one example, this can be achieved ensuring that all or part of the bearing stator legs 142.1, 142.2 are narrower than the magnetic bearing members 144, 145 in a radial direction relative to the rotor. This can be achieved by narrowing the entire stator leg or by introducing tapering adjacent the air gap into the magnetic circuit formed by the magnetic material 144, 145 in the rotor and the bearing stator legs 142.1, 142.2 of the bearing stator 142.

An example of this will now be described with reference to FIGS. 11A to 11D.

Figure 11A:
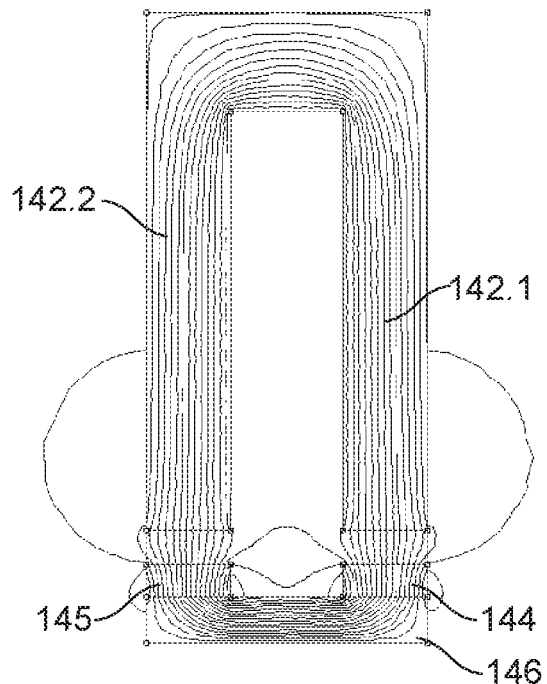
FIGS. 11A and 11B are schematic side views illustrating magnetic bearing flux for different radial positions of an example of a magnetic bearing including non-tapered magnetic bearing stator legs.
Figure 11B:
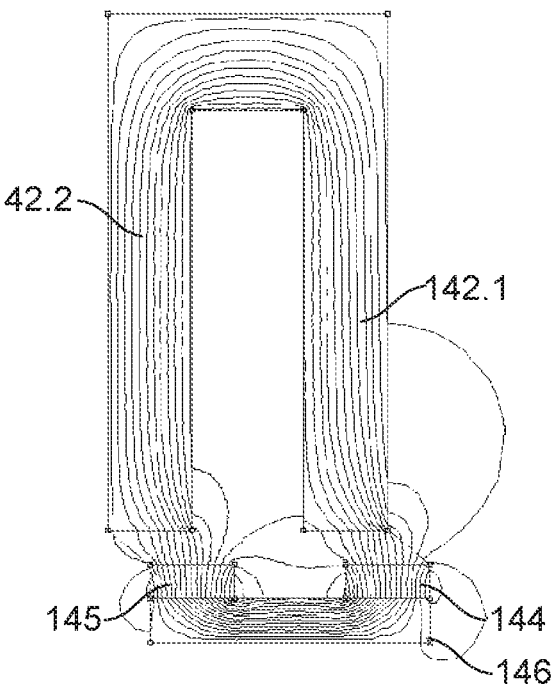

In the example of FIGS. 11A and 11B, the bearing stator legs 142.1, 142.2, and magnetic bearing members 144, 145, which in this case are permanent magnets, do not include tapering. Consequently as the rotor moves radially as shown in FIG. 11B, there is little if any reluctance change and hence minimal radial stiffness.

Figure 11C:
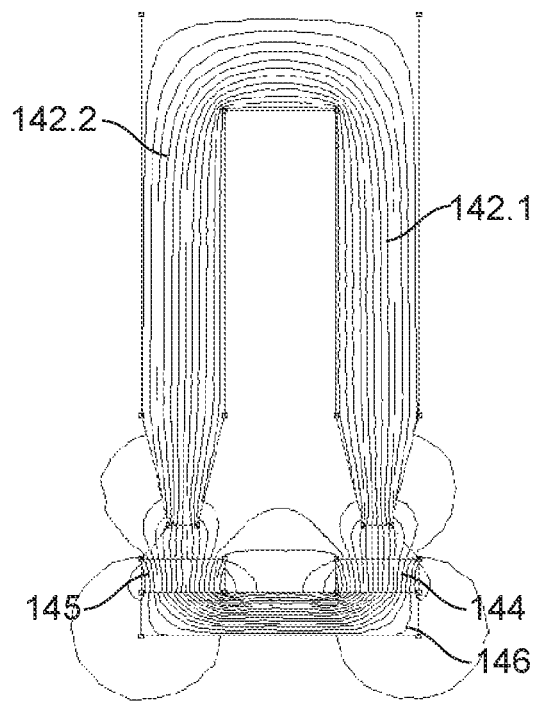
FIGS. 11C and 11D are schematic side views illustrating magnetic bearing flux for different radial positions of an example of a magnetic bearing including tapered magnetic bearing stator legs.
Figure 11D:
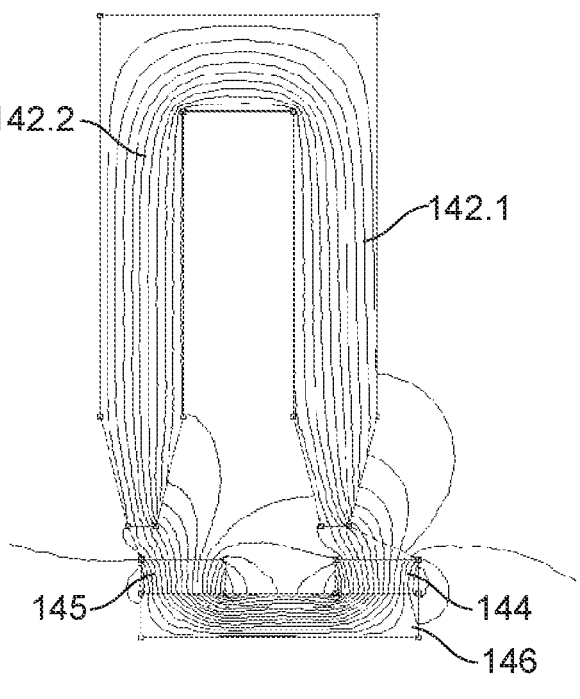

In contrast in the arrangement of FIGS. 11C and 11D, each of the bearing stator legs 142.1, 142.2 of the bearing stator 142 taper inwardly proximate an end of the bearing stator leg, thereby forming a truncated tip adjacent the air gap. Consequently, radial movement of the rotor shown in FIG. 11D causes a change in reluctance, leading to a restoring force and hence an increase in radial stiffness.

The tapering can be towards a centreline of magnetic bearing member and is typically configured so that a radial restoring force from an individual bearing increases as the rotor is radially offset from a central radial position.

Thus, selecting the geometry of the bearing stator legs 142.1, 142.2, or magnetic bearing material 144, 145 so the flux path changes significantly with radial movement, can increase the radial stiffness of the magnetic bearing.

An example of a comparison between the axial and radial stiffnesses for the arrangements of FIGS. 11A to 11D are shown in FIGS. 12A to 12D.

Figure 12A:
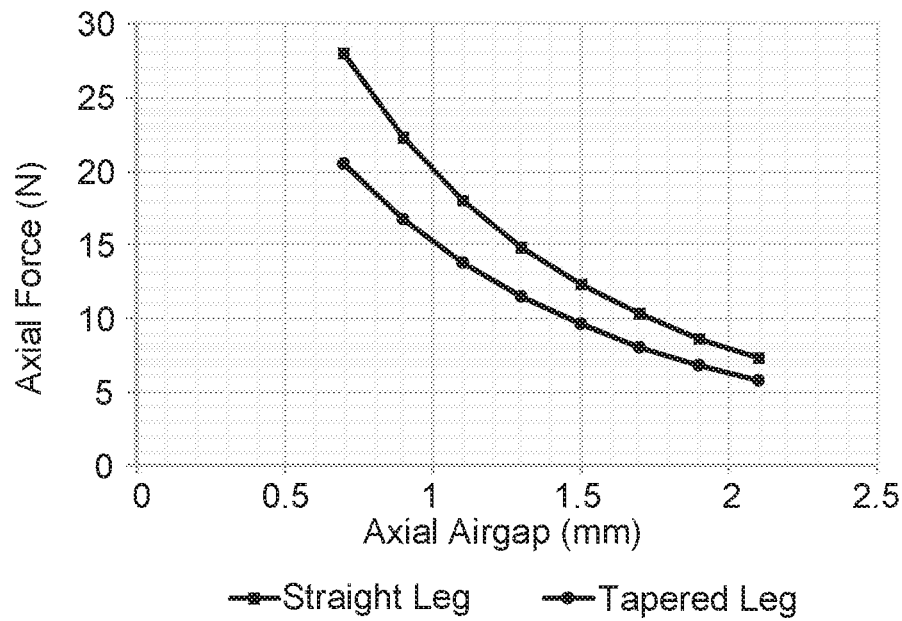
FIGS. 12A and 12B are graphs illustrating the relative axial and radial forces for different axial and radial positions of example magnetic bearings including tapered and untapered stator legs having matched radial stiffness and airgap.
Figure 12B:
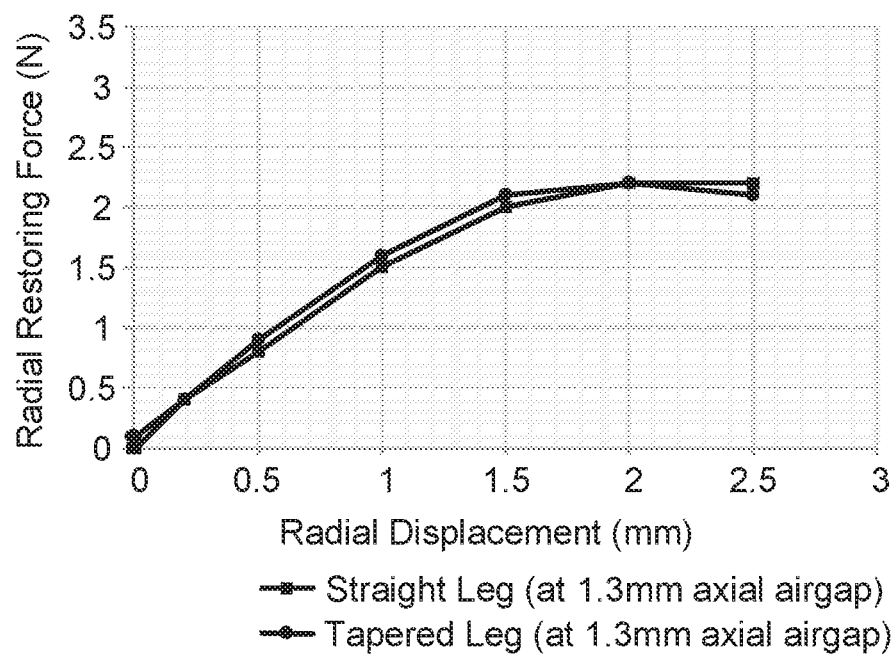

In the example of FIGS. 12A and 12B, the radial stiffnesses and axial airgap of the two designs are matched, leading to the straight bearing stator leg arrangement of FIG. 11A having a greater axial stiffness, and hence lower stiffness ratio. Example properties are summarized below in Table 4. An example of a high stiffness and high balance force bearing design is described in the right column of Table 4.

TABLE 4

| | Tapered Bearing stator leg | Straight Bearing stator leg | High stiffness stator design |
|---|---|---|---|
| Airgap | 1.3 mm | 1.3 mm | 1.3 mm |
| Balance force at airgap | 11.5N | 14.8N | 24.5N |

TABLE 4-continued

|  | Tapered Bearing stator leg | Straight Bearing stator leg | High stiffness stator design |
|---|---|---|---|
| Axial stiffness from magnetic bearing | 10.5 N/mm | 14.3 N/mm | 20.5 N/mm |
| Radial stiffness from magnetic bearing | 1.51 N/mm | 1.47 N/mm | 4 N/mm |
| Ratio | 14.4% | 10% | 19% |

Figure 12C:
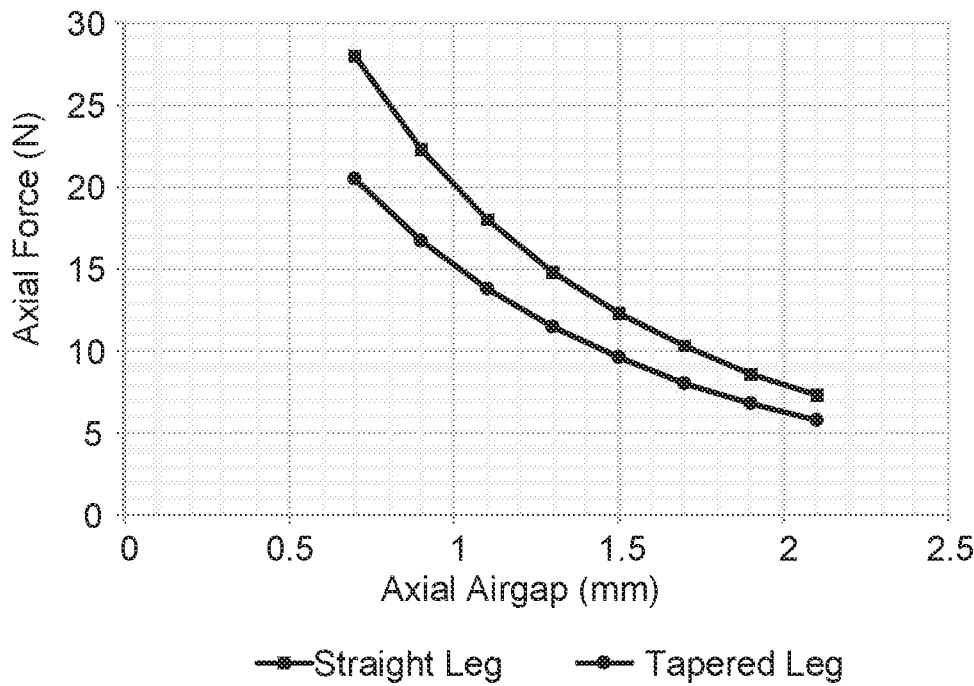
FIGS. 12C and 12D are graphs illustrating the relative axial and radial forces for different axial and radial positions of example magnetic bearings including tapered and untapered stator legs having matched axial forces.
Figure 12D:
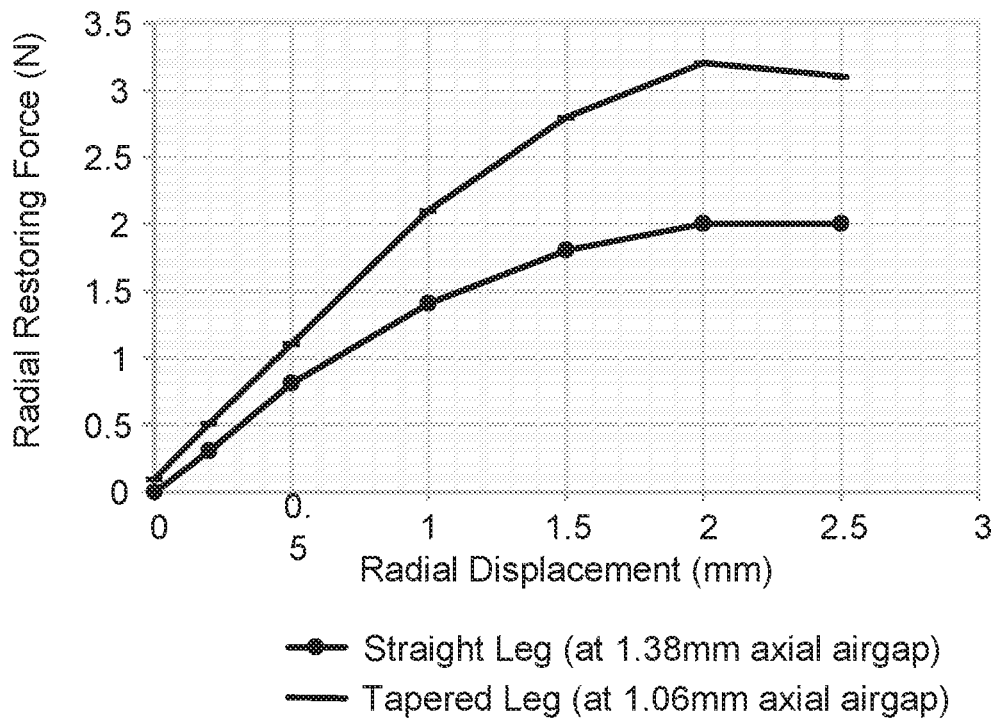

In the example of FIGS. 12C and 12D, the axial balance forces generated by the bearings are matched by analyzing the two designs for specific axial airgaps, leading to the tapered bearing stator leg arrangement of FIG. 11C having a greater radial stiffness, and hence higher stiffness ratio. Example properties are summarized below in Table 5. This equivalency of the axial balance forces can be achieved in the device by offsetting the bearing axial location relative to each other or by modifying the strength or volume of the permanent magnet material. An example of a high stiffness and high balance force bearing design is described in the right column of Table 5.

TABLE 5

|  | Tapered Bearing stator leg | Straight Bearing stator leg | High stiffness stator design |
|---|---|---|---|
| Airgap | 1.06 mm | 1.38 mm | 1.3 mm |
| Balance force at airgap | 14N | 14N | 24.5N |
| Axial stiffness from magnetic bearing | 14.5 N/mm | 14.3 N/mm | 20.3 N/mm |
| Radial stiffness from magnetic bearing | 2 N/mm | 1.41 N/mm | 4 N/mm |
| Ratio | 13.8% | 10% | 19% |

Figure 13:
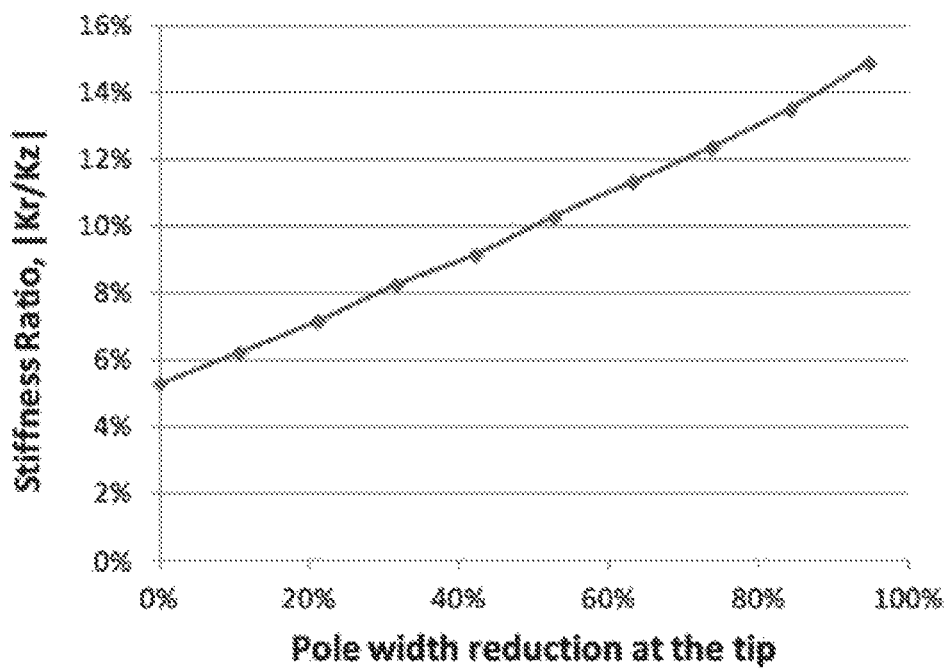
FIG. 13 is a graph illustrating a change in stiffness ratio for different amounts of bearing stator leg tapering.

An indication of the increase in stiffness ratio (radial to axial stiffness) that can be achieved by tapering the tip of the bearing stator legs 142.1, 142.2 is shown in FIG. 13, which highlights an approximately linear increase in stiffness ratio, with decreasing pole width.

Figure 14:
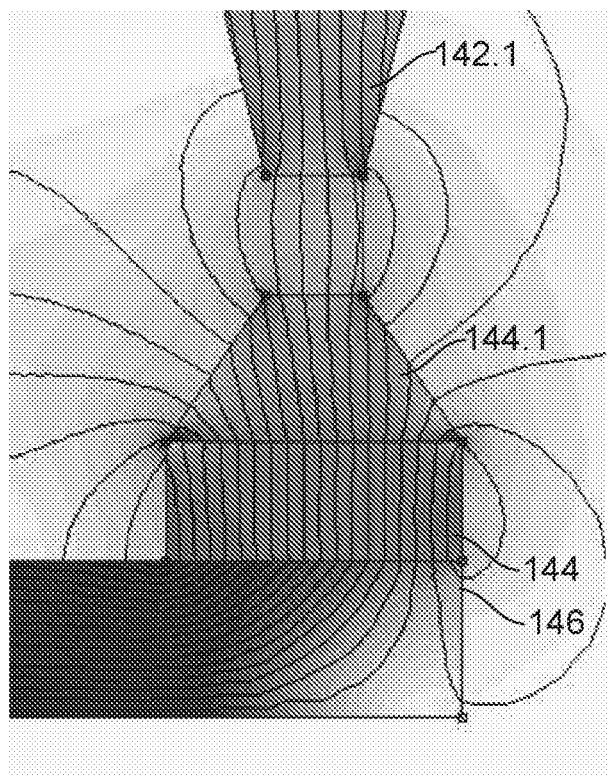
FIG. 14 is a schematic side view illustrating magnetic bearing flux for a magnetic bearing including a pole shoe.

Tapering can also be achieved through other mechanisms. For example, whilst tapering of magnets is achievable, this tends to be difficult, in terms of manufacture of the magnet, and not particularly effective. Alternatively however, tapering of the bearing magnetic material within the rotor can be achieved by forming the material from soft iron, or by placing a pole shoe 144.1 on the permanent magnet 144 as shown in FIG. 14.

It will be appreciated from the above that a variety of different configurations of bearing stator and magnetic material can be used, and that these will result in different stiffness ratios. A number of examples are shown in FIGS. 15A to 15F.

Figure 15A:
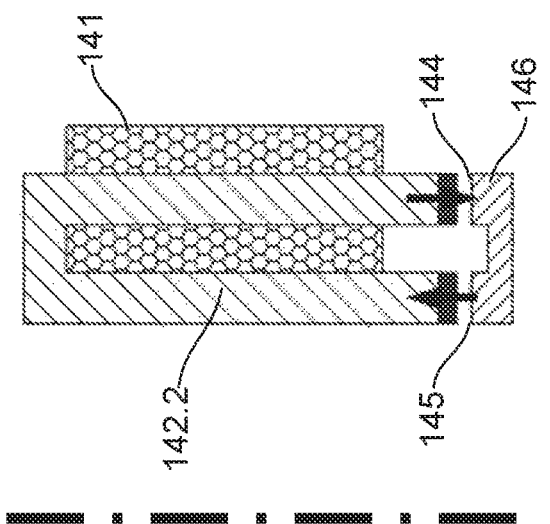
FIGS. 15A to 15F are schematic side views of different examples of bearing configuration.

In the example of FIG. 15A, the bearing magnetic material 144, 145 in the rotor includes two magnets mounted on a common bearing rotor yoke 146, whilst the bearing stator 142 includes bearing stator legs 142.1, 142.2 terminating in flat ends, leading to a stiffness ratio of |Kr/Kz|=5.3%.

Figure 15B:
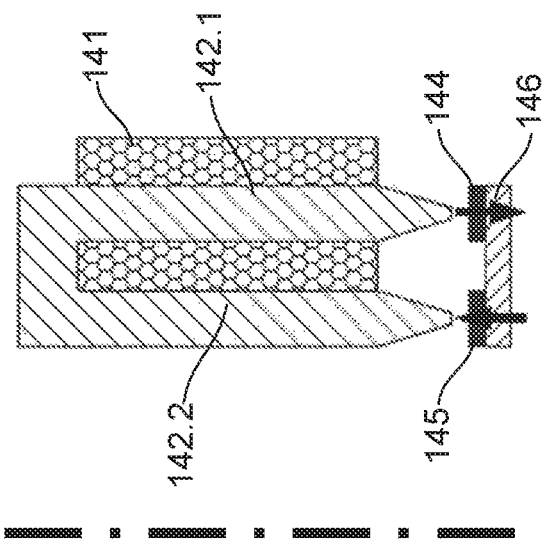

In the example of FIG. 15B, the bearing magnetic material 144, 145 in the rotor includes two magnets mounted on a common bearing rotor yoke 146, whilst the bearing stator 142 includes bearing stator legs 142.1, 142.2 terminating in tapering tips, leading to a stiffness ratio of |Kr/Kz|=12.9%.

Figure 15C:
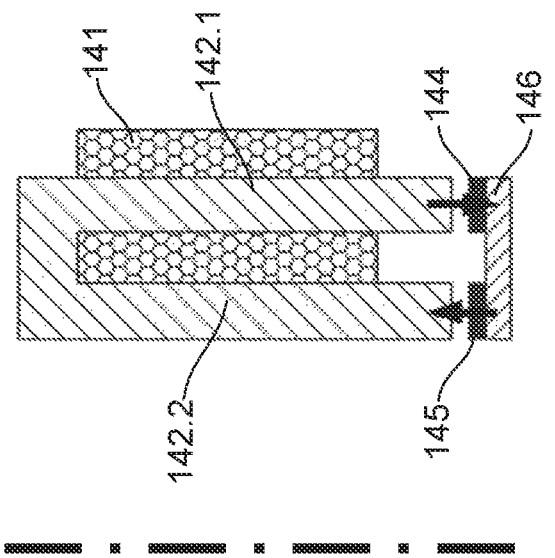

In the example of FIG. 15C, the bearing magnetic material 144, 145 in the rotor includes soft iron integrally formed with a common bearing rotor yoke 146, whilst the bearing stator 142 includes bearing stator legs 142.1, 142.2 terminating in permanent magnets, leading to a stiffness ratio of |Kr/Kz|=5.4%.

Figure 15D:
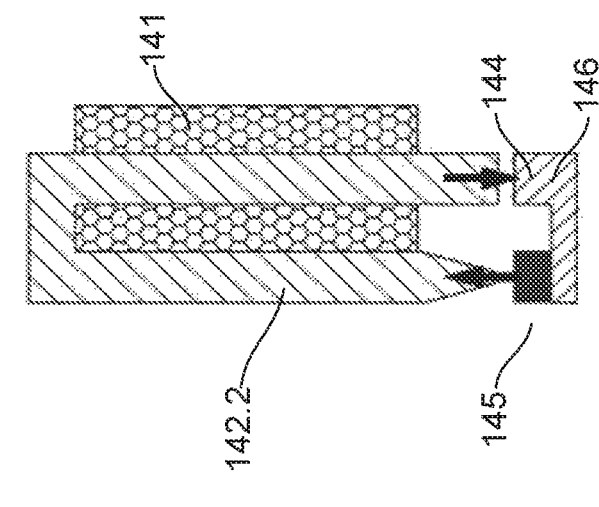

In the example of FIG. 15D, the bearing magnetic material 144 includes a permanent magnet, whilst the magnetic material 145 is soft iron integrally formed with the common bearing rotor yoke 146, whilst the bearing stator 142 includes bearing stator leg 142.1 terminating in a flat end and a permanent magnet mounted on an end of the second bearing stator leg, 142.2 leading to a stiffness ratio of |Kr/Kz|=6.6%.

Figure 15E:
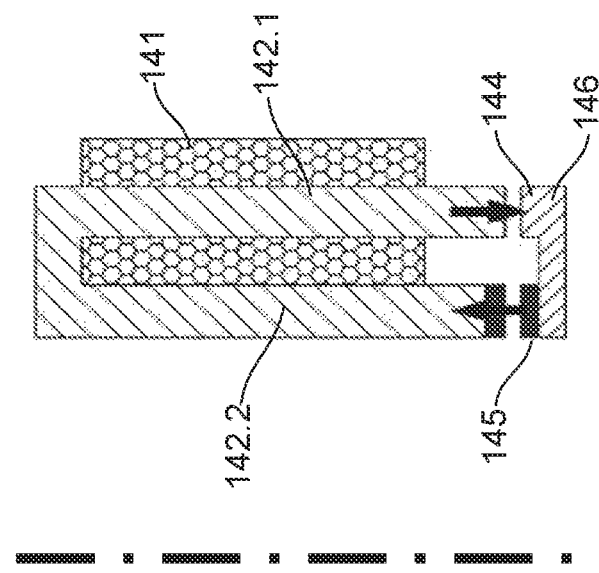

In the example of FIG. 15E, the magnetic material 145 and second bearing stator leg 142.2 include permanent magnets, whilst the first magnetic material and stator bearing stator leg 142.1, terminate in flat ends, leading to a stiffness ratio of |Kr/Kz|=15.5%.

Figure 15F:
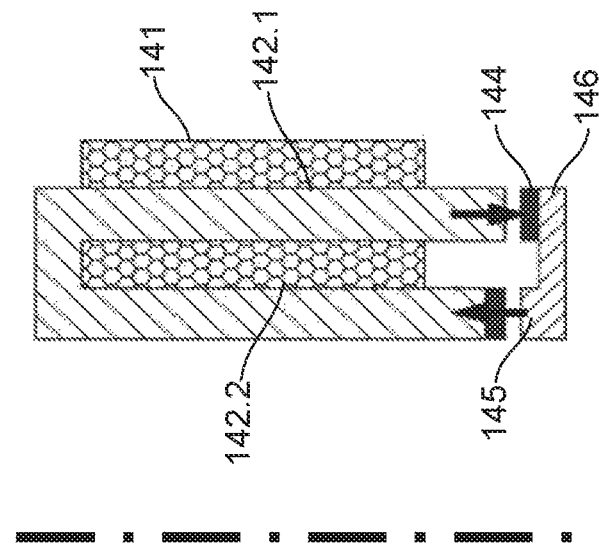

In the example of FIG. 15F, the bearing magnetic material 145 includes a magnet in opposition with a tapered tip on the second bearing stator leg 142.2, whilst the first magnetic material and bearing stator leg 142.1 terminate in flat ends, leading to a stiffness ratio of |Kr/Kz|=11.0%.

Whilst the arrangement of FIG. 15E provides the highest stiffness ratio, the axial force generated by this arrangement is approximately 40N, which is too high to allow for the passive forces to be balanced by the drive. Hence this arrangement cannot be used in practice. The alternative embodiments of FIGS. 15B and 15F however provide a sufficiently high stiffness ratio and an acceptable axial force.

The arrangements of FIGS. 15B and 15F have different benefits in terms of the sensors 160 that can be used.

The arrangements of FIGS. 15C, 15D and 15E have permanent magnets placed directly on the magnetic stators which can lead to manufacturing challenges as well as the potential for localized heating from the coils which can be detrimental to the magnet performance.

In this regard, the arrangement of FIG. 15B is used with the eddy current sensors 160 shown in FIGS. 2G to 2I, which includes three sensors, each having a coil mounted in a housing 163, circumferentially spaced and aligned with the inner bearing stator leg 142.2 of the magnetic bearing stators 142. The coil is aligned perpendicularly with a rotor surface and generates a magnetic field, which in turn induces eddy currents in a conductive target provided as part of the rotor 121. The eddy currents generate variations in the magnetic field, which are a function of the magnetic field, material properties and the position of the target. As a result, measurement of the field variations can be used to determine separation of the sensor 160 and the target, and hence the rotor 121. In one example, the target is formed from a metal surface that encapsulates the rotor to provide a hermetic biologically inert barrier, although this is not essential and alternatively a conductive target can be embedded within the rotor.

The pump housing also typically includes a barrier material designed to provide a hermetic barrier between the blood in the pump cavity and the magnetic bearing and motor elements, as well being biologically appropriate for continuous contact with blood. This is typically achieved with the use of metal, ceramic or other appropriate materials. The use of nonconductive and nonmagnetic barrier material such as ceramic in proximity to the eddy current sensor allows the magnetic field from the sensor to pass through the casing barrier and interact with the target in the rotor. However, the use of a conductive metal barrier material in proximity to the eddy current position sensors can reduce the field that can penetrate through the barrier material and interact with the target material reducing the sensitivity of the sensor to movement of the target and hence rotor. In the instance of a conductive barrier material being used, the design of the barrier and rotor target greatly affects the relative creation of the eddy currents in the materials and therefore the sensitivity of the sensor to the target movement. A sensor with high sensitivity reduces noise induced into the system, thereby reducing the power consumption of the active magnetic bearing system as well as improving the levitation performance.

Additionally, if the target material is designed such that the sensor magnetic field can penetrate through the target, care must be taken regarding the design and conductivity of the materials behind the target since they could erroneously influence the sensor signal. For example, if the sensor field can penetrate through the target material of the rotor it could interact with the magnetic bearing members located behind it. Since the magnetic bearing members form a non-homogeneous target in the radial direction, this could cause the sensor to erroneously detect radial movement of the rotor as axial displacement. As such where possible the target should be design such that the penetration of the sensor field through the target is minimized.

Accordingly, it will be appreciated that the sensitivity of the sensor system to axial target movement can be increased whilst the sensitivity to radial movement decreased, through the suitable selection of materials and the design of the barrier and target elements, as well as the sensor coil design and excitation frequencies, as will now be described.

In one example, the conductivity of the target is maximized to encourage the generation of eddy currents in that material and to minimize the skin depth of the magnetic field within the target material. Minimizing the skin depth of the eddy currents generated within the target, such that the skin depth is smaller than the target thickness, ensures that the sensor field is contained within the target and does not have significant penetration through to materials located past the target which can be a cause of erroneous changes in the signal. This can be achieved by using target materials of a relatively higher electrical conductivity, such as commercially pure Ti ($1.276 \times 10^6$ Siemens/m), than the barrier material as well as maximizing the thickness of the target material. At 1 MHz, 0.75 MHz and 0.5 MHz the skin depth of commercially pure titanium is about 0.45 mm, 0.52 mm and 0.63 mm respectively. The target material thickness is typically between 0.3 mm to 1 mm, and more typically approximately 0.6 mm. Increasing the barrier thickness also increases the operating axial airgap of the magnetic bearing stator reducing its performance.

The conductivity of the barrier material is typically minimized to reduce the generation of eddy currents in that material, and to maximize the skin depth of the eddy current generated within the material. To achieve sufficient penetration of the barrier material by the sensor field it should be ensured that the skin depth of the eddy currents generated in the barrier material is greater than at least two multiples of barrier material thickness, but preferably a multiple of 3 or more. This can be achieved by using materials of a relatively lower electrical conductivity, such as titanium alloy TiAlV ($5.800 \times 10^5$ Siemens/m), as well as decreasing the thickness of the target material while still providing sufficient barrier and structural strength. At 1 MHz, 0.75 MHz and 0.5 MHz the skin depth of TiAlV titanium is about 0.66 mm, 0.76 mm and 0.94 mm respectively. Typically the barrier material thickness is between 0.1 mm to 0.5 mm, and more typically approximately 0.3 mm.

In one example, an excitation frequency can be selected that ensures the eddy current skin depth in the barrier material is at least larger than twice the barrier thickness to allow penetration, whilst reducing the skin depth of the eddy currents in the target material such that it is equal or smaller than the target thickness. An optimum frequency can be selected such that the trade-off between the target thickness and material and barrier thickness and material results in a maximum raw signal strength. In one example, the coil excitation frequency is between 0.2 MHz and 2 MHz, and more typically is approximately 1 MHz. Higher frequencies can reduce the eddy current skin depth in the barrier material such that there is insufficient penetration of the field into the target, while lower frequencies cannot produce sufficient eddy currents in the target material reducing the sensitivity of the signal to rotor axial movement.

The sensor radial location should also be considered such that radial movement of the rotor through its radial range does not change the shape or material properties of the target. The sensor should be located sufficiently away from edges or features of the target material such that movement of the rotor radially will not introduce those elements into the sensor field. For example an annular target with an inner radius of 12.5 mm and an outer radius of 25 mm which is targeted by a sensor probe with a diameter of 6.2 mm located at a radial location of 18.75 mm could afford 2 mm of radial movement of the target in either direction without letting the radial edge of the probe get within about 1.25 mm of the radial edge of the target, or 20% of the probe diameter. Probes with larger diameters can increase sensitivity when detecting targets at a larger axial distance, such as when the impeller is located close to the left end of the cavity in this application, compared to smaller probes. Sizing the probe such that it is the largest diameter for the available target width affords the best sensitivity of the system, particularly at larger axial separations. This is particularly applicable to sensor systems that utilize single sided detection rather than differential sensor topologies.

The sensor head design is typically configured to create a volumetric magnetic field that can penetrate the barrier material, whilst also interacting with the target material at the maximum target axial position. To achieve this, the sensor head diameter is typically between 2 mm and 7 mm and more typically approximately 6.2 mm, whilst the sensor head height being between 0.2 mm and 1.5 mm and more typically approximately 0.6 mm. The sensor coil typically has between 25 and 300 turns and more typically approximately 50 turns.

Example parameters for eddy current sensing are set out in Table 6 below.

TABLE 6

| Variable ID | Description | Range | Optimum | Unit |
|---|---|---|---|---|
| $h_{target}$ | Thickness of target material | 0.2-0.6 | 0.6 | mm |
| $h_{barrier}$ | Thickness of barrier material | 0.1-0.3 | 0.3 | mm |
| $\sigma_{target}$ | Electrical conductivity of the target material | 5.800E+05-2.239E+07 | 1.276E+06 | Siemens/m |
| $\sigma_{barrier}$ | Electrical conductivity of the barrier material | 0-1.276E+06 | 5.800E+05 | Siemens/m |
| $f_{exc}$ | Sensor excitation frequency | 0.2-2 | 1 | MHz |
| $d_{coil, o}$ | Outer diameter of the sensor coil | 2-7 | 6.2 | mm |
| $h_{coil, o}$ | Height of the sensor coil | 0.2-1.5 | 0.6 | mm |
| $N_{coil}$ | Turn number of sensor coil | 25-300 | 50 | turns |

These parameter variations allow for the design of the eddy current sensor system to operate while satisfying the manufacturing, assembly and biological requirements of the rotor and casing.

In contrast, in the arrangement of FIG. 15F the first bearing material is formed from a soft iron material, which can be more suitable for other sensing arrangements, such as reluctance sensors or the like.

An advantage of reluctance sensors is their ability to operate at excitation frequencies significantly lower than eddy current position sensors. Operation at lower excitation frequencies means less eddy currents are created in the casing barrier materials and rotor conductive materials, reducing their influence on the sensor performance allowing greater flexibility in the system design and materials. Sensors operating at higher frequencies require specialized cables, such as coaxial cables to provide a stable conductor impedance between the sensor electronics and the sensor itself. Operation at a lower frequency allows for the use of simpler twisted pair wire connection, which can be smaller than coaxial cables and more tolerant to environmental influences. Operation at a lower frequency can simplify the generation of the excitation signal as well as signal processing of the resulting signal that contains the position information.

If the sensor is designed to operate at a high frequency, a coaxial cable may be required to connect the sensor head with the electronics. Coaxial cables and connections are known to suffer from the disadvantages of interference in the hostile body environment and the external influences during patient activity, in particular, the bend flexing due to breathing amongst others. To mitigate the issue of coaxial cabling interference, the parts or all of the electronics for the sensor can be included on the pump. Thus, a conditioned analog or digital signal can be transmitted from the device to an external controller, which has a higher threshold against interference. However, should these implanted electronics fail, the magnetic bearing system would cease to function, and the device would continue operation on the hydrodynamic backup bearing. To restore the magnetic bearing function in this instance however, the entire device would need to be replaced as opposed to just the external control box.

However, it will be appreciated that the arrangement of FIG. 15B, which results in a higher stiffness ratio, may be preferred in which case eddy current sensing may be used.

As also mentioned above, whilst tapering is one mechanism to achieve a width difference between the bearing stator legs 142.1, 142.2 and magnetic bearing members 144, 145, this is not essential and alternatively either or both of the bearing stator legs 142.1, 142.2 could be narrowed relative to the magnetic bearing members 144, 145 over the entire length of the bearing stator legs 142.1, 142.2. However, the use of the tapering is generally preferred as this allows the poleface of the magnetic bearing members 144, 145 to be narrower whilst not affecting flux saturation in the stator legs due to flux linkage/leakage between the stator legs, which in turn reduces the overall physical size, which is important in heart pump applications.

Bearing Maximum Force

The maximum force that can be produced is determined as the maximum force that is achieved when the bearing stator material saturates with magnetic flux.

Because the magnetic flux density in the foot of the straight bearing stator leg is typically lower than in other parts of the stator (due to leakage between the bearing stator legs in the upper region), tapering the foot/tip of the bearing stator leg does not significantly reduce the maximum force that can be created.

Bearing Efficiency

The efficiency of the magnetic bearing is dependent on the amount of area filled with coils. As such to maximize the efficiency of the magnetic bearing, the tallest magnetic bearing allowable by physical constraints should be used.

Figure 16A:
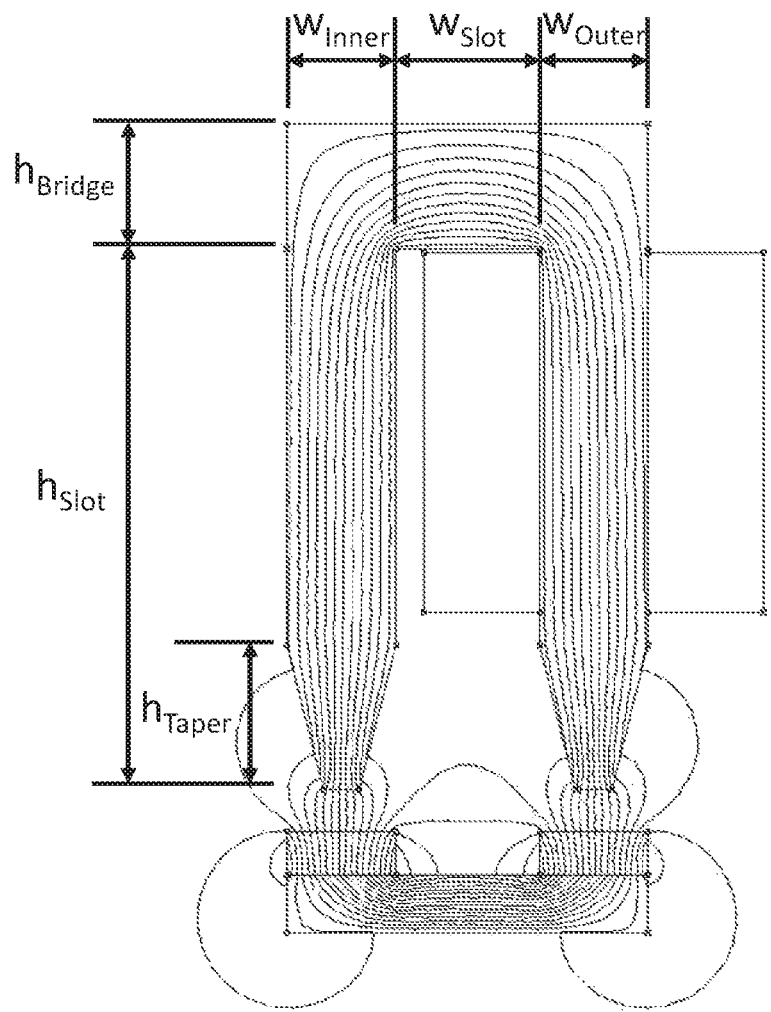
FIG. 16A is a schematic side view of an example of a bearing illustrating different bearing parameters.
Figure 16B:
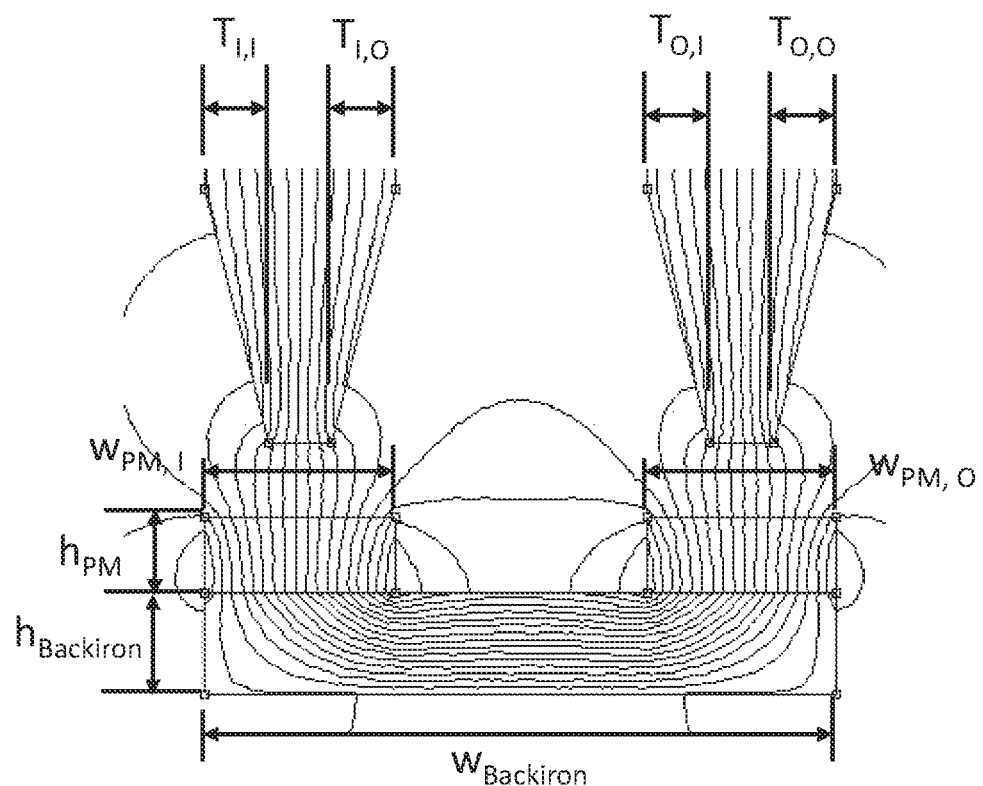
FIG. 16B is a schematic close up side view of part of the bearing of FIG. 16A illustrating further bearing parameters.

Examples of bearing parameters for the parameters shown in FIGS. 16A and 16B are outlined in Table 7 below:

TABLE 7

| Variable ID | Description | Range | Optimum | Unit |
|---|---|---|---|---|
| $w_s$ | Bearing stator slot width | 3.5-5.5 | 4.7 | mm |
| $w_{Inner}$ | Second bearing stator leg width | 2-4 | 2.9 | mm |
| $w_{outer}$ | First bearing stator leg width | 2-4 | 3.6 | mm |
| $h_{Slot}$ | Bearing stator slot height | 5-35 | 14.8 | mm |
| $h_{Taper}$ | Taper height | 0-10 | 5 | mm |
| $h_{Bridge}$ | Bearing stator bridge height | 2-4 | 3.2 | mm |
| $T_{O, I}$ | Second bearing stator leg inner taper | 0-3 | 0.5 | mm |

TABLE 7-continued

| Variable ID | Description | Range | Optimum | Unit |
|---|---|---|---|---|
| $T_{O,O}$ | Second bearing stator leg outer taper | 0-3 | 1.6 | mm |
| $T_{O,I}$ | First bearing stator leg inner taper | 0-3 | 0.0 | mm |
| $T_{O,I}$ | First bearing stator leg outer taper | 0-3 | 2.8 | mm |
| $h_{PM}$ | Bearing magnet height | 1-3 | 2.4 | mm |
| $w_{PM,I}$ | Second bearing magnet width | 3-4.5 | 3.5 | mm |
| $w_{PM,O}$ | First bearing magnet width | 3-4.5 | 3.5 | mm |
| $K_{PM}$ | Magnet strength | N28H-N48H | N45H | — |
| $w_{backiron}$ | Rotor bearing yoke width | 10-13 | 11 | mm |
| $h_{backiron}$ | Rotor bearing yoke height | 1-2 | 1.9 | mm |
| $D_{stator}$ | Bearing stator depth | 6-10 | 8 | mm |

Accordingly, it will be appreciated from the above, that the ratio of the radial to axial stiffness can be manipulated by the design of the magnetic circuit elements in the bearing. In particular tapering of the highly permeable material near the airgap can be used to increase the stiffness ratio, whilst the location and geometry of permanent magnets can be used to influence the stiffness ratio and passive axial forces generated by the bearing. The stiffness ratio can be improved with these changes if they increase the change of reluctance for radial movement and/or decrease the change of reluctance for axial movement.

FIG. 9B shows the net force difference between the motor and magnetic bearing attractive forces. The axial system stiffness in this example is 37N/mm at the balance point. In practice, the heart pump typically has an axial system stiffness of at least one of: at least 10 N/mm, at least 20 N/mm, at least 30 N/mm, less than 60 N/mm, less than 50 N/mm, about 10-60 N/mm, about 25-50 N/mm, about 15-25 N/mm, about 30-40 N/mm and about 35-40 N/mm. In this example, almost all the radial system stiffness is generated by radial stiffness of the bearing with minimal contribution from the motor system, however in other configurations there can be a larger more significant contribution from the motor. The heart pump has a radial system stiffness of at least one of between 0.5 N/mm and 11 N/mm, between 0.5 N/mm and 1.5 N/mm, between 1.5 N/mm and 3.0 N/mm, between 3 N/mm and 6 N/mm and between 6 N/mm and 11 N/mm.

Combined Yoke

In the above examples, the rotor drive yoke 135 and rotor bearing yoke 146 are identified as separate elements. However, in practice the rotor drive and bearing yokes 135, 146 can be combined into a single monolithic annular element. The thickness, design and material of the combined rotor drive and bearing yoke can be modified from their independent standalone designs for improved performance as a combined system.

For example, when the rotor drive and bearing yokes 135, 146 are physically and sufficiently magnetically separated, the forces produced by the motor and magnetic bearing systems act on the rotor yoke elements independently, requiring the rotor drive and bearing yokes 135, 146 to be connected mechanically to transfer the forces and balance them. Combining the rotor drive and bearing yokes 135, 146 connects the force between the two magnetic systems thereby simplifying the rotor design. Manufacturing and assembly of the single combined rotor drive and bearing yoke can reduce tolerance stack-ups, improving the balance and levitation performance of the rotor. Cross-coupling between the motor and magnetic bearing flux through the combined rotor drive and bearing yoke can be minimized through the design of the combined yoke, such as the choice of thickness and material.

High purity iron is often used in the construction of the rotor drive and bearing yokes 135, 146 due to its high magnetic flux saturation level. Other materials such as Cobalt-Iron-Vanadium alloys (Hiperco 50A) can offer higher magnetic flux saturation levels so are particularly applicable to this application as they can reduce the volume of material required in the rotor yoke, therefore reducing the thickness of the rotor and the overall device thickness. This height reduction for a constant diameter can also improve the dynamics of the rotor. The combined rotor drive and bearing yoke can be constructed from a number of different materials with varying magnetic properties to create a yoke with non-homogeneous magnetic permeability. A material with low magnetic saturation level can be used within the combined rotor drive and bearing yoke to minimize cross-coupling between the two magnetic systems by increasing the magnetic reluctance path to flux flowing between the two sides.

On-line sensor recalibration

The known force characteristics of the magnetic bearing actuator at various axial airgaps can be used to verify the axial position of the rotor. Small sinusoidal perturbations of the magnetic bearing actuator current at a given low frequency will produce a movement in the rotor that is a function of the current stiffness and the axial position stiffness. Accurate knowledge of the change of current and axial position stiffness as a function of airgap can allow for the estimation of the airgap from the measured response from the perturbations. This measurement can occur while the device is operational since the perturbations are small. This information regarding the airgap obtained from the on-line perturbation method can be compared to the position data received from the position sensors to ensure there have been no changes in the system performance due to variation in the magnetic bearing levitation system, such as sensor calibration or permanent magnet strength.

The above described arrangements can be employed in wide range of circumstances and in different pump configurations. For example, this can be used when one or two pumps are used to provide assistance or replacement of the left or right ventricles, including in a TAH, when two rotary pumps to provide complete replacement of the native heart, in an LVAD/RVAD, when a single rotary pump is used to provide assistance to either the left or right ventricles, or in a BiVAD, when two rotary pumps to provide assistance to the left and right ventricles.

An example of a single VAD heart pump will now be described with reference to FIGS. 17A to 17F.

In this example, the heart pump 1700 includes a housing 1710 defining a cavity 1715. The housing can be of any suitable form but typically includes a main body, and left and right end caps which connect to the main body. The housing can be made of any suitable biocompatible material, and can be made of titanium, a polymer or the like.

The housing 1710 includes an inlet 1711, for connection to the left atrium/pulmonary vein or right atrium/vena cava, or left or right ventricle, and an outlet 1712 for connection to the aorta or pulmonary artery, respectively.

The heart pump 1700 includes an impeller 1720 provided within the cavity 1715. The impeller 1720 includes a rotor 1721 having vanes mounted thereon for urging fluid from the inlet 1711 to the outlet 1712 upon rotation of the impeller 1720. In this example, as the heart pump 1700 is a single ventricular assist device, the impeller includes a single set of vanes 1722 for urging fluid from the inlet 1711 to the outlet 1712. In this example, the vanes 1722 have a particular configuration although it will be appreciated that other suitable vane configurations can be used. The impeller can also include an aperture 1724 extending therethrough to allow blood to flow around the rear surface of the impeller and thereby prevent stagnation and clotting of blood within the heart pump. Furthermore, the use of a magnetic bearing in this region allows for blood gaps in excess of 200-300 µm, which can both reduces shear stress and thus red cell lysis, as well as promote greater rates of washout flow than otherwise anticipated in gaps created by hydrodynamic bearings.

The heart pump 1700 further includes a drive 1730 that rotates the impeller 1720 within the cavity 1715. The drive 1730 can be of any appropriate form but typically includes a number of coils 1731, each wound on a respective stator 1732, supported by a mounting 1733, allowing the drive 1730 to be coupled to the housing 1710. The drive cooperates with magnetic material 1734 mounted in the rotor 1721, with the magnetic material being in the form of a number of circumferentially spaced permanent drive magnets arranged proximate an outer circumferential edge of the rotor 1721. In one example, the coils 1731 and stators 1732 are wedge shaped and circumferentially spaced around the mounting 1733, so as to provide twelve electromagnets axially aligned with the drive magnets 1734 in the rotor 1721, to thereby maximise a degree of magnetic coupling between the magnets in the rotor 1721 and the drive 1730.

The heart pump 1700 can further include a magnetic bearing 1740 including at least one bearing coil 1741 that controls an axial position of the impeller within the cavity 1715. In one particular example, shown in more detail in FIG. 17E, the magnetic bearing includes three bearing coils 1741, each of which is mounted on a first arm 1742.1 of respective U-shaped stators 1742, with a second arm 1742.2 being positioned radially inwardly of the first arm 1742.1. The stators 1742 are mounted to or integrally formed with a support 1743 and circumferentially spaced 170° apart around the housing so that the first and second arms 17421. 1742.2 align with respective magnetic material, such as bearing magnets 1744, 1745 within the impeller 1720, allowing an axial position of the impeller 1720 to be controlled.

In one particular example, the bearing rotor assembly includes ferromagnetic core target 1744 mounted in the rotor, proximate an outer circumferential edge of the rotor 1721, and a permanent bearing magnet or ferromagnetic material 1745 mounted radially inwardly of the first ferromagnetic core target 1744, so that the ferromagnetic core target and bearing magnets 1744, 1745 align with respective arms 1742.1, 1742.2 of the stators 1742. The ferromagnetic core target can be replaced with a second permanent magnet. However, the use of a magnetic bearing may not be required and can be replaced by a static physical bearing or hydrodynamic bearing, or the like.

Figure 17A:
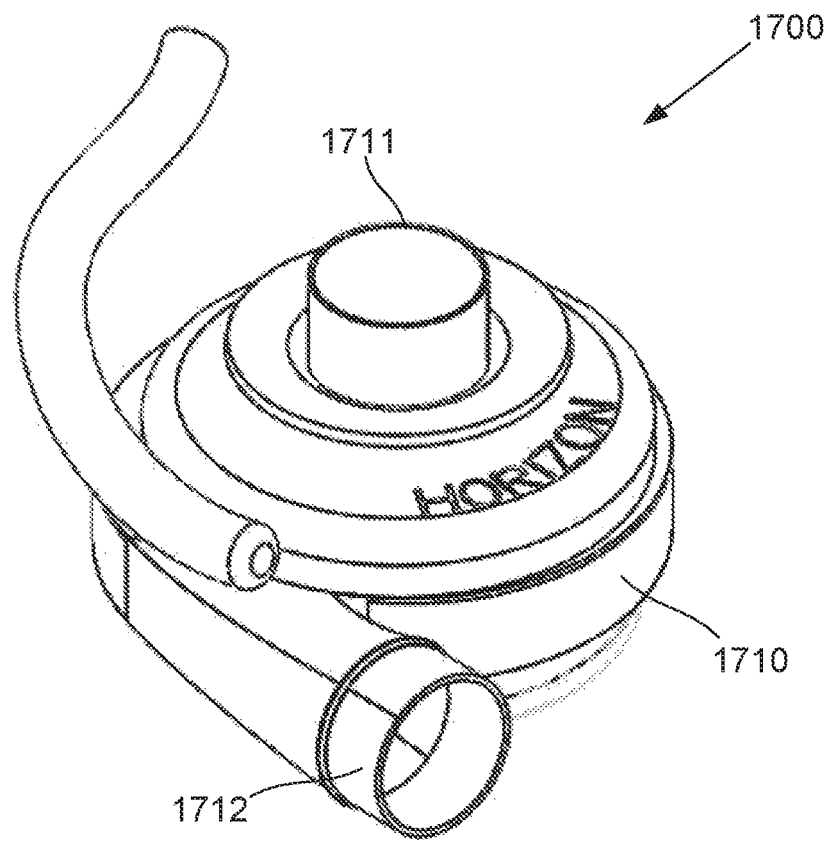
FIG. 17A is a schematic perspective view of an example of a single VAD heart pump.
Figure 17B:
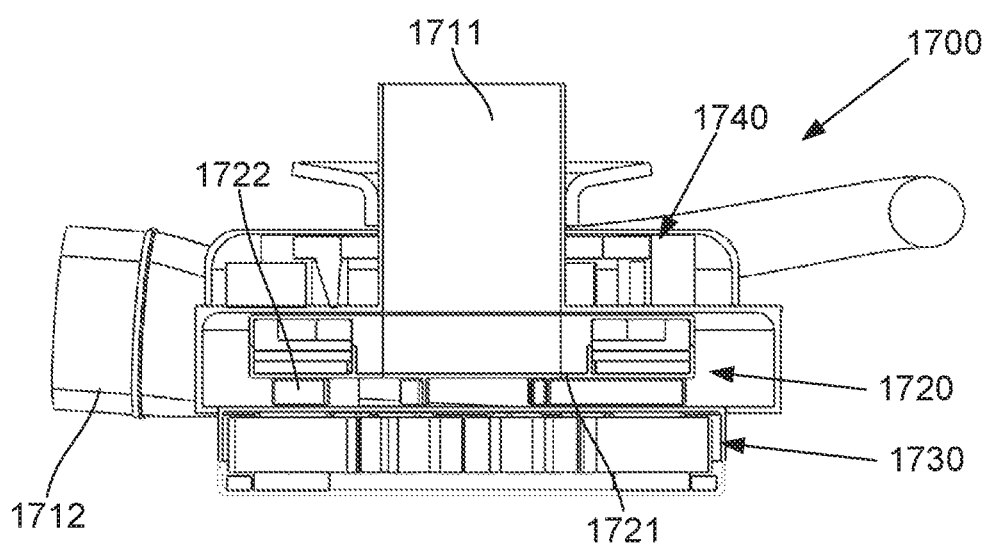
FIG. 17B is a schematic cutaway side view of the heart pump of FIG. 17A.
Figure 17C:
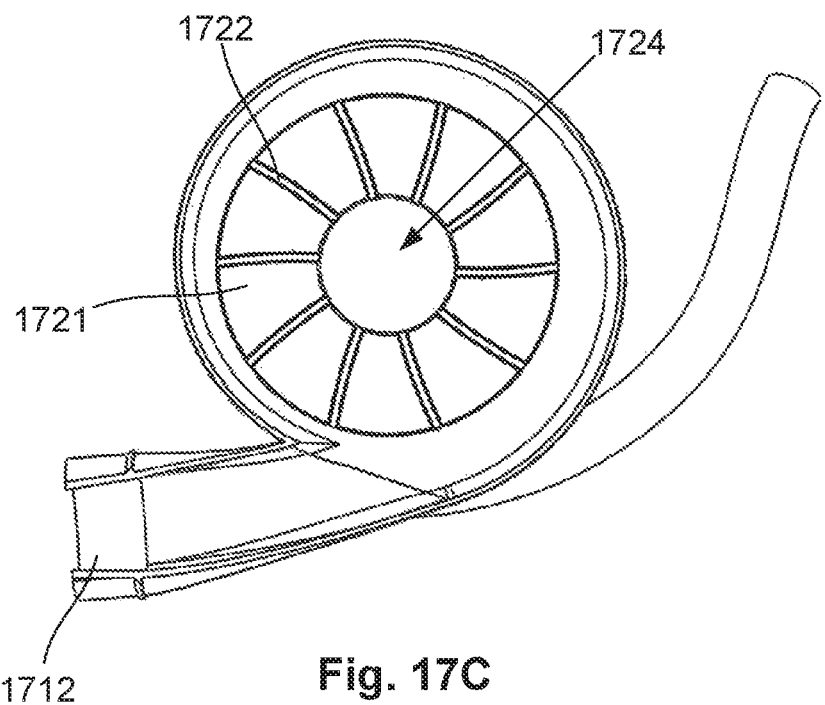
FIG. 17C is a schematic cutaway plan view of the heart pump of FIG. 17A.
Figure 17D:
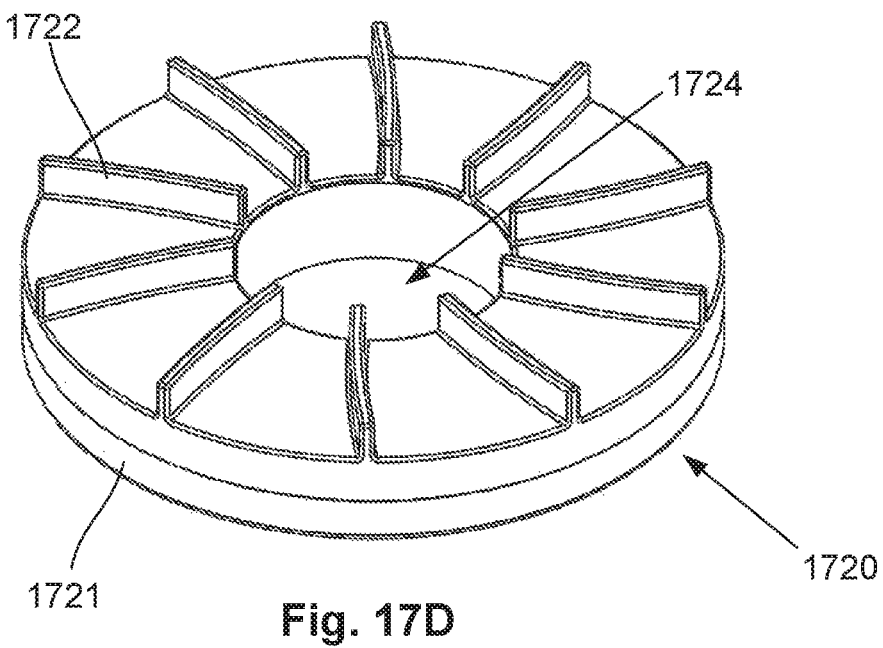
FIG. 17D is a schematic perspective view of the impeller of the heart pump of FIG. 17A.
Figure 17E:
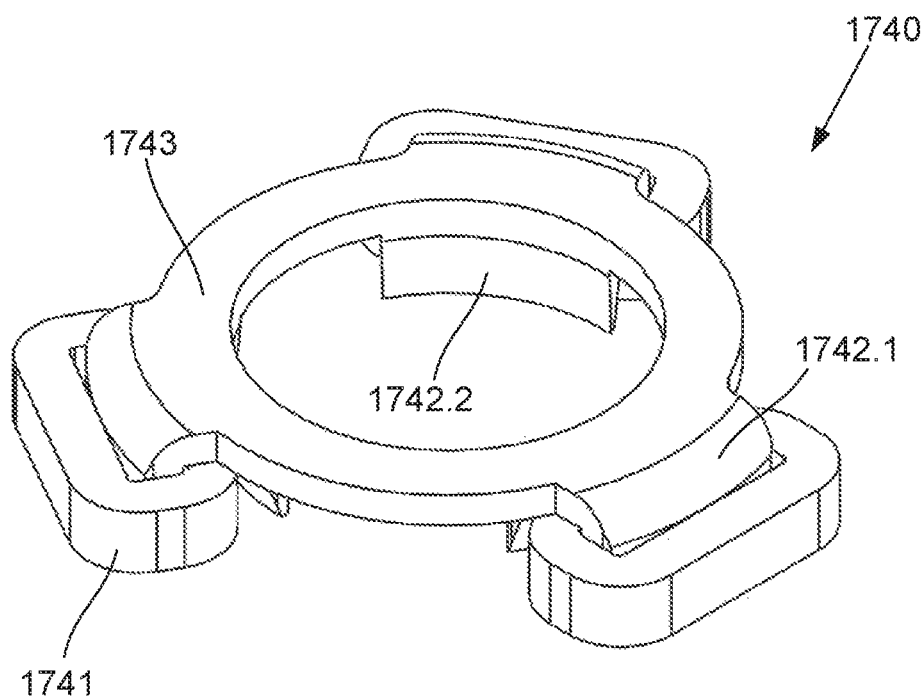
FIG. 17E is a schematic perspective view of the magnetic bearing of the heart pump of FIG. 17A.
Figure 17F:
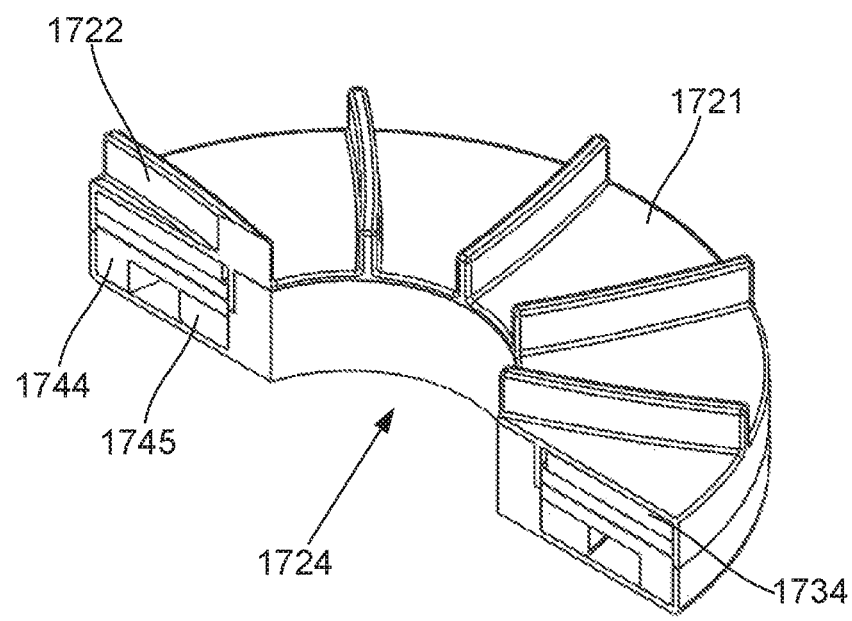
FIG. 17F is a schematic cutaway perspective view of the impeller of FIG. 17A.

In this example, the drive 1730 and magnetic bearing 1740 are mounted at opposing ends of the housing 1710 so that the drive and bearing 1730, 1740 are provided proximate opposing surfaces of the rotor 1721 as shown for example in FIG. 17B. In the current example the drive 1730 is mounted adjacent the side of the impeller 1720 that includes vanes so as to maximise the blood gap between the rotor, vanes and the casing. That is to say, only the vane tips are in closer proximity to the casing, however this blood gap can still be in the order of 200-300 µm. Additionally, bearing and drive are configured so that the magnetic forces inherent between the drive 1730 and impeller 1720, and between the magnetic bearing 1740 and impeller 1720 and the hydraulic forces on the impeller 1720 define a balance position within the cavity under conditions of normal flow. This minimises the bearing power required to maintain the position of the impeller 1720 within the cavity under nominal flow conditions.

It will be appreciated as in the previous example, the apparatus can further include a controller, and otherwise functions largely as previously described, and hence will not be described in further detail.

Additionally, the above described arrangement can be employed in a pump which had one or more combinations of different bearing types, for example, contact bearings, passive magnetic bearings and hydrodynamic bearings. Each of these bearing types have a axial force requirement for their operation and can benefit from design concepts described above.

The heart pump can be used with a controller and control process that uses an active magnetic bearing in conjunction with a zero power controller that controls the position of the rotor in response to a change of magnetic bearing current, or that uses speed control based on impeller position, for example in response to a perturbation in flow/bearing operation to provide an additional degree of control over flow.

For example, the above described heart pump can be configured to operate using a fall-back hydrodynamic bearing in the event that the axial active magnetic bearing fails, and an example of this will now be described in more details with reference to FIGS. 18A to 18C.

Figure 18A:
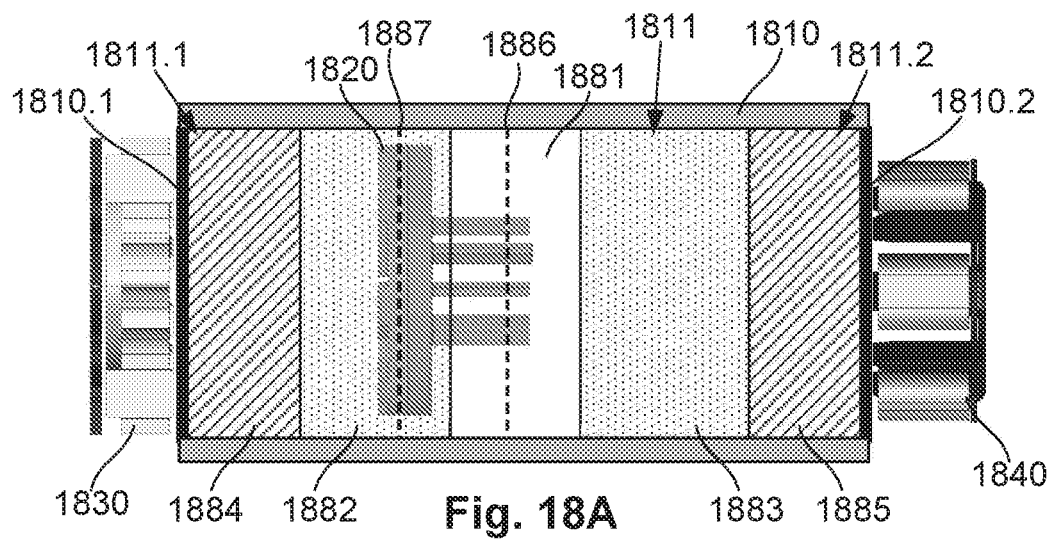
FIG. 18A is a schematic diagram of an impeller cavity with the impeller in a passive balance position.
Figure 18B:
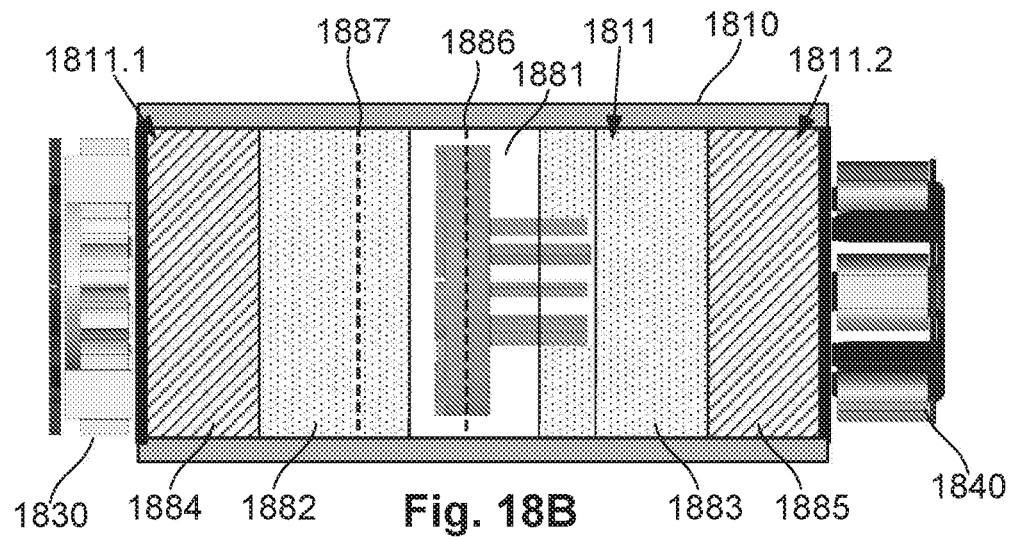
FIG. 18B is a schematic diagram of an impeller cavity with the impeller in a working position.
Figure 18C:
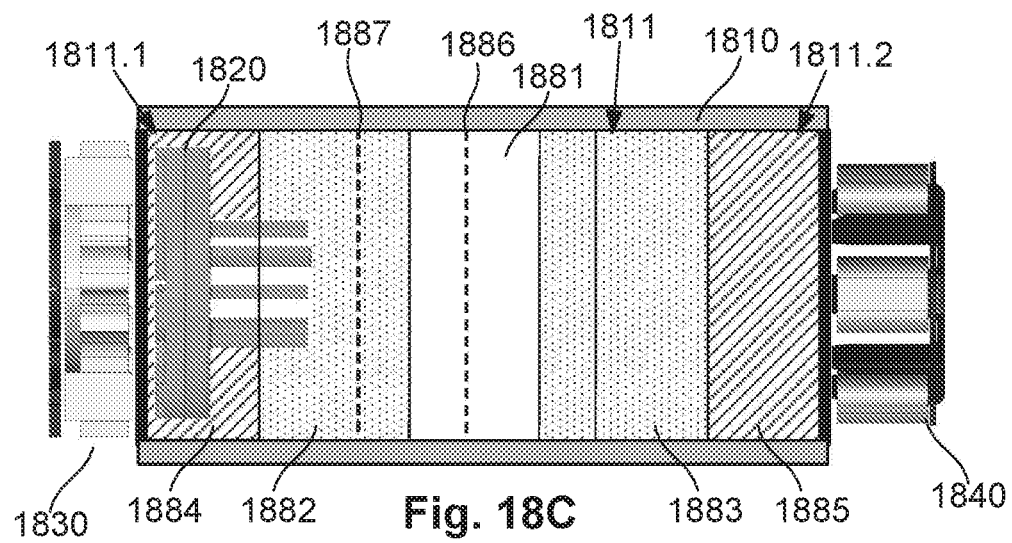
FIG. 18C is a schematic diagram of an impeller cavity with the impeller in a back-up hydrodynamic bearing position.

In particular, FIGS. 18A to 18C show an impeller cavity 1811 defined by a housing 1810 with an impeller 1820 positioned therein. A drive 1830 is provided at a left end 1811.1 of the cavity, adjacent a left end wall 1810.1 whilst a magnetic bearing 1840 is provided on a right end 1811.2 of the cavity adjacent a right end wall 1810.2, with the cavity being approximately 600 µm in length in one example. It will therefore be appreciated that this configuration is generally similar to that described above with reference to FIGS. 1A to 3D. It will be noted that the terminology left and right ends of the cavity refers to the left and right as orientated in the drawings, but also refers to the respective functionality of the pump, with the left side of the cavity acting to provide left ventricular function and the right side of the cavity acting to provide right ventricular function.

The cavity can be considered as delineated into a number of zones, including a normal working region 1881, left and right buffer zones 1882, 1883 and left and right end zones 1884, 1885.

In the absence of hydraulic forces, a minimum power balance position is shown in FIG. 18A coincident with the dotted line 1887. At this position, absent of hydraulic forces, the attractive forces of the drive and bearing balance so that only a small amount of bearing current would be required in order to balance small disturbance forces and maintain the impeller 1820 at the balance position 1887.

In practice, under normal operating conditions with hydraulic forces present within the cavity, the impeller 1820 is provided near the geometric centre of the cavity 1886, typically within the working range zone 1881. In this instance, the attractive forces of the drive and bearing, together with the hydraulic forces, balance so that theoretically no bearing current would be required in order to maintain the impeller 1820 at the balance position 1886, in use.

Nevertheless, it will be appreciated that the impeller 1820 will move left or right within the cavity depending on the particular hydraulic forces, with the movement typically being constrained to within the working zone 1881 under normal conditions.

In the event of a magnetic bearing failure, the impeller 1820 will typically be attracted to either the left or right hand ends 1811.1, 1811.2 of the cavity 1811 due to magnetic attraction by the drive 1830 or bearing 1840 respectively, depending on factors, such as the position of the impeller 1820 and the prevailing hydraulic conditions at the time of failure.

In the event that the impeller is attracted to the cavity left end 1811.1 as shown in FIG. 18C, through appropriate configuration of the impeller 1820, an upper surface of the impeller vanes can act as a hydrodynamic bearing, allowing the impeller 1820 to continue rotating without physically engaging the housing 1810. In this regard, the hydrodynamic bearing results from a thin fluid film between the upper surface of the left impeller blades and the left end wall 1810.1, which arises due to the impeller blades having a sufficiently large surface area and pitched surface, to cause fluid build-up between the blade surface and the left end wall 1810.1.

Figure 19A:
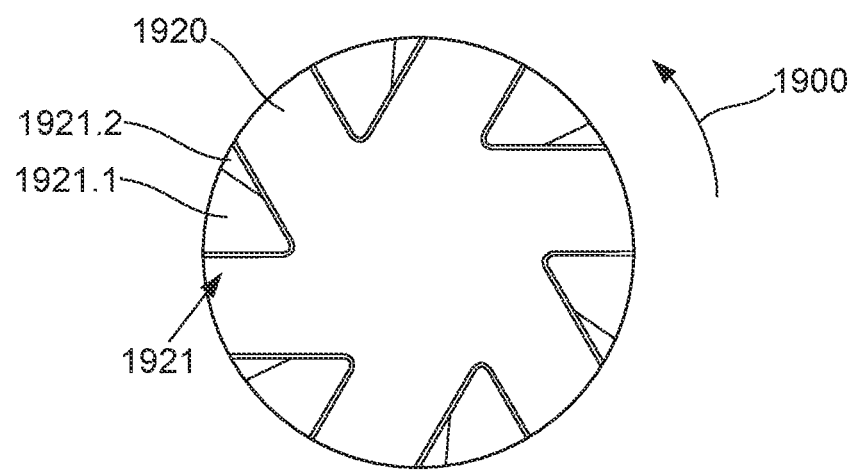
FIG. 19A is a schematic plan view of the impeller configuration to provide a hydrodynamic bearing.
Figure 19B:
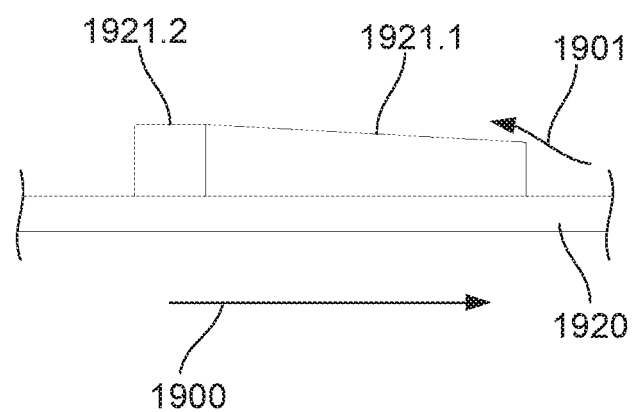
FIG. 19B is a schematic side view of one of the impeller vanes of the impeller of FIG. 19A.
Figure 19C:
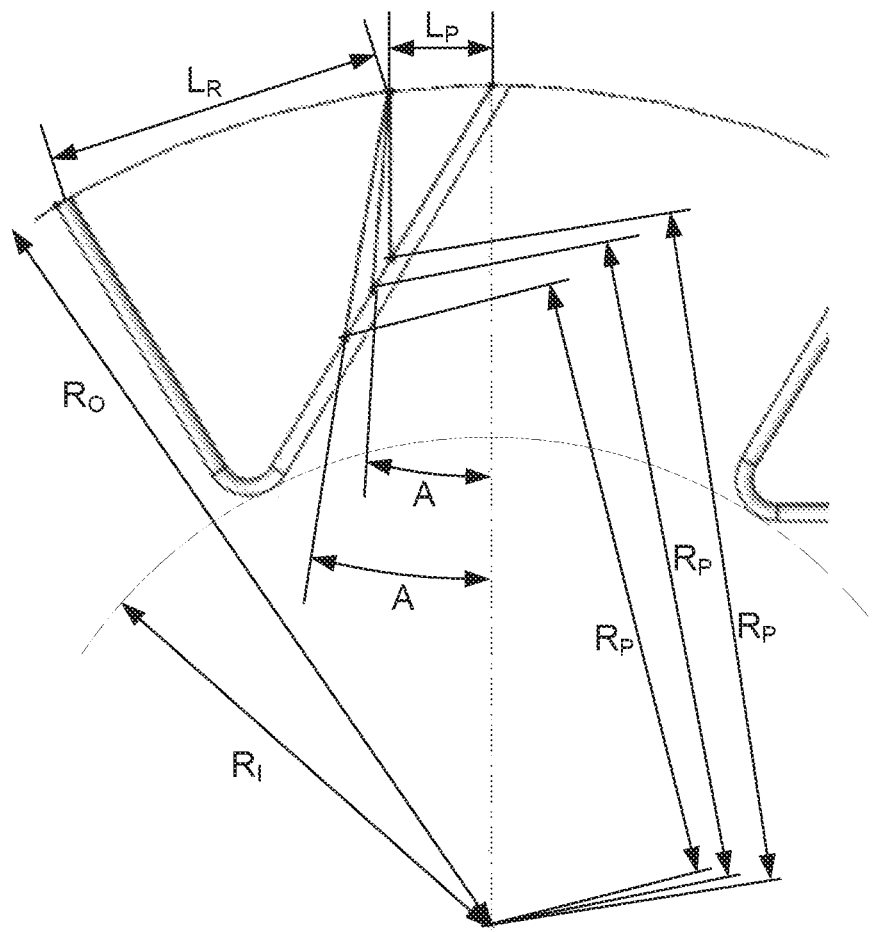
FIG. 19C is a schematic plan view illustrating bearing parameters.

An example of the configuration of the impeller to act as a hydrodynamic bearing is shown in FIGS. 19A to 19C.

In this example, the impeller includes a rotor 1920, having a number of vanes 1921 mounted thereon. In this example, six vanes are shown, although in practice any number above three, and typically below 10 could be used.

Each vane 1921 includes a ramp 1921.1 and a pad 1921.2. The ramp is angled so that as the impeller rotates in the direction of arrow 1900, some fluid is directed along the ramp, as shown by the arrow 1901, to flow between the impeller vanes and the end wall 1810.1, thereby creating the hydrodynamic bearing effect. The pad 1921.2 is created as a flat section parallel to the end wall 1810.1, which acts to provide resistance to flow and reduce leakage past the ramp 1921.1, thus amplifying the hydrodynamic bearing effect. The Ratio of the ramp length $L_R$ to the pad length $L_p$ should be between 0.1 to 0.3 and is typically 0.2.

There are seven main parameters that determine the optimal hydrodynamic bearing design as shown in FIG. 19C, which shows three different designs. These include inner radius of the impeller vane $R_I$, outer radius of pad $R_O$, inner radius of flat pad $R_P$, length of the flat pad $L_P$, the height of the ramp, the length of the ramp $L_R$, number of pads and surface speed of the medium.

In one example, the outer radius of the pad is dependent on the impeller diameters, and is fixed at 25 mm. The inner radius of the flat pad, overall length of the blade, surface speed and the number of pads are determined based on the lift generation required by the hydrodynamic bearing forces, while the inner radius of the vane influence the hemodynamics of the left impeller as it functions with the right impeller as a TAH pump.

The final design parameter is the length ratio of the flat pad to the ramp (10-30%) and the angle of the leading edge of the flat pad with respect to the radial center line to the center of the impeller (0-10 deg) which alters the inner radius of the flat pad from 18-20 mm.

In the example shown in FIG. 19C, the main parameter that varies between the designs is the angle of the leading edge of the flat pad, this in turn allows for more of the flat pad to be used as the hydrodynamic bearing, increasing the force generation, whilst not using the entire length of the impeller vane which would create additional shear but not increase force capacity at the inner radius due to a small length of ramp/pad area at that inner radius.

In one example, the flat pad has an inner radius of at least one of between 16 mm and 22 mm and between 18 mm and 20 mm, has a length of at least one of: between 1 mm and 5 mm; between 2 mm and 4 mm; and, about 3 mm; the ramp has a length of at least one of between 5 mm and 15 mm; between 8 mm and 12 mm; and, about 10 mm and has a height of at least one of: between 0.02 mm and 0.1 mm; between 0.04 mm and 0.08 mm; and, about 0.06 mm. The vanes typically have an inner radius that is at least one of between 10 mm and 20 mm; between 12 mm and 18 mm, between 14 mm and 16 mm; and, about 15 mm; and an outer radius that is at least one of between 20 mm and 30 mm; between 22 mm and 28 mm; between 24 mm and 26 mm; and, about 25 mm.

An example of typical design parameters is shown in Table 8 below:

TABLE 8

| | |
|---|---|
| Inner radius of Vane $R_I$ | 15 mm |
| Outer Radius of Vane $R_O$ | 25 mm |
| Inner Radius of Flat Pad $R_P$ | 18-20 mm |
| Length of Flat Pad $L_P$ | 3 mm |
| Length of Ramp $L_R$ | 10 mm |
| Height of Ramp | 0.06 mm |
| Number of Pads | 6 |
| Surface Speed | 4.83 m/s |

Hemodynamically, the 6-bladed impeller performed well for human application by creating a suitable left to right delta pressure ratio created by both pumping cavities.

Figure 19D:
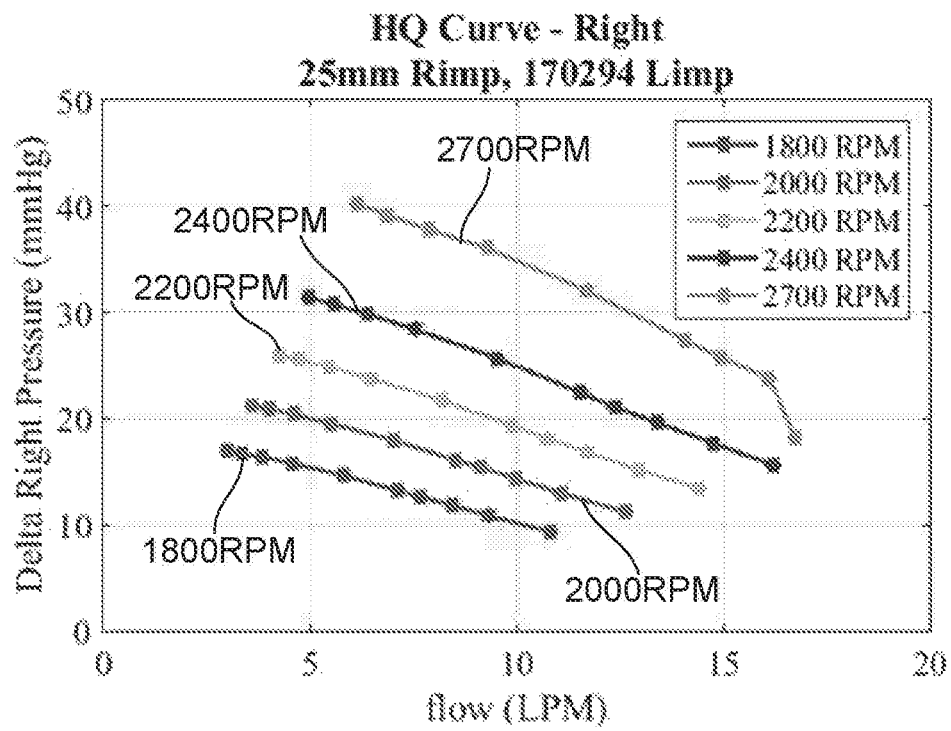
FIG. 19D is a graph illustrating an example of right pump performance.
Figure 19E:
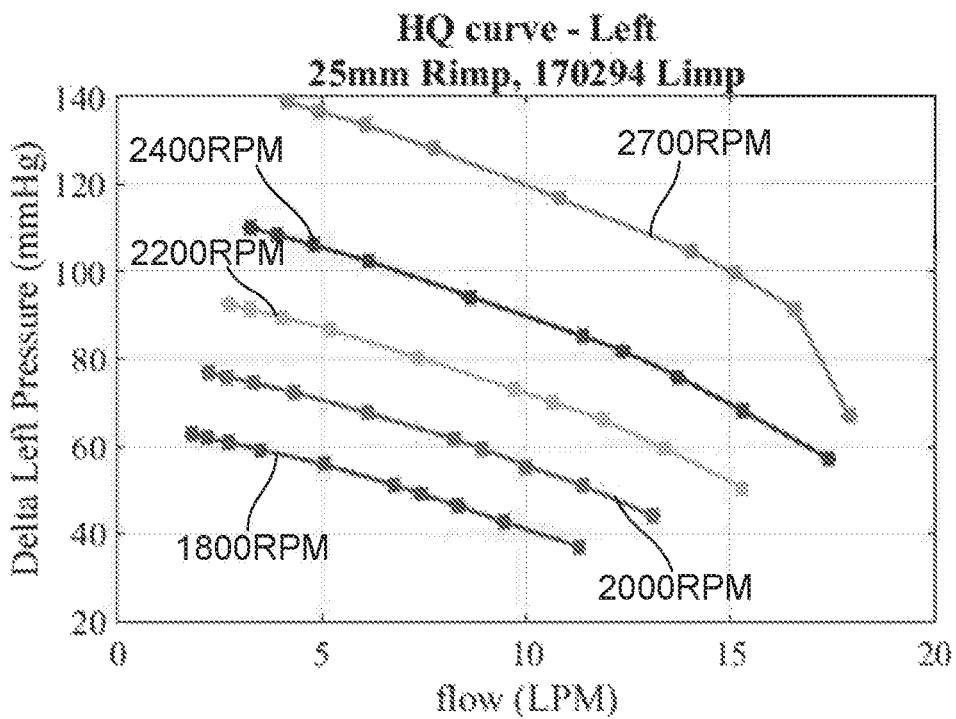
FIG. 19E is a graph illustrating an example of right pump performance.

Examples of the performance HQ curves in levitated mode at various speeds are shown in FIGS. 19D and 19E for the right and left pumps respectively.

These demonstrate desired flow rates for the range of operating speeds, and further show a desired Left to Right pressure matching ratio of 3.5:1

In any event, the bearing acts to create a force towards the cavity right end 1811.2, effectively urging the impeller 1820 away from the left end wall 1810.1 and counteracting the magnetic force generated by the drive magnets, to thereby maintain the impeller levitating within the cavity 1811.

Figure 20A:
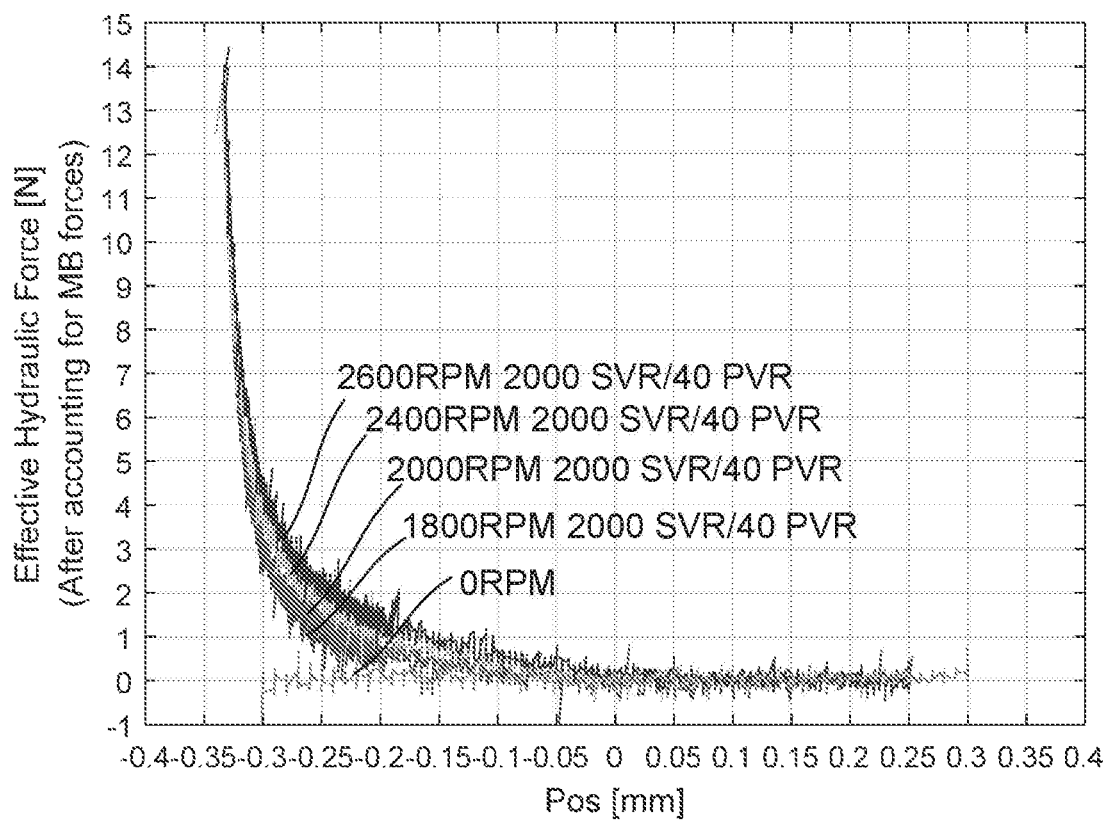
FIG. 20A is a graph illustrating examples of effective hydraulic axial impeller forces generated by a hydrodynamic bearing.

An example of the levitation force generated by the hydrodynamic bearing is shown in FIG. 20A. This highlights that as rotational speed of the impeller increases, the net hydraulic force generated by the bearing increases, with the impeller moving further away from the left end wall 1810.1 as shown.

In contrast, if the impeller moves to the right end 1811.2 of the cavity 1811, as the right impeller blades typically have a much smaller upper surface area, they do not provide a hydrodynamic bearing effect, and the impeller would contact the right end wall 1810.2 of the housing 1810, which can in turn lead to pump damage, and reduced effectiveness. Accordingly, it is desirable to ensure that should the magnetic bearing fail, it is possible in the event that the rotor moves to the right hand side of the cavity for the impeller 1820 to be moved to the left hand side of the cavity, thereby allowing the hydrodynamic bearing to operate.

Figure 20B:
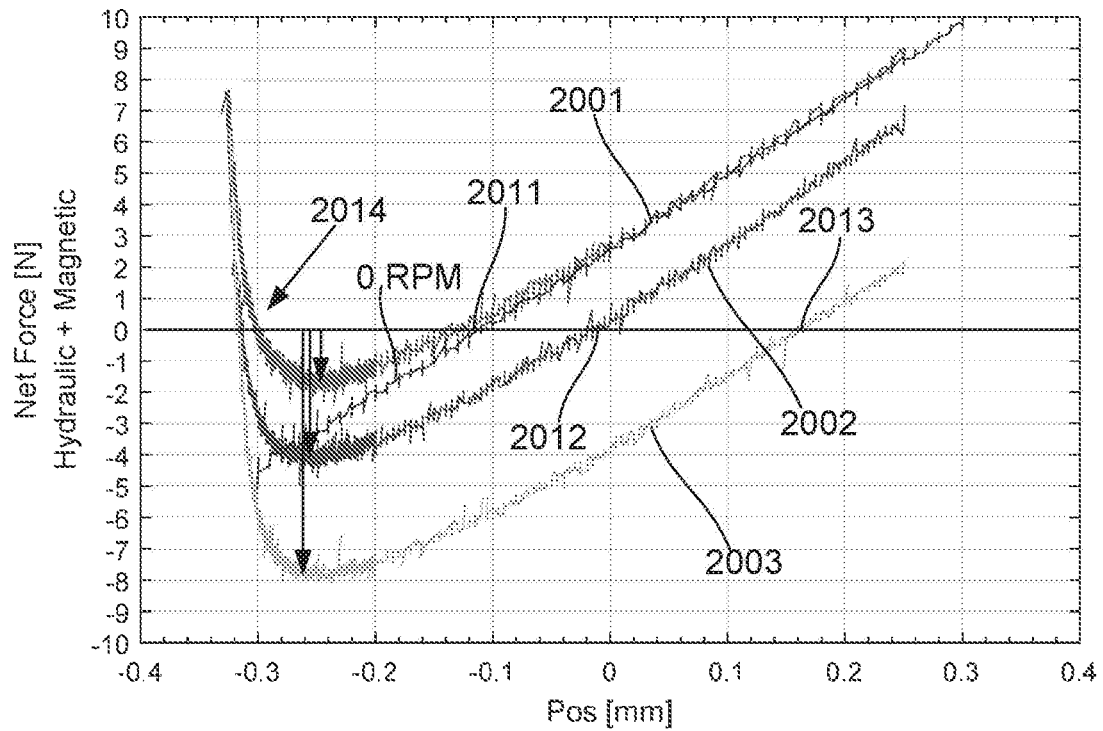
FIG. 20B is a graph illustrating examples of net hydraulic and magnetic axial impeller forces.

The combined effect of the hydraulic and magnetic forces is shown in FIG. 20B.

A balance point for the impeller will be found coincident with the zero net force line. The curves show the typical forces under conditions of constant rotational speed and SVR and PVR values, corresponding to the subject being stressed leading to systemic hypertension 2001, at rest 2002 and undergoing exercise 2003.

The net force is initially high and directed axially towards the bearing when the impeller is on the cavity left side 1811.1 (position<−0.3 mm), when the force generated by the hydrodynamic bearing dominates. As the impeller moves towards the centre of the cavity 1811 (position=±0.2 mm), the net forces become initially negative, representing magnetic attraction towards the drive 1830, before returning to a net force towards the bearing 1840 as the impeller 1820 approaches the magnetic bearing 1840 (position>0.2 mm).

Under normal pump operating conditions, the controller 150 operates the magnetic bearing 1840 to minimise the power required by the magnetic bearing 1840 to maintain the position the impeller 1820 within the cavity 1811. To achieve this, the controller 150 uses the bearing to position the impeller 1820 within the cavity 1811 at a point indicated by the intersection with the zero axis on the right hand part of the curve, as shown at 2011, 2012, 2013 for stress, rest and exercise respectively. In contrast, should the magnetic bearing fail, then it is desirable for the impeller will move to the left hand intersection with the zero axis, as shown generally at 2014, with the impeller being supported by the hydrodynamic bearing only.

In the event that the magnetic bearing fails, depending on where the impeller 1820 is positioned within the cavity 1811 and the current hemodynamic conditions, the impeller 1820 may move to the cavity left or right end 1811.1, 1811.2. For example, it can be seen that under exercise conditions, the impeller 1820 would normally be located towards the cavity right end 1811.2, and so this, coupled with greater fluid pressure in the cavity left end 1811.1, means the impeller is more likely to be attracted to the bearing 1840 in the event that the bearing fails 1840. In the event that the impeller 1820 moves to the cavity right end 1811.2, action needs to be taken to move the impeller 1820 to the cavity left end 1811.1 so that the hydrodynamic bearing functions correctly.

Even when the impeller 1820 moves to the cavity left end 1811.1, an axial force, for example arising through a physical shock to the housing 1810, can cause the impeller 1820 to move to the cavity right end 1811.2. The force required is shown by the arrows in FIG. 20B, and corresponds to an axial force of about 2, 4 or 8 Newtons for each of the stress, rest and exercise conditions shown.

Furthermore, in the event that the impeller moves all the way to the right hand side of the cavity, a force of 15 Newtons is required to move the impeller back to the left hand side of the cavity.

It will be appreciated based on this it can be desirable to generate an axial force towards the drive 1830, either to move the impeller 1820 to the cavity left end 1811.1 and/or to reduce the risk of external forces causing the impeller 1820 to be dislodged to the cavity right end 1811.2. In one example, this can be achieved through appropriate control of the drive 1830, in particular through appropriate configuration of the magnetic fields generated by the drive, and using these to generate an axial attractive or repulsive force. Examples of this will now be described with reference to FIGS. 21A to 21C.

For these examples, the drive includes a plurality of circumferentially spaced permanent drive magnets 2134 mounted on a soft iron rotor drive yoke 2135 within the impeller. The drive also includes a plurality of circumferentially spaced drive coils 2131 mounted proximate the left hand end of the cavity, with each coil 2131 being wound on a respective drive stator pole 2132.1 of a drive stator core 2132 and being substantially radially aligned with the drive magnets 2134.

Figure 21A:
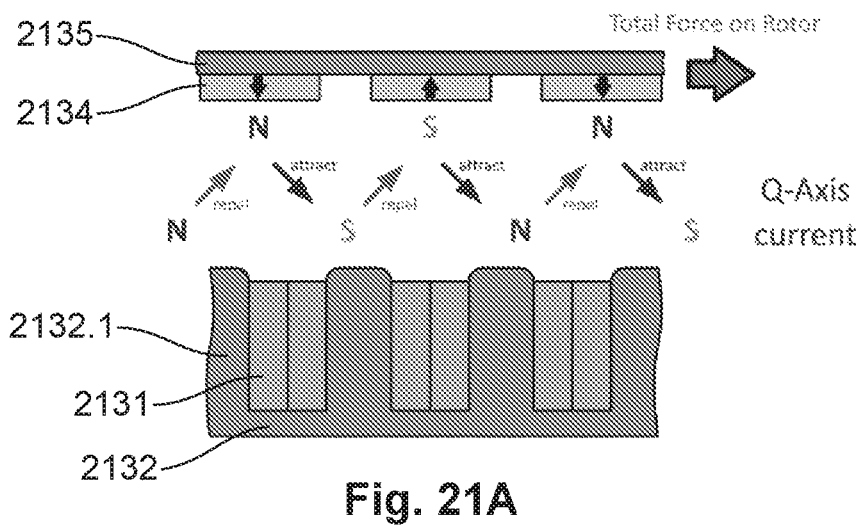
FIG. 21A is a schematic diagram illustrating an example of operation of the drive to generate a rotational impeller torque.
Figure 21B:
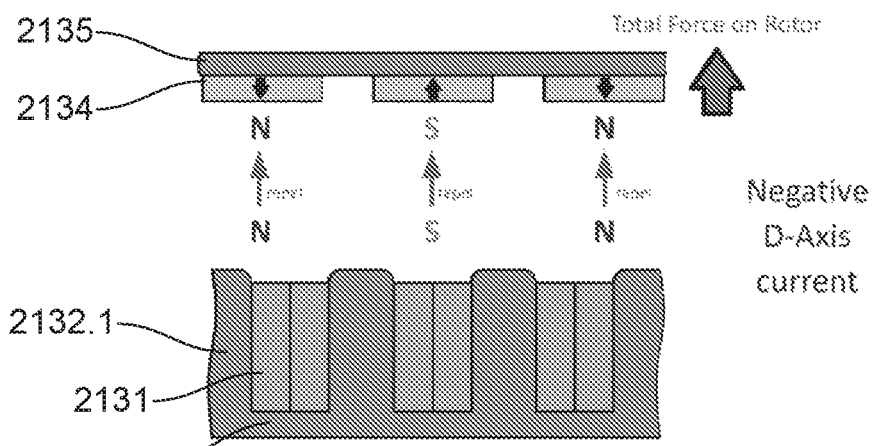
FIG. 21B is a schematic diagram illustrating an example of operation of the drive to generate a negative axial impeller force.
Figure 21C:
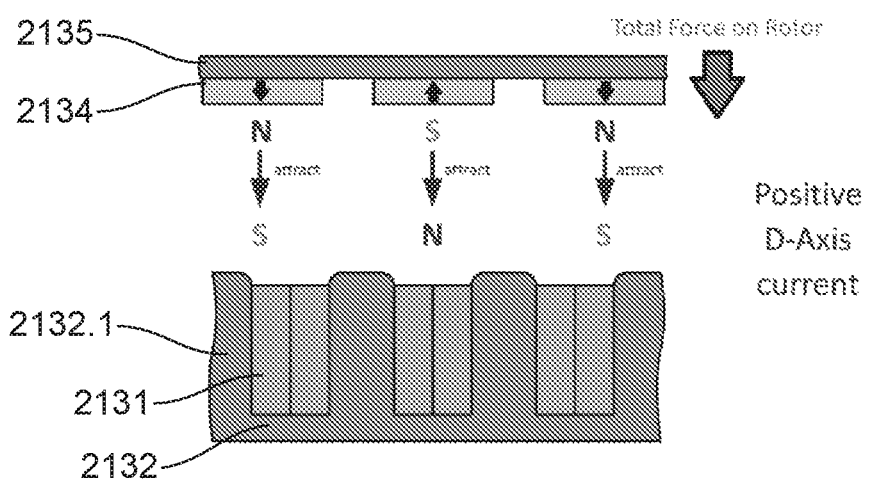
FIG. 21C is a schematic diagram illustrating an example of operation of the drive to generate a positive axial impeller force.

In the example of FIG. 21A, the coils 2131 are controlled so that adjacent coils generate opposing fields offset from the drive magnets, which thereby attract and repel the drive magnets 2134 at an angle, thereby generating a rotational torque. In contrast, in the examples of FIGS. 21B and 21C, the drive coils 2131 generate fields aligned with the drive magnets 2134, but having equal or opposite polarities to generate a repulsive or attractive force respectively.

For the remaining description an attractive force towards the drive is referred to as a positive axial force, whereas a repulsive force is referred to as a negative force. Furthermore, the terms rotational and axial currents are used to describe currents that when applied to the drive generate a rotational or axial force.

In any event, it will be appreciated from this that the controller, through suitable control of the drive signal generator 137 can control the drive 1830 and thereby generate a positive axial force towards the drive 1830. This can be used to allowing the impeller 1820 to be moved from the cavity right end 1811.2 to the cavity left end 1811.1, without requiring intervention by the magnetic bearing 1840, or to increase the axial force towards the drive 1830 and thereby reduce the likelihood of the impeller 1820 being displaced to the cavity right end 1811.2 under action of an external force.

Accordingly, the controller can control the drive to generate the axial attractive force to either move the impeller within the cavity and/or increase shock resistance when operating using a hydrodynamic bearing in the event that the magnetic bearing fails. To do this, the controller either detects failure of the magnetic bearing or movement of the impeller to a right side of the cavity when the magnetic bearing has failed and then controls the drive to generate the axial attractive force in response to the detection. The controller detects failure of the magnetic bearing or movement of the impeller based on at least one of a bearing indicator indicative of a current used by the magnetic bearing, a drive indicator indicative of a current used by the drive or sensor signals, such as position sensor signals.

An example of operation by the controller to activate the hydrodynamic bearing following a bearing failure will now be described with reference to FIGS. 22A to 22D.

In this example, at a time t<0 the pump is operating nominally, and the bearing 1840 is functioning using a relatively constant minimal current 2211, with the impeller 1820 positioned in the working region 1881, slightly towards the cavity left end 1811.1, as shown at 2221. The drive is operating at a constant rotational speed 2231, using a constant drive rotation current 2241.1 and zero axial current 2241.2.

At time t=0, a levitation fault occurs and the magnetic bearing fails, indicated by a momentary increase in bearing current 2212. A constant current 2213 is injected into the bearing 1840 in an attempt to cause the bearing to operate again, with this being deactivated after a predetermined time shown at 2214, in this case 0.3 seconds, when the magnetic bearing is unresponsive.

As shown in this example, when the bearing fails, the impeller 1820 moves to the cavity right end 1811.2 at 2222, with a dip 2232 in impeller rotational speed occurring due to load changes in the drive 1830. In particular, increased friction caused by contact between the impeller 1820 and the right end wall 1810.2 results in the impeller momentarily slowing, until the rotational current is increased 2242.1 to counteract friction between the impeller 1820 and right end wall 1810.2. It will be appreciated that this allows the controller 150 to ascertain that touchdown on the right hand side of the impeller cavity has occurred.

As a result, the motor is controlled to generate a large positive axial current 2242.2, which causes the impeller 1820 to lift from the right end wall 1810.2 and move towards the left end wall 1810.1. As frictional loads lift, this causes a corresponding jump in rotational speed 2233, allowing the drive rotational current to return to its original value 2243.1 in order to maintain the impeller speed rotational speed. From this point on, the impeller is no longer magnetically suspended, but rather is suspended based on the operation of the hydrodynamic bearing, as shown by the impeller position 2223.

Accordingly, this describes the operation of the device in order to displace the impeller 1820 from the cavity right end 1811.2 to the cavity left end 1811.1.

Figure 23:
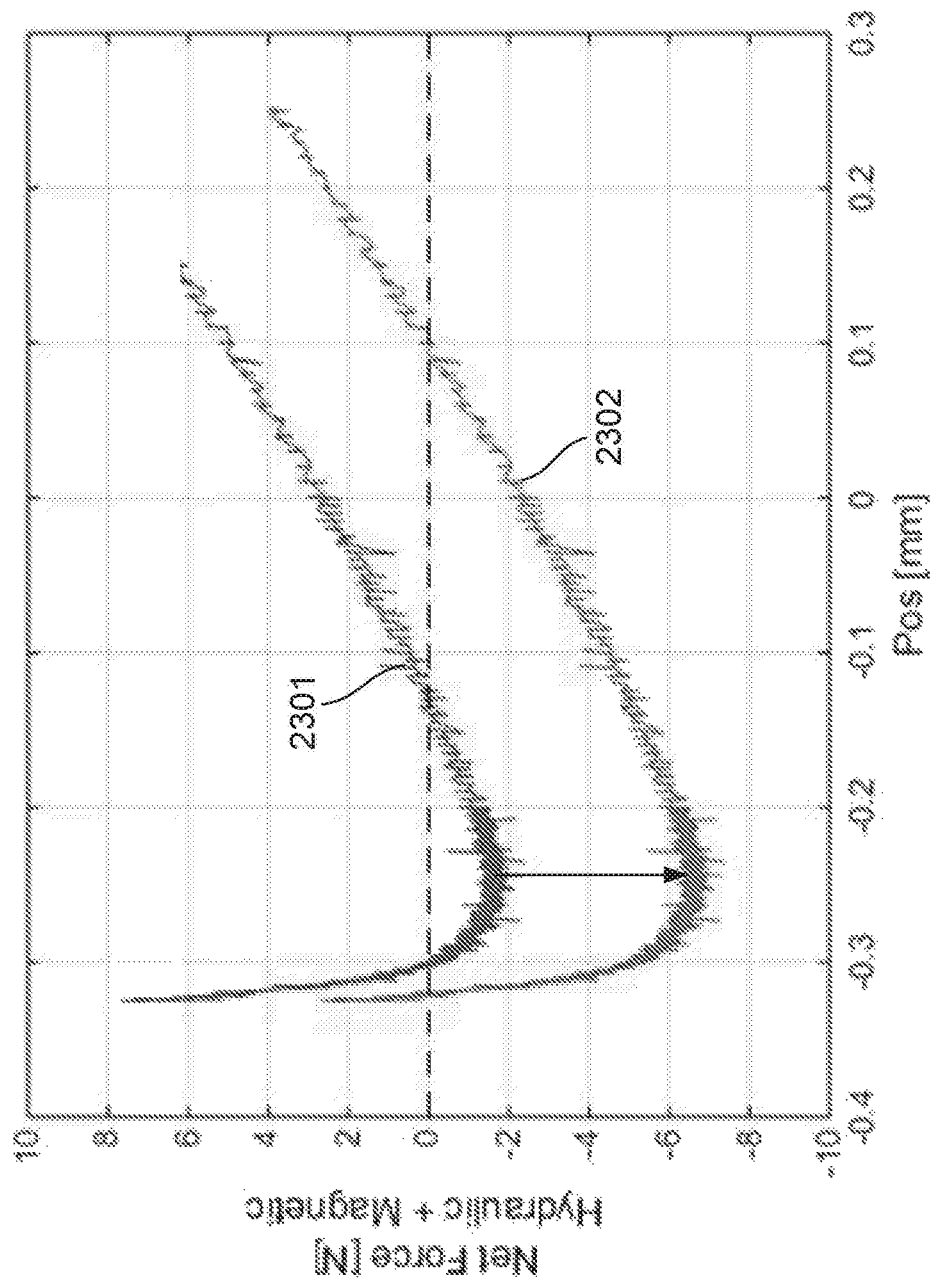
FIG. 23 is a graph illustrating an example of the effect of a positive axial force on the net axial impeller forces.

Once in the cavity left end 1811.1, a drive axial force can be used to help prevent the impeller moving back to the cavity right end 1811.2 and an example of this is shown in FIG. 23, which highlights the net force curve 2301 for a subject stressed. Applying a positive axial current via the drive shifts the curve downward 2302, so that the net force required to dislodge the impeller from the hydrodynamic bearing onto the right hand side of the casing increases from 2 newtons to 7 newtons, as shown by the arrow. It will be appreciated that further increases in the axial drive force could be used to increase this further.

Figure 24A:
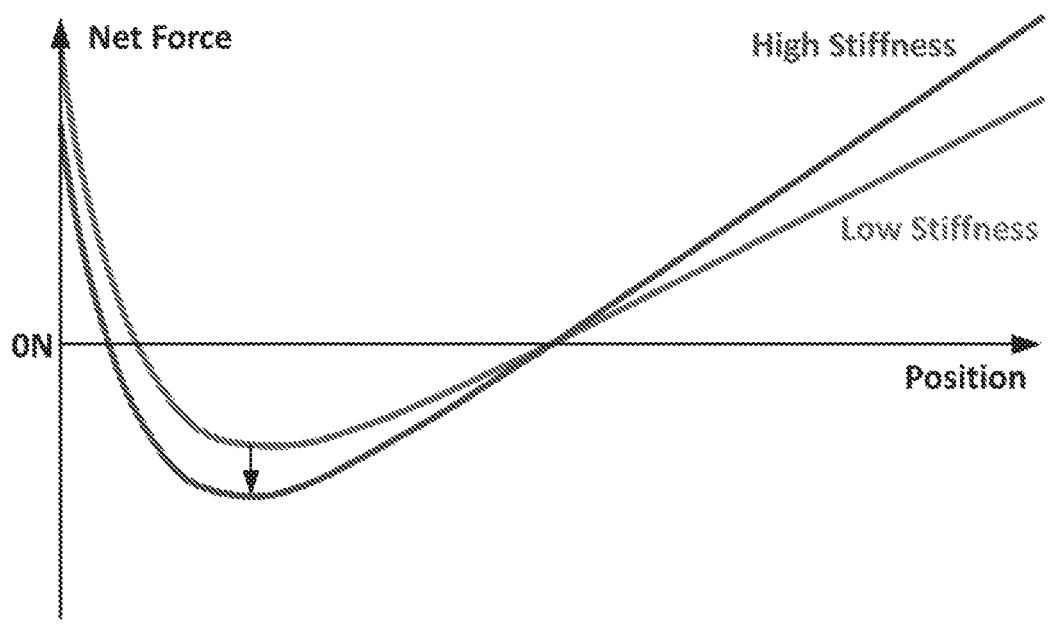
FIG. 24A is a graph illustrating an example of the impact of axial stiffness on the net axial impeller forces.

FIG. 24A shows the impact of bearing stiffness, highlighting that for a higher bearing stiffness, the force required in order to move the impeller from the left to the right hand side of the casing is increased, as shown by the arrow, thereby suggesting that a higher inherent axial stiffness is beneficial. This will also help increase radial stiffness, thereby reducing the chance of the impeller contacting the housing as a result of external applied forces.

Figure 24B:
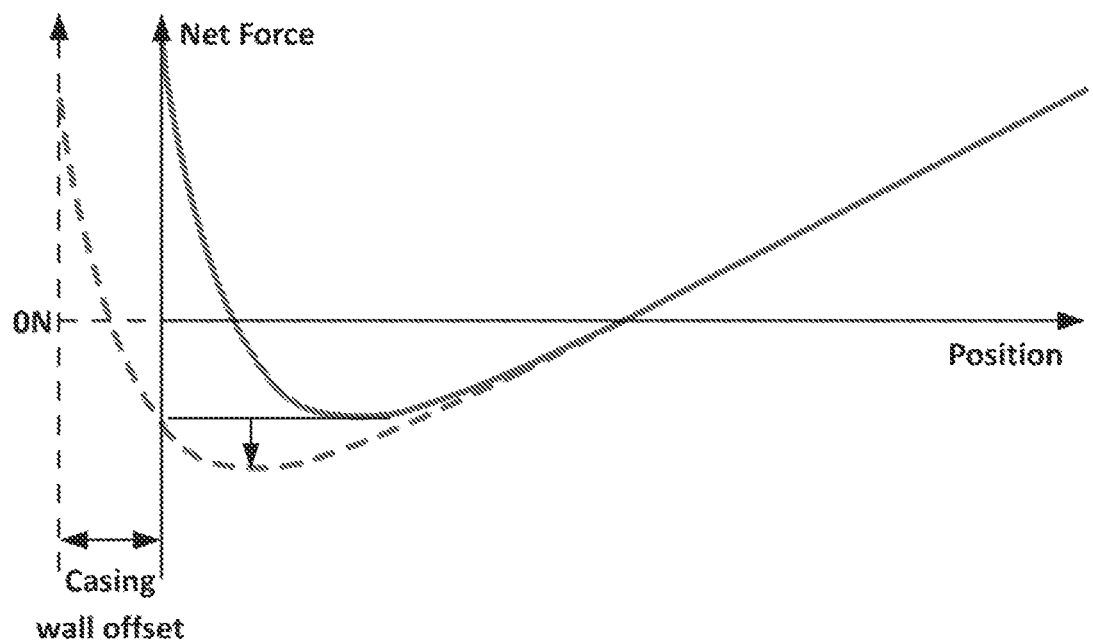
FIG. 24B is a graph illustrating an example of changes in net axial impeller force for a casing offset.

A further option that can be implemented is to reduce an offset of the left end wall 1810.1 from the drive 1830, which can further help further increase the force required in order to dislodge the impeller 1820, as shown by the arrow in FIG. 24B.

It will be appreciated from the above that the alteration of the drive current can be used to adjust the bearing stiffness. Similarly, the bearing current can also be used, which is particularly useful in controlling the radial stiffness.

The radial movement or vibration of the rotor in response to radial excitation force, such a rotor imbalance, varies as a function of the radial stiffness, radial damping, the excitation frequency and the rotor mass. The amplitude of the vibration response peaks at the resonant frequency which can cause the rotor to exhibit large vibrational amplitudes in response to excitation forces and in some cases, where insufficient damping and stiffness is present, can cause the rotor to touchdown or become unstable.

In some scenarios, operating at or around the resonant frequencies is undesirable, and should be avoided. If operation of the rotor speed at resonant frequencies is required and the resonant frequency cannot be modified through changes to the stiffness, damping or rotor mass, it is possible to temporarily alter the system stiffness to move the resonant frequency by modifying the stiffness with a bias current.

To reduce the vibration of the rotor when operating close to the resonant frequency the radial stiffness can be temporarily increased, thereby increasing the resonant frequency.

Figure 25A:
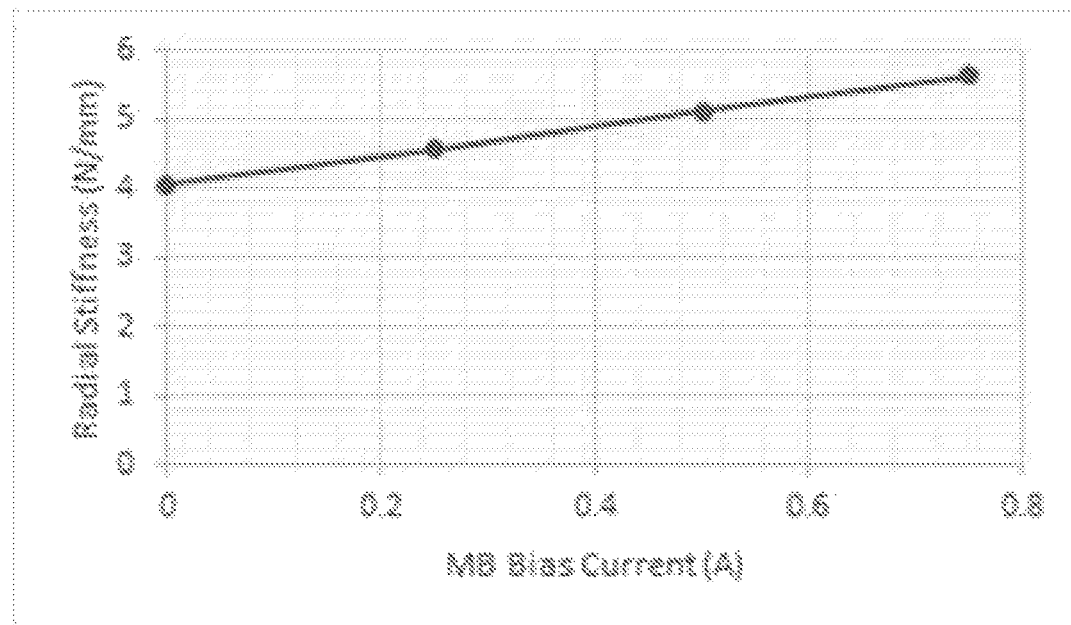
FIG. 25A is a graph illustrating an example of the impact of bearing current on radial stiffness.
Figure 25B:
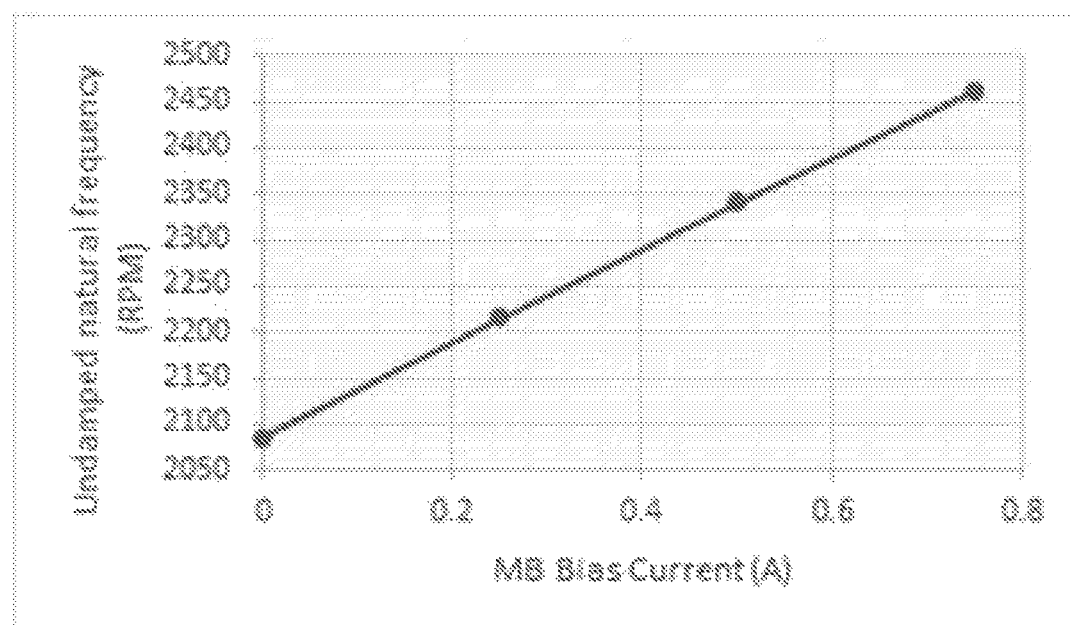
FIG. 25B is a graph illustrating an example of the impact of bearing current on resonant frequency.
Figure 25C:
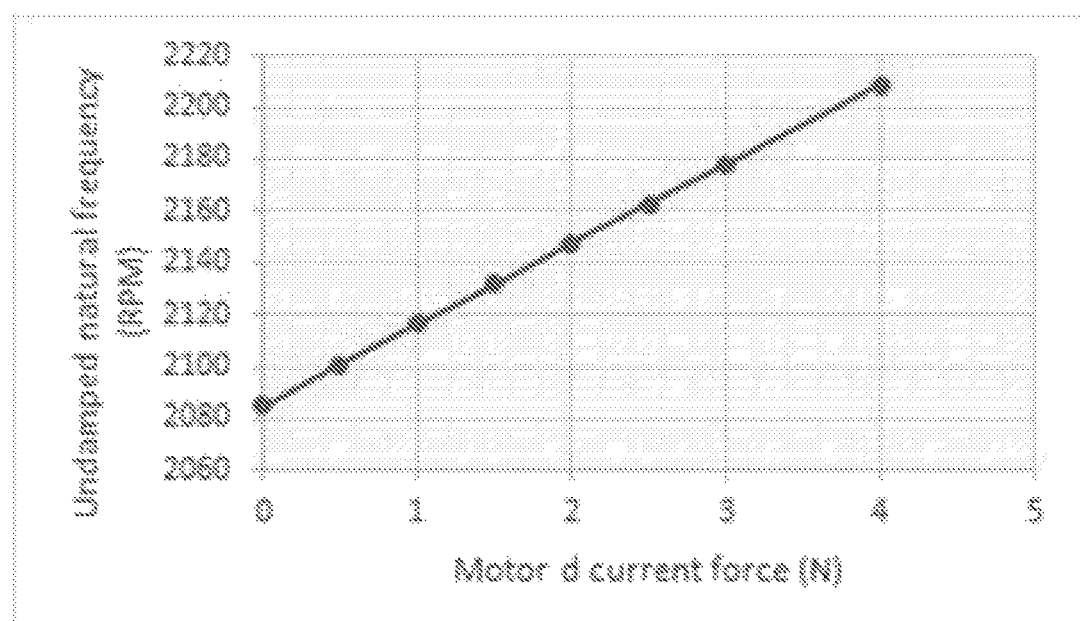
FIG. 25C is a graph illustrating an example of the impact of drive current on resonant frequency.

One method of achieving this is to add additional current to the magnetic bearing coils to increase its force and stiffness whilst maintain the rotor position. This increase of stiffness will increase the resonant frequency of the system higher than its typical value and allow for operation with reduced vibration at the original resonant frequency, and an example of the increase of radial stiffness from the magnetic bearing when the rotor is maintained in a constant position and the amount of magnetic bearing bias current is increased is shown in FIG. 25A. The impact of this on the undamped radial resonant frequency, when the rotor is maintained in a constant position and the amount of magnetic bearing bias current is increased, is shown in FIG. 25B. A similar change for an increase in drive axial current is shown in FIG. 25C.

In addition to the increase of stiffness the bias current will provide an attractive force which can be counteracted by increasing the attractive force of the motor via direct current. Another method of temporarily increasing the stiffness can also be achieved by moving the rotor position towards the magnetic bearings, whilst maintaining the normal amount of bias current.

This can be achieved in the above described system by utilizing the controller. When the motor controller identifies that it is operating close to a known resonant frequency it can add an additional motor axial attractive force by increasing the motor direct current causing the axial levitation controller to move the rotor towards the magnetic bearings, thereby increasing the radial stiffness.

Whilst the above example has focussed on the use of the hydrodynamic bearing as a failure mode for a magnetically levitated impeller. It will be appreciated that this is not essential and alternatively, the hydrodynamic bearing could be used as a replacement for the magnetic bearing.

In the example, the heart pump could include a housing defining a cavity including at least one inlet aligned with an axis of the cavity and at least one outlet provided in a circumferential outer wall of the cavity. An impeller can be provided within the cavity, the impeller including a rotor and vanes mounted on the rotor for urging fluid from the inlet radially outwardly to the outlet. A drive is then provided for rotating the impeller in the cavity, the drive including: a plurality of circumferentially spaced permanent drive magnets mounted within and proximate a first face of the rotor and, a plurality of circumferentially spaced drive coils mounted within the housing proximate a first end of the cavity. In this example, vanes of the impeller and the first end of the housing cooperate to define a hydrodynamic bearing, thereby levitating the impeller within the cavity.

An example of a number of coil winding configurations will now be described with reference to FIGS. 26A to 26D.

Figure 26A:
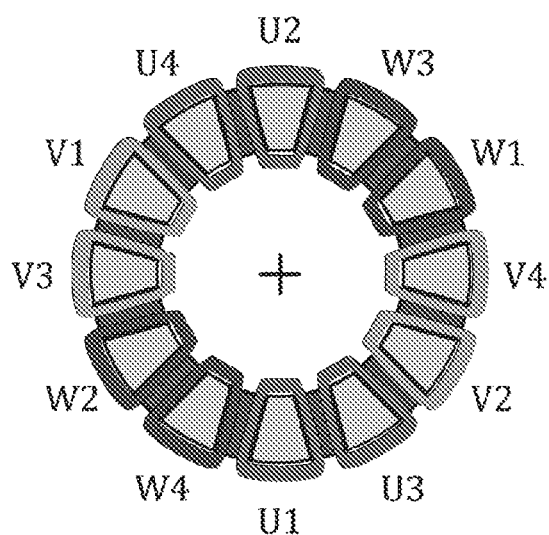
FIG. 26A is a schematic diagram of a first example of a three phase drive coil configuration.
Figure 26B:
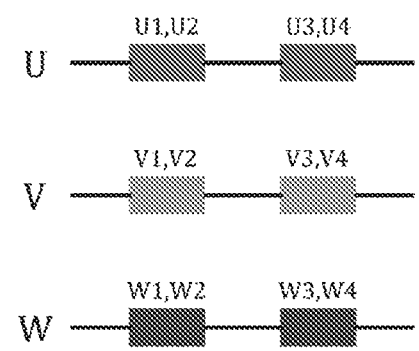
FIG. 26B is a schematic diagram of an example of the drive coil connections for the drive coil configuration of FIG. 26A.

In the example of FIG. 26A, the drive includes twelve separate coils, which are operated in order to provide a three phase drive. In particular, opposing pairs of coils U1, U2; U3, U4; V1, V2; V3, V4; and W1, W2; W3, W4 being controlled sequentially in order to provide a single three phase drive configuration. In practice this is achieved by applying drive signals for each phase to respective pairs of coils in series, as shown in FIG. 26B.

Figure 26C:
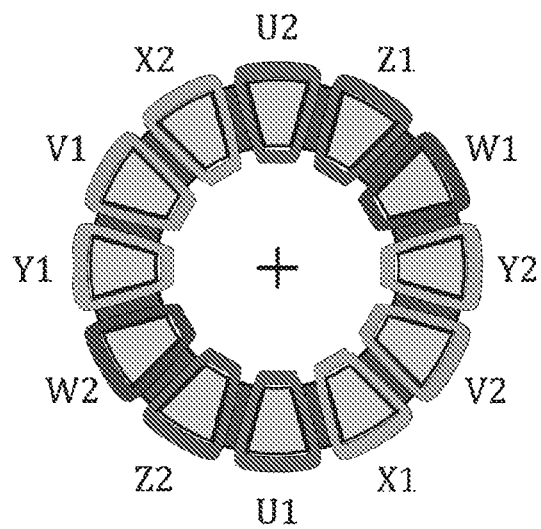
FIG. 26C is a schematic diagram of a second example of a three phase drive coil configuration.
Figure 26D:
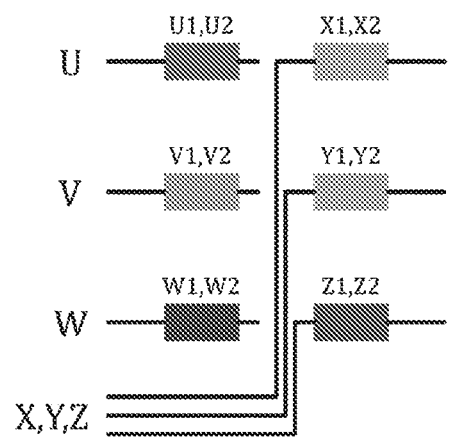
FIG. 26D is a schematic diagram of an example of the coil connections for the coil configuration of FIG. 26C.

In contrast, in the arrangement of FIG. 26C, the same physical twelve coil arrangement is utilised, with opposing pairs of coils being controlled in order to provide dual three phase arrangements. Specifically, coils U1, U2; V1, V2; W1, W2 provide a first three phase drive, whilst coils X1, X2; Y1, Y2; Z1, Z2 form a second three phase drive. The use of a dual drive configuration shown in FIGS. 26C and 26D has a number of benefits, including providing fault redundancy, for example in the event of one of the drives failing.

Figure 27A:
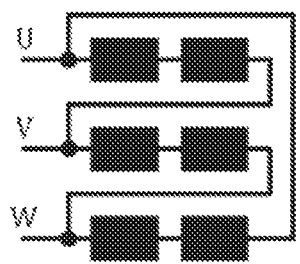
FIG. 27A is a schematic diagram of an example of drive coil connections for a single three phase delta configuration.
Figure 27B:
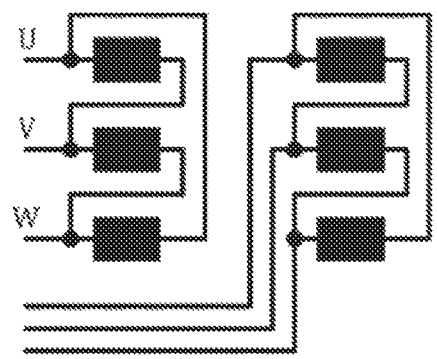
FIG. 27B is a schematic diagram of an example of drive coil connections for a dual three phase delta configuration.
Figure 27C:
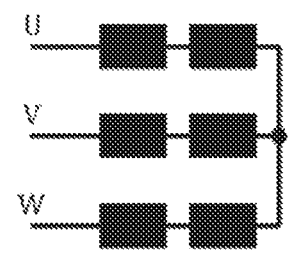
FIG. 27C is a schematic diagram of an example of drive coil connections for a single three phase star configuration.
Figure 27D:
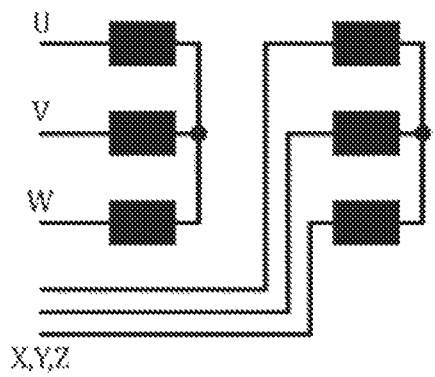
FIG. 27D is a schematic diagram of an example of drive coil connections for a dual three phase star configuration.

As further shown in FIGS. 27A to 27D, it is also possible to utilise different winding configurations known as delta and star configurations. In this regard, FIG. 27A shows a single three phase drive in a delta configuration, FIG. 27B shows a dual three phase drive in a delta configuration, FIG. 27C shows a single three phase drive in a start configuration, whilst FIG. 27D shows a dual three phase drive in a star configuration. The use of star and delta configurations can result in different operational parameters, as will now be described.

Figure 28A:
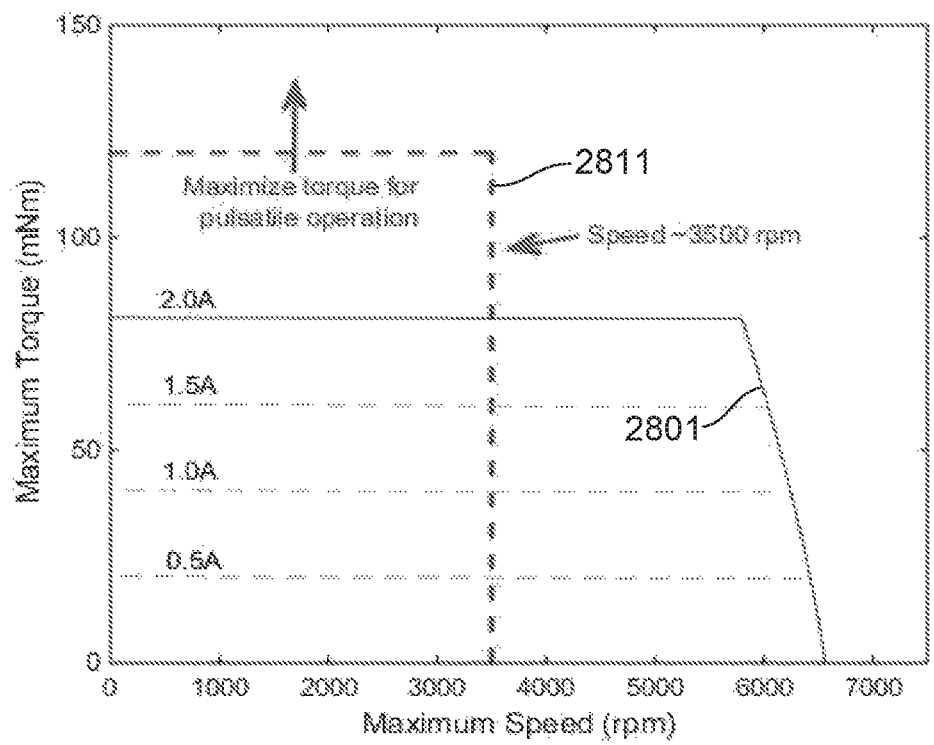
FIG. 28A is a graph illustrating an example of a drive torque and speed achievable using a delta drive coil winding.

In this regard, FIG. 28A shows a curve 2801 illustrating the speed versus maximum torque that can be obtained using a single three phase delta winding configuration, in comparison to a desired range curve 2811. In this regard, the desired operating range for a heart pump typically only requires a maximum speed of about 3500 RPM, whereas the delta winding allows a speed of about 6500 RPM to be achieved. Conversely, a maximum torque of approximately 120 mNm or higher is preferred to achieve pulsatile operation, whilst delta winding can only achieve approximately 80 mNm at a 2 amp current. Whilst the torque achievable could be increased by increasing the current, this is generally undesirable as it leads to increased energy usage and heating in the driveline cable.

Figure 28B:
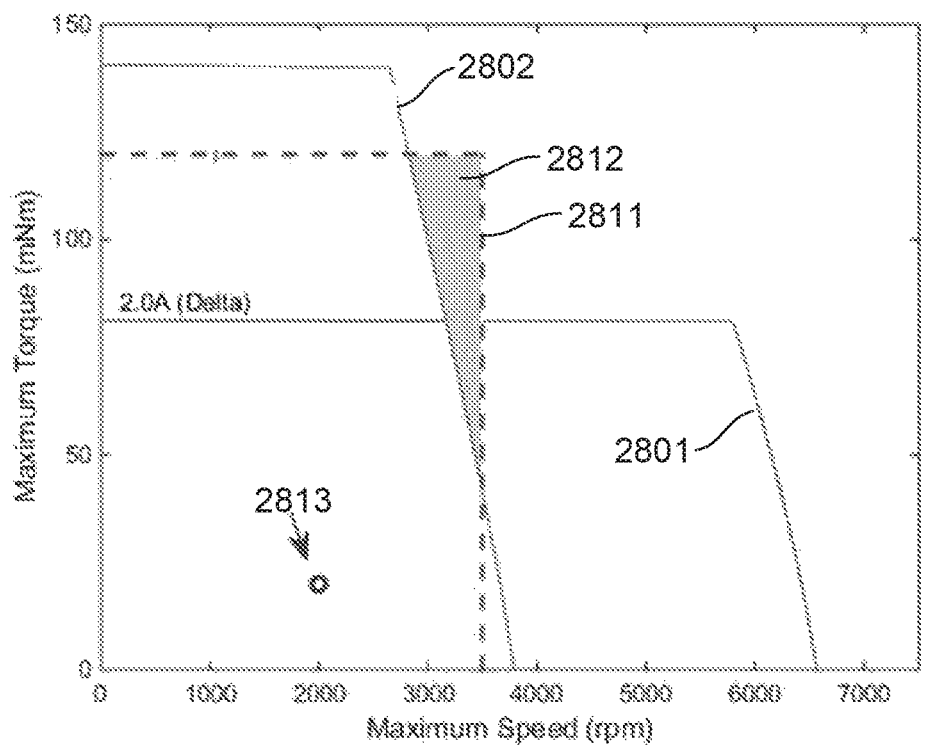
FIG. 28B is a graph illustrating an example of a comparison of a drive torque and speed using delta and star drive coil configurations.

As shown in FIG. 28B, a star connection of the same coils increases the available torque to approximately 140 mNm, whilst reducing the maximum speed to 4000 RPM. Whilst there is a shortfall in maximum speed at high torques, as shown by the grey triangle in FIG. 28B, generally this is not problematic, as it is infrequent that high torques are required at high speeds. Furthermore, the typical standard operating conditions, shown at 2813 can be achieved using a current of 0.4 A for a star configuration, as opposed to 0.7 A for the delta configuration, thereby making the star configuration more energy efficient.

Figure 29:
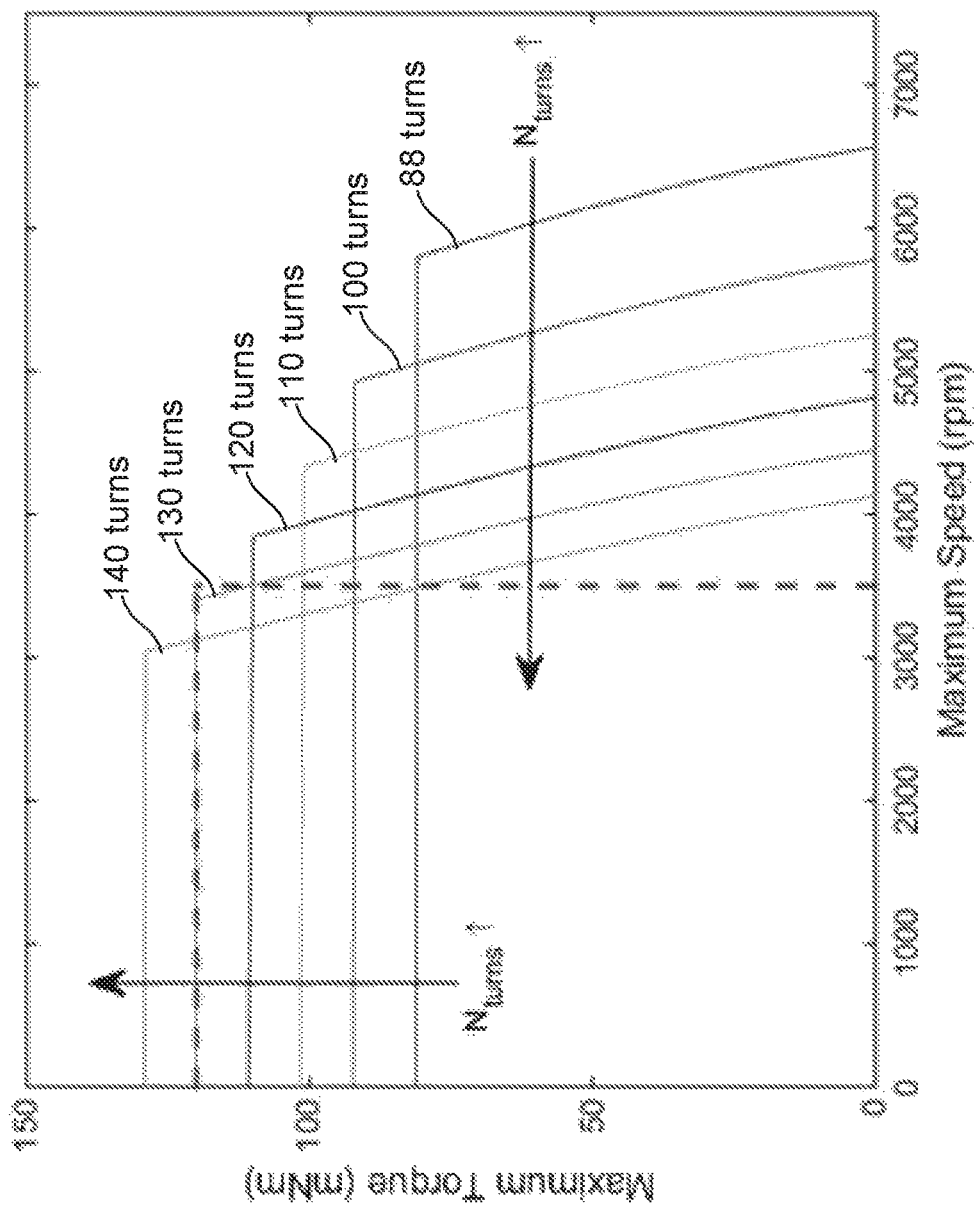
FIG. 29 is a graph illustrating an example of the impact of the number of drive coil winding turns on the drive torque and speed.
Figure 30A:
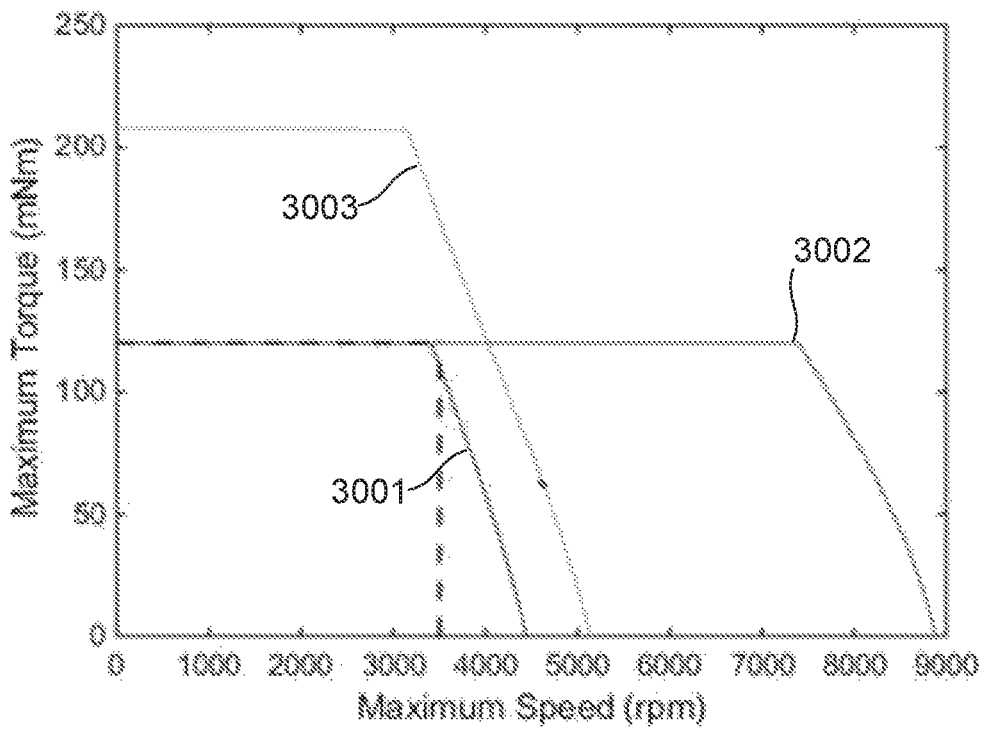
FIG. 30A is a graph illustrating examples of drive speed and torque for different coil configurations; and, FIG. 30B is a graph illustrating examples of drive speed and torque for healthy and faulty dual three phase star drive coil configurations.
Figure 30B:
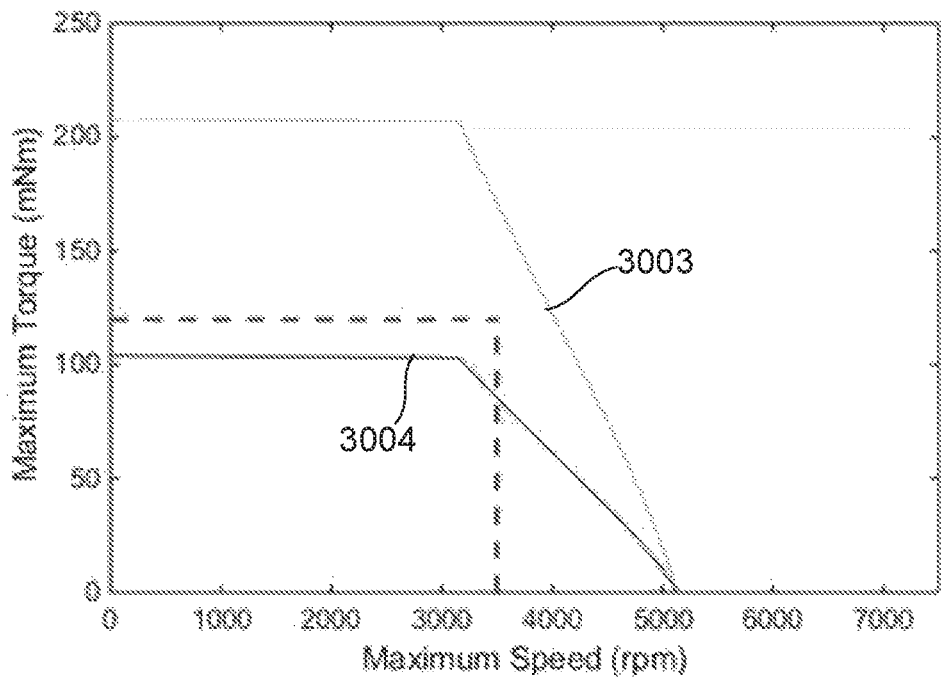

FIG. 29 shows that increasing the number of turns even in a delta configuration can improve the torque speed characteristics of the drive, whilst FIG. 30A highlights that a single three phase delta winding 3001 can generate less speed than a dual phase delta winding 3002, for the same maximum supply voltage and current, and a similar number of turns, in this case 130. It will be noted that this assumes a constant cross-sectional area of the coil, meaning that as more turns are provided, the wire diameter reduces to maintain overall coil area. Further improvements are again demonstrated with a dual star winding 3003, whilst even if one of the drives fail in this configuration, the drive can effectively operate as a single three phase star configuration with half of the coils inactive, whilst is still being able to perform adequately over substantially the entire desired range, as shown at 3004.

Based on this the preferred coil windings are single three phase delta windings, or dual three phase star windings, both of which can achieved desired speed and torque characteristics. The three phase delta windings provide a potentially higher fault tolerance (compared to star windings) in case of internal winding fault, whilst providing a simple system winding scheme. However, the dual phase star winding can provide increased fault tolerance due to redundant stator winding, can be configured to operate using lower drive currents, allow for a higher maximum torque under the same maximum supply voltage and phase current limits, and avoiding circulating currents, albeit with increased complexity.

It will further be appreciated that the increased torque capacity of a dual three phase winding is accompanied by a higher force generated per drive axial current. For example, the generation of an attractive force of 15N can be generated with a maximum phase current of approximately 3.8 A in a dual three-phase star configuration, while a single three phase delta configuration with a comparable maximum drive speed would require a maximum phase current of approximately 6.6 A. Reducing the current requirement in this manner is important in this particular application where supply voltages are typically limited to less than 24V and phase currents must be minimized due to driveline conductor and feedthrough pin sizing requirements. In circumstances where high levels of instantaneous DC current are required to create a large attractive force on the rotor, the limited voltage supply of the system can be a restriction. Increasing the height of the motor, whilst maintaining the same turn number by using a larger diameter wire, will effectively reduce the resistance of the coils, allowing more current and a higher force to be produced for the short period it is required, additionally increasing the height of the motor will also improve the overall efficiency of the motor.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers. As used herein and unless otherwise stated, the term "approximately" means ±20%.

Persons skilled in the art will appreciate that numerous variations and modifications will become apparent. All such variations and modifications which become apparent to persons skilled in the art, should be considered to fall within the spirit and scope that the invention broadly appearing before described.

What is claimed is:

1. A heart pump including:
 a) a housing defining a cavity including:
  i) at least one inlet aligned with an axis of the cavity; and,
  ii) at least one outlet provided in a circumferential outer wall of the cavity;
 b) an impeller provided within the cavity, the impeller including a rotor and vanes mounted on the rotor for urging fluid from the inlet radially outwardly to the outlet;
 c) a drive for rotating the impeller in the cavity, the drive including:
  i) a plurality of circumferentially spaced permanent drive magnets mounted within and proximate a first face of the rotor; and,
  ii) a plurality of circumferentially spaced drive coils mounted within the housing proximate a first end of the cavity, each coil being wound on a respective drive stator pole of a drive stator and being substantially radially aligned with the drive magnets, the drive coils being configured to generate a drive magnetic field that cooperates with the drive magnets to thereby rotate the impeller; and,
 d) a magnetic bearing including:
  i) first and second annular magnetic bearing members mounted within and proximate a second face of the rotor, the first magnetic bearing member being provided radially outwardly of the second magnetic bearing member;
  ii) a number of circumferentially spaced substantially U-shaped bearing stators mounted in the housing proximate a second end of the cavity, each U-shaped bearing stator having first and second bearing stator legs that interact with the first and second magnetic bearing members respectively; and,
  iii) at least one bearing coil on each bearing stator that generates a magnetic field that cooperates with the magnetic bearing members to thereby at least one of:
   (1) control an axial position of the impeller; and, (2) at least partially restrain radial movement of the impeller.

2. A heart pump according to claim 1, wherein at least one of:
  a) the first and second bearing stator legs are substantially magnetically aligned with the first and second magnetic bearing members respectively;
  b) the first and second bearing stator legs are substantially radially aligned with the first and second magnetic bearing members respectively;
  c) the first and second bearing stator cooperate with the first and second magnetic bearing members respectively so that a radial force from an individual bearing is about between 0 N-2N when the bearing stator legs are substantially aligned with the magnetic bearing members; and
  d) at least one of the first and second bearing stator legs are radially offset from a respective one of first and second magnetic bearing members by a distance that is at least one of:
    i) less than 1 mm;
    ii) less than 0.5 mm; and,
    iii) less than 0.2 mm.

3. A heart pump according to claim 1, wherein at least one of:
  a) the drive stator includes a soft magnetic composite core including a plurality of drive stator poles extending in an axial direction from an annular drive stator yoke;
  b) the drive stator yoke has a thickness of at least one of:
    i) between 1 mm and 2.5 mm;
    ii) about 1.75 mm;
  c) the drive stator poles are at least one of:
    i) wedge shaped;
    ii) triangular; and,
    iii) trapezoidal;
  d) adjacent drive stator poles are separated by a slot having at least one of:
    i) a width of at least one of:
      (1) between 4 mm and 7.4 mm; and,
      (2) about 6 mm; and,
    ii) a depth of at least one of:
      (1) between 4 mm and 14 mm; and,
      (2) about 11.25 mm; and,
  e) the drive stator has at least one of:
    i) an inner radius of at least one of:
      (1) between 14 mm and 18 mm; and,
      (2) about 16 mm; and,
    ii) an outer radius of at least one of:
      (1) between 22 mm and 25 mm; and,
      (2) about 24.5 mm.

4. A heart pump according to claim 1, wherein at least one of:
  a) each drive magnet at least one of:
    i) transects an angle at least one of:
      (1) between 15° and 36°; and,
      (2) about 25°; and,
    ii) has a thickness of at least one of:
      (1) between 0.8 mm and 3 mm; and,
      (2) about 2.6 mm;
  b) each drive magnet is mounted on an annular rotor drive yoke;
  c) the heart pump includes a common yoke that forms the rotor drive yoke and a rotor bearing yoke; and,
  d) the rotor drive yoke has a thickness of at least one of:
    i) between 1 mm and 5 mm;
    ii) between 1.5 mm and 2.5 mm; and,
    iii) about 1.9 mm.

5. A heart pump according to claim 1, wherein:
  a) the number of drive magnets is at least one of:
    i) 8;
    ii) 10;
    iii) 14; and,
    iv) 16; and,
  b) the number of stator poles is at least one of:
    i) 12;
    ii) 15; and,
    iii) 18.

6. A heart pump according to claim 1, wherein at least one of:
  a) the respective drive stator poles of the drive stator include 12 drive stator poles configured as at least one of:
    i) one three-phase motor; and,
    ii) two three-phase motors; and,
  b) the plurality of circumferentially spaced drive coils includes drive coils connected in at least one of a delta configuration and a star configuration.

7. A heart pump according to claim 1, wherein the drive and rotor are arranged such that, at least one of:
  a) a spacing between the first face of the rotor and the first end of the cavity is at least one of:
    i) between 2 mm and 5 mm in use;
    ii) between 2 mm and 3 mm in use; and,
    iii) approximately 2.3 mm in use;
  b) a spacing between a drive stator pole face and drive magnet face is at least one of:
    i) between 2.5 mm and 6 mm in use;
    ii) between 2.5 mm and 4 mm in use; and,
    iii) approximately 3.2 mm in use;
  c) a spacing between a drive stator yoke and drive magnet yoke is at least one of:
    i) between 7 mm and 25 mm in use;
    ii) between 8 mm and 20 mm in use; and,
    iii) approximately 17 mm in use; and,
  d) a spacing between a drive stator pole face and drive magnet yoke is at least one of:
    i) between 4 mm and 8 mm in use;
    ii) between 4.5 mm and 7 mm in use; and,
    iii) approximately 5.8 mm in use.

8. A heart pump according to claim 1, wherein a spacing between the first face of the rotor and the first end of the cavity is at least one of:
  a) at least 2.3 mm in use; and,
  b) sufficient to accommodate axial movement of the impeller in use.

9. A heart pump according to claim 1, wherein the vanes are mounted on the first face of the rotor between the first face of the rotor and the first end of the cavity and wherein the vanes have a height of at least one of:
  a) between 1.5 mm and 5 mm;
  b) between 1.5 mm and 2.5 mm;
  c) between 1.8 mm and 2.2 mm; and,
  d) about 2 mm.

10. A heart pump according to claim 1, wherein at least one of:
  a) each of the bearing stator legs has at least one of:
  b) a width that is at least one of:
    i) between 2 mm and 4 mm;
    ii) about 3.6 mm for the first bearing stator leg; and,
    iii) about 2.9 mm for the second bearing stator leg; and,
  c) a length of at least one of:
    i) between 5 mm and 35 mm; and,
    ii) about 14.8 mm;

d) the at least one bearing coil is wound on the first bearing stator leg; and,
e) the at least one bearing stator leg at least one of:
  i) is narrower than a corresponding magnetic bearing member at least proximate an end of the bearing stator leg;
  ii) tapers inwardly proximate an end of the bearing stator leg; and,
  iii) tapers inwardly proximate an end of the bearing stator leg and the tapering at least one of:
    (1) has a height of at least one of:
      (a) between 0 mm and 10 mm; and,
      (b) about 5 mm;
    (2) has a width of at least one of:
      (a) between 0 mm and 4 mm; and,
      (b) between 0.5 mm and 2 mm;
    (3) is towards a centreline of magnetic bearing member; and,
    (4) is such that a radial restoring force from the at least one bearing coil increases as the rotor is radially offset from a central radial position.

11. A heart pump according to claim 1, wherein at least one of:
a) at least one of the first and second magnetic bearing members at least one of:
  i) includes an annular permanent bearing magnet;
  ii) includes an annular iron member;
  iii) has at least one of:
    (1) a thickness that is at least one of:
      (a) between 1 mm and 3 mm;
      (b) about 2.4 mm; and,
    (2) a width that is at least one of:
      (a) between 3 mm and 4.5 mm;
      (b) about 2.5 mm; and,
      (c) about 3.5 mm;
  iv) are provided on a common annular laminated or solid iron bearing rotor yoke;
  v) tapers inwardly towards the second rotor face;
  vi) tapers inwardly towards the second rotor face and wherein the taper is at least one of:
    (1) towards a centreline of magnetic bearing member; and,
    (2) such that a radial restoring force from the at least one bearing coil increases as the rotor is radially offset from a central radial position; and,
  vii) tapers inwardly towards the second rotor face and at least one of the first and second magnetic bearing members includes a tapered iron shoe; and,
b) the bearing rotor yoke has at least one of:
  i) a width that is at least one of:
    (1) between 10 mm and 13 mm; and,
    (2) about 11 mm; and,
  ii) a thickness that is at least one of:
    (1) between 1 mm and 5 mm;
    (2) between 1.5 mm and 2.5 mm; and,
    (3) about 1.9 mm.

12. A heart pump according to claim 1, wherein the second bearing stator leg is tapered and the second magnetic bearing member includes a permanent magnet and wherein one of:
a) the first bearing stator leg is substantially untapered and the first bearing magnetic member is an annular iron member; and,
b) the first bearing stator leg is tapered and the first bearing magnetic member is an annular permanent magnet.

13. A heart pump according to claim 1, wherein the vanes include first and second sets of vanes provided on a rotor body, the rotor being positioned within the cavity, and wherein:
a) the cavity includes a first cavity portion and a second cavity portion;
b) the at least one inlet includes a first inlet and a second inlet;
c) the at least one outlet includes a first outlet and a second outlet;
d) the first cavity portion has the first inlet and the first outlet, and the first set of vanes is provided within the first cavity portion so as to define a first pump that provides at least partial left ventricular function; and,
e) the second cavity portion has the second inlet and the second outlet, and the second set of vanes is provided within the second cavity portion so as to define a second pump that provides at least partial right ventricular function.

14. A heart pump according to claim 1, wherein the impeller and housing cooperate to define a hydrodynamic bearing in the event that the magnetic bearing fails and wherein at least one of:
a) the hydrodynamic bearing is defined at least in part by an upper surface of at least some of the vanes of the impeller;
b) the hydrodynamic bearing is defined by an upper surface of vanes of the impeller facing the first end of the cavity;
c) the hydrodynamic bearing is defined at least in part by an upper surface of at least some of the vanes of the impeller and the upper surface includes a leading ramp and a trailing flat pad; and,
d) the hydrodynamic bearing is defined at least in part by an upper surface of at least some of the vanes of the impeller, the upper surface includes a leading ramp and a trailing flat pad, and wherein at least one of:
  i) the flat pad has an inner radius of at least one of:
    (1) between 16 mm and 22 mm; and,
    (2) between 18 mm and 20 mm;
  ii) the flat pad has a length of at least one of:
    (1) between 1 mm and 5 mm;
    (2) between 2 mm and 4 mm; and,
    (3) about 3 mm;
  iii) the ramp has a length of at least one of:
    (1) between 5 mm and 15 mm;
    (2) between 8 mm and 12 mm; and,
    (3) about 10 mm; and,
  iv) the ramp has a height of at least one of:
    (1) between 0.02 mm and 0.1 mm;
    (2) between 0.04 mm and 0.08 mm; and,
    (3) about 0.06 mm.

15. A heart pump according to claim 1, wherein the heart pump includes a controller that controls operation of the drive and bearing in use and wherein the controller controls the drive to selectively generate an axial attractive force to at least one of:
a) move the impeller within the cavity; and,
b) increase shock resistance when operating using a hydrodynamic bearing in the event that the magnetic bearing fails.

16. A heart pump according to claim 15, wherein the controller:
a) detects at least one of:
  i) failure of the magnetic bearing based on at least one of:

(1) a bearing indicator indicative of a current used by the magnetic bearing;
(2) a drive indicator indicative of a current used by the drive; and,
(3) sensor signals; and,
ii) movement of the impeller to the second end of the cavity when the magnetic bearing has failed; and,
b) controls the drive to generate the axial attractive force in response to the detection.

17. A heart pump including:
a) a housing defining a cavity including:
  i) at least one inlet aligned with an axis of the cavity; and,
  ii) at least one outlet provided in a circumferential outer wall of the cavity;
b) an impeller provided within the cavity, the impeller including a rotor and vanes mounted on the rotor for urging fluid from the inlet radially outwardly to the outlet; and,
c) a magnetic bearing including:
  i) first and second annular magnetic bearing members mounted within and proximate a second face of the rotor, the first magnetic bearing member being provided radially outwardly of the second magnetic bearing member;
  ii) a number of circumferentially spaced substantially U-shaped bearing stators mounted in the housing proximate a second end of the cavity, each U-shaped bearing stator having first and second bearing stator legs that interact with the first and second magnetic bearing members respectively; and,
  iii) at least one bearing coil on each bearing stator that generates a magnetic field that cooperates with the magnetic bearing members to thereby at least one of:
    (1) control an axial position of the impeller; and,
    (2) at least partially restrain radial movement of the impeller.

* * * * *